(12) United States Patent
Angelescu

(10) Patent No.: US 10,408,040 B2
(45) Date of Patent: *Sep. 10, 2019

(54) PASSIVE MICRO-VESSEL AND SENSOR

(71) Applicant: FLUIDION SAS, Paris (FR)

(72) Inventor: Dan E Angelescu, Le Perreux sur Marne (FR)

(73) Assignee: FLUIDION SAS (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/871,383

(22) Filed: Jan. 15, 2018

(65) Prior Publication Data

US 2018/0216453 A1    Aug. 2, 2018

Related U.S. Application Data

(63) Continuation-in-part of application No. 14/244,292, filed on Apr. 3, 2014, now Pat. No. 9,869,613, which
(Continued)

(51) Int. Cl.
*E21B 47/022* (2012.01)
*E21B 49/08* (2006.01)
(Continued)

(52) U.S. Cl.
CPC ...... *E21B 47/02208* (2013.01); *E21B 34/063* (2013.01); *E21B 41/00* (2013.01);
(Continued)

(58) Field of Classification Search
CPC .......... E21B 47/02208; E21B 47/1015; E21B 34/063; E21B 41/00; E21B 49/081; G01N 1/16; G01N 1/12; G01N 1/40; G01N 1/2042; G01N 1/04; G01N 11/02; G01N 2001/1056; G01N 2001/1031;
(Continued)

(56) References Cited

U.S. PATENT DOCUMENTS 1,909,205 A   5/1933   McCollum
3,399,727 A   9/1968   Graham et al.
(Continued)

FOREIGN PATENT DOCUMENTS

EP   0620893 B1   12/2000
EP   1137862 B1   3/2004
(Continued)

OTHER PUBLICATIONS

Angelescu, "Highly Integrated Microfluidics Design," Integrated Microsystems Series, Artech House, Inc., entire book, 2011.
(Continued)

*Primary Examiner* — J. Christopher Ball
(74) *Attorney, Agent, or Firm* — Sunstein Kann Murphy & Timbers LLP

(57) ABSTRACT

An electrically passive device and method for in-situ acoustic emission, and/or releasing, sampling and/or measuring of a fluid or various material(s) is provided. The device may provide a robust timing mechanism to release, sample and/or perform measurements on a predefined schedule, and, in various embodiments, emits an acoustic signal sequence(s) that may be used for triangulation of the device position within, for example, a hydrocarbon reservoir or a living body.

25 Claims, 63 Drawing Sheets

Related U.S. Application Data is a continuation-in-part of application No. 13/760,879, filed on Feb. 6, 2013, now Pat. No. 9,389,158, which is a continuation-in-part of application No. 13/025,467, filed on Feb. 11, 2011, now Pat. No. 8,506,907.

(60) Provisional application No. 61/337,998, filed on Feb. 12, 2010.

(51) Int. Cl.

| | |
|---|---|
| *F16K 99/00* | (2006.01) |
| *G01N 1/12* | (2006.01) |
| *G01N 1/16* | (2006.01) |
| *G01N 1/20* | (2006.01) |
| *G01N 1/40* | (2006.01) |
| *G01N 11/02* | (2006.01) |
| *G01V 1/38* | (2006.01) |
| *G01V 15/00* | (2006.01) |
| *E21B 47/10* | (2012.01) |
| *E21B 34/06* | (2006.01) |
| *E21B 41/00* | (2006.01) |
| *G01N 1/10* | (2006.01) |
| *G01V 1/04* | (2006.01) |
| *G01V 1/42* | (2006.01) |

(52) U.S. Cl.
CPC ........ *E21B 47/1015* (2013.01); *E21B 49/081* (2013.01); *F16K 99/003* (2013.01); *F16K 99/0059* (2013.01); *G01N 1/12* (2013.01); *G01N 1/16* (2013.01); *G01N 1/2042* (2013.01); *G01N 1/40* (2013.01); *G01N 11/02* (2013.01); *G01V 1/3852* (2013.01); *G01V 15/00* (2013.01); *B01L 2200/027* (2013.01); *B01L 2400/0683* (2013.01); *G01N 2001/1031* (2013.01); *G01N 2001/1056* (2013.01); *G01V 1/04* (2013.01); *G01V 1/42* (2013.01)

(58) Field of Classification Search
CPC .. G01V 1/3852; G01V 15/00; F16K 99/0059; F16K 99/003; B01L 2200/027; B01L 2400/0683

See application file for complete search history.

(56) References Cited

U.S. PATENT DOCUMENTS

| | | | |
|---|---|---|---|
| 3,729,855 A | 5/1973 | Niskin | |
| 3,766,733 A | 10/1973 | Drzewiecki et al. | |
| 3,826,144 A | 7/1974 | Wessels | |
| 4,057,780 A | 11/1977 | Shuck | |
| 4,547,468 A | 10/1985 | Jones et al. | |
| 4,631,956 A | 12/1986 | Walden et al. | |
| 4,791,251 A | 12/1988 | Carter et al. | |
| 4,893,505 A | 1/1990 | Marsden et al. | |
| 5,058,674 A | 10/1991 | Schultz et al. | |
| 5,441,110 A | 8/1995 | Scott, III | |
| 5,503,225 A | 4/1996 | Withers | |
| 6,443,228 B1 | 9/2002 | Aronstam et al. | |
| 6,457,539 B1 | 10/2002 | Skinner | |
| 6,619,311 B2 | 9/2003 | O'Connor et al. | |
| 6,891,477 B2 | 5/2005 | Aronstam et al. | |
| 6,898,529 B2 | 5/2005 | Gao et al. | |
| 7,082,993 B2 | 8/2006 | Ayoub et al. | |
| 7,134,492 B2 | 11/2006 | Willberg et al. | |
| 7,197,923 B1 | 4/2007 | Wright et al. | |
| 7,216,533 B2 | 5/2007 | McGregor et al. | |
| 7,318,912 B2 | 1/2008 | Pezzuto et al. | |
| 7,455,667 B2 | 11/2008 | Uhland et al. | |
| 7,712,527 B2 | 5/2010 | Roddy | |
| 8,129,318 B2 | 3/2012 | McDaniel et al. | |
| 8,506,907 B2 | 8/2013 | Angelescu | |
| 9,389,158 B2 | 7/2016 | Angelescu | |
| 9,772,261 B2 | 9/2017 | Angelescu et al. | |
| 9,869,613 B2 | 1/2018 | Hausot et al. | |
| 2003/0092393 A1 | 5/2003 | Tokhtuev et al. | |
| 2003/0104590 A1 | 6/2003 | Santini, Jr. et al. | |
| 2007/0048192 A1 | 3/2007 | Kartalov et al. | |
| 2007/0193377 A1 | 8/2007 | Irani et al. | |
| 2008/0047836 A1 | 2/2008 | Strand et al. | |
| 2009/0126996 A1 | 5/2009 | Villareal et al. | |
| 2009/0288820 A1 | 11/2009 | Barron et al. | |
| 2010/0051266 A1 | 3/2010 | Roddy et al. | |
| 2011/0186290 A1 | 8/2011 | Roddy et al. | |
| 2011/0198221 A1 | 8/2011 | Angelescu | |
| 2011/0314936 A1 | 12/2011 | Baxter et al. | |
| 2012/0037368 A1 | 2/2012 | Eick et al. | |
| 2012/0048538 A1 | 3/2012 | Brannon | |
| 2013/0269423 A1 | 10/2013 | Angelescu | |

FOREIGN PATENT DOCUMENTS

| | | |
|---|---|---|
| FR | 2253409 A5 | 6/1975 |
| GB | 2443900 A | 5/2008 |
| GB | 2459793 A | 11/2009 |
| WO | WO 11/100509 A2 | 8/2011 |
| WO | WO 13/043737 A1 | 3/2013 |
| WO | WO 15/150429 A2 | 10/2015 |

OTHER PUBLICATIONS

Beeby et al., "MEMS Mechanical Sensors," Artech House, Inc., entire book, 2004.

Grayson et al., "Multi-pulse drug delivery from a resorbable polymeric microchip device," Nature Materials, vol. 2, 9 pages, Nov. 2003.

Miller et al., "Fracturing Oil Shale With Explosives for In Situ Recovery," Am. Chem. Soc. 167$^{th}$ Nat'l Mtg., Los Angeles—Symposium on Shale Oil, Tar Sands and Related Fuel Sources, pp. 60-85, Mar. 31-Apr. 5, 1974.

Montgomery et al., "Hydraulic Fracturing—History of an Enduring Technology," Journal of Petroleum Technology, pp. 26-41, Dec. 2010.

Oh et al., "Topical review: A review of microvalves," Journal of Micromechanics and Microengineering, vol. 16, pp. R13-R39, 2006.

Prescott et al., "Chronic, programmed polypeptide delivery from an implanted, multireservoir microchip device," Nature Biotechnology, vol. 24, No. 4, pp. 437-438, Apr. 2006.

Santini, Jr. et al., "Microchips as Controlled Drug-Delivery Devices," Angew. Chem. Int. Ed., vol. 39, pp. 2396-2407, 2000.

Staples et al., "Application of Micro- and Nano-Electromechanical Devices to Drug Delivery," Pharmaceutical Research, vol. 23, No. 5, pp. 847-863, May 2006.

Stone et al., "Engineering Flows in Small Devices: Microfluidics Toward a Lab-on-a-Chip," Annual Review of Fluid Mechanics, vol. 36, pp. 381-411, 2004.

Vogel et al., "Optical and acoustic investigations of the dynamics of laser-produced cavitation bubbles near a solid boundary," Journal of Fluid Mechanics, vol. 206, pp. 299-338, 1989.

European Patent Office, International Preliminary Report on Patentability—International Application No. PCT/EP2014/052350 dated May 5, 2015, 6 pages.

European Patent Office, European Search Report, Application No. EP 16203352, dated Mar. 23, 2017, 4 pages.

International Searching Authority, International Search Report—International Application No. PCT/US2011/024467, dated Sep. 23, 2011, together with the Written Opinion of the International Searching Authority, 8 pages.

International Searching Authority, International Search Report—International Application No. PCT/EP2014/052350, dated May 20, 2014, together with the Written Opinion of the International Searching Authority, 10 pages.

(56) References Cited

OTHER PUBLICATIONS

International Searching Authority, International Search Report—International Application No. PCT/EP2015/057126, dated Dec. 7, 2015, together with the Written Opinion of the International Searching Authority, 22 pages.

International Searching Authority, International Search Report—International Application No. PCT/EP2019/050809, dated Apr. 5, 2019, together with the Written Opinion of the International Searching Authority, 15 pages.

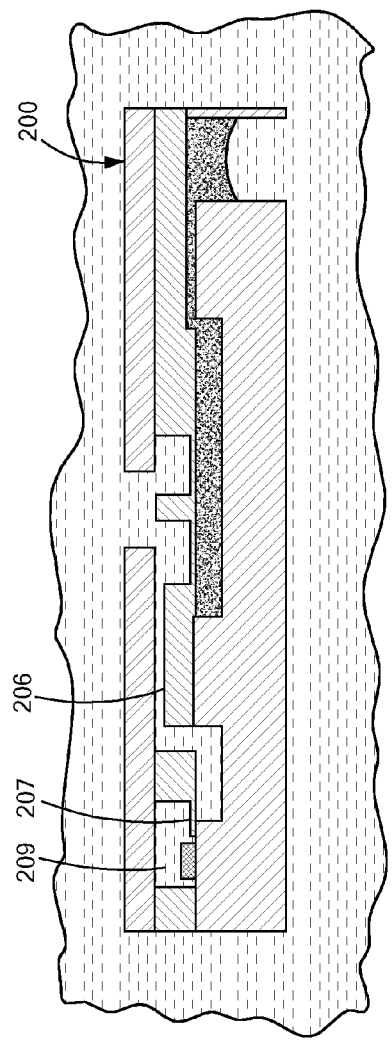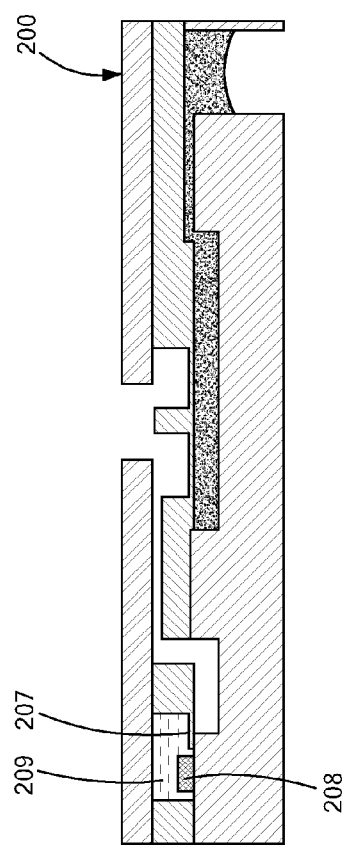
FIG. 2C
FIG. 2D

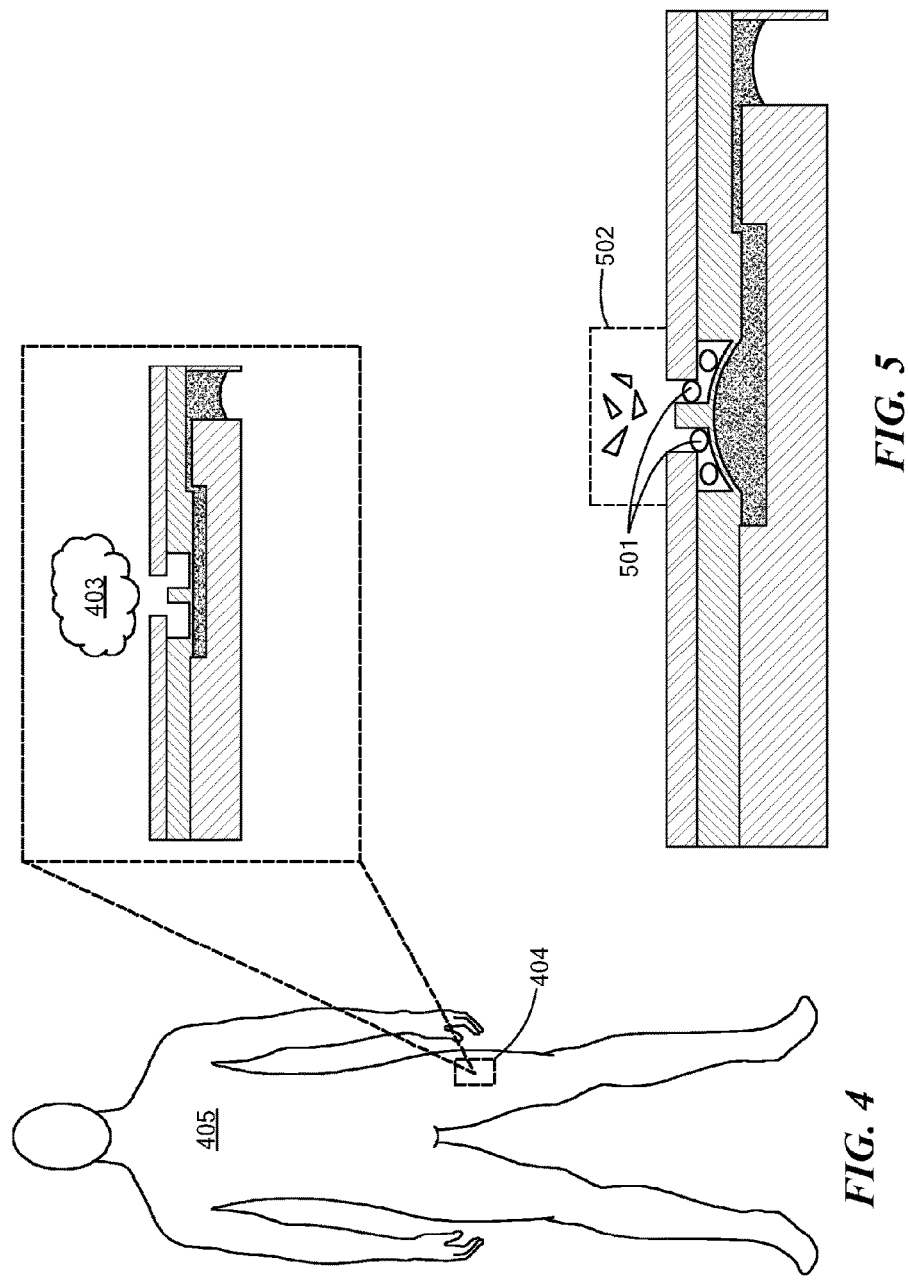

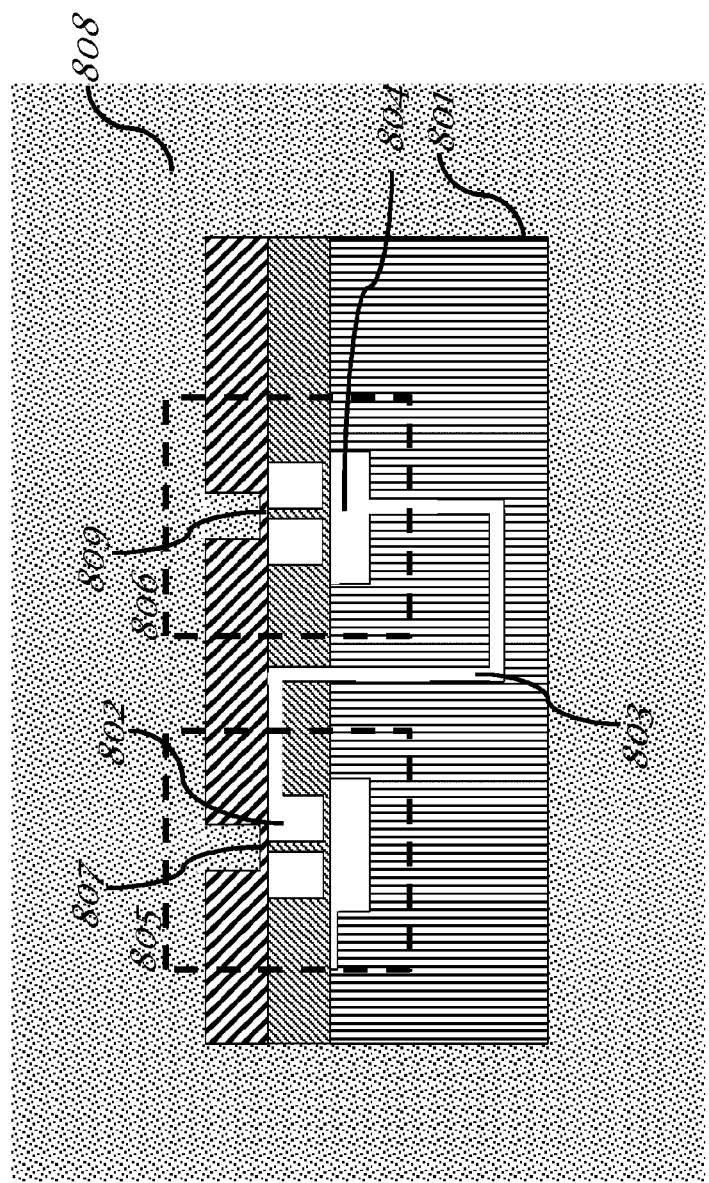
Fig. 8-A

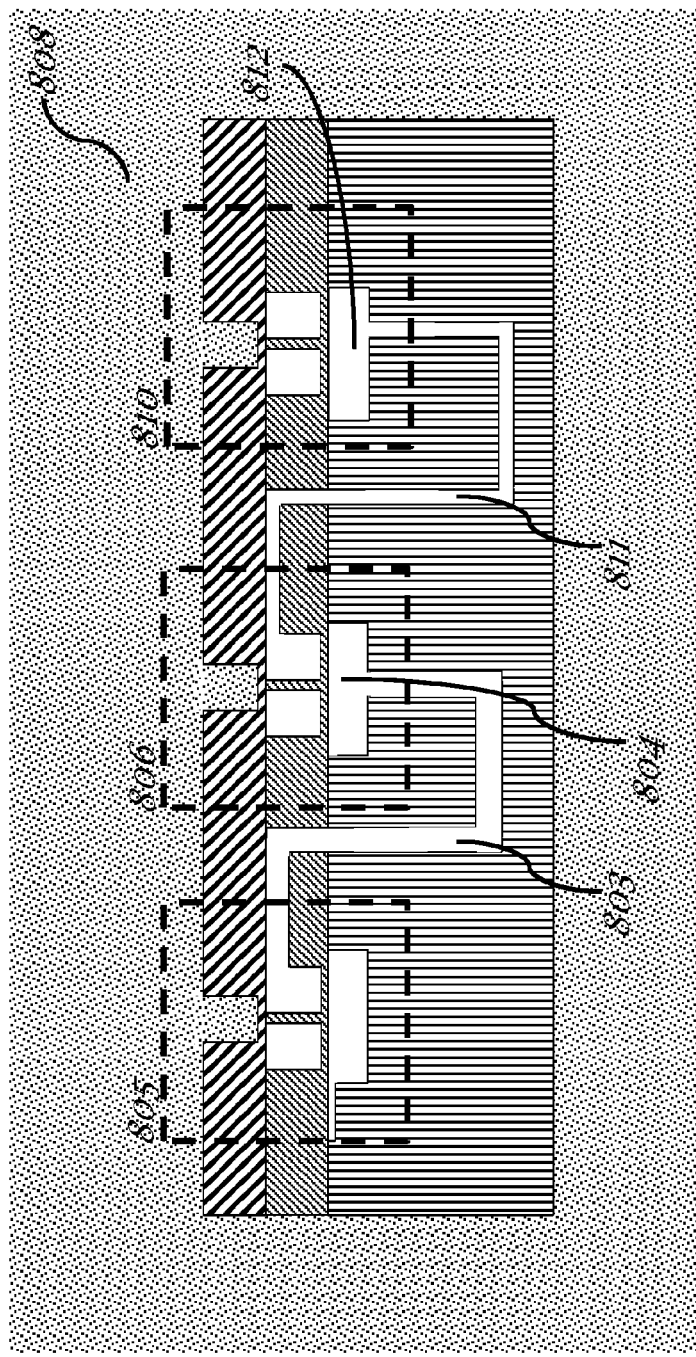
Fig. 8-B

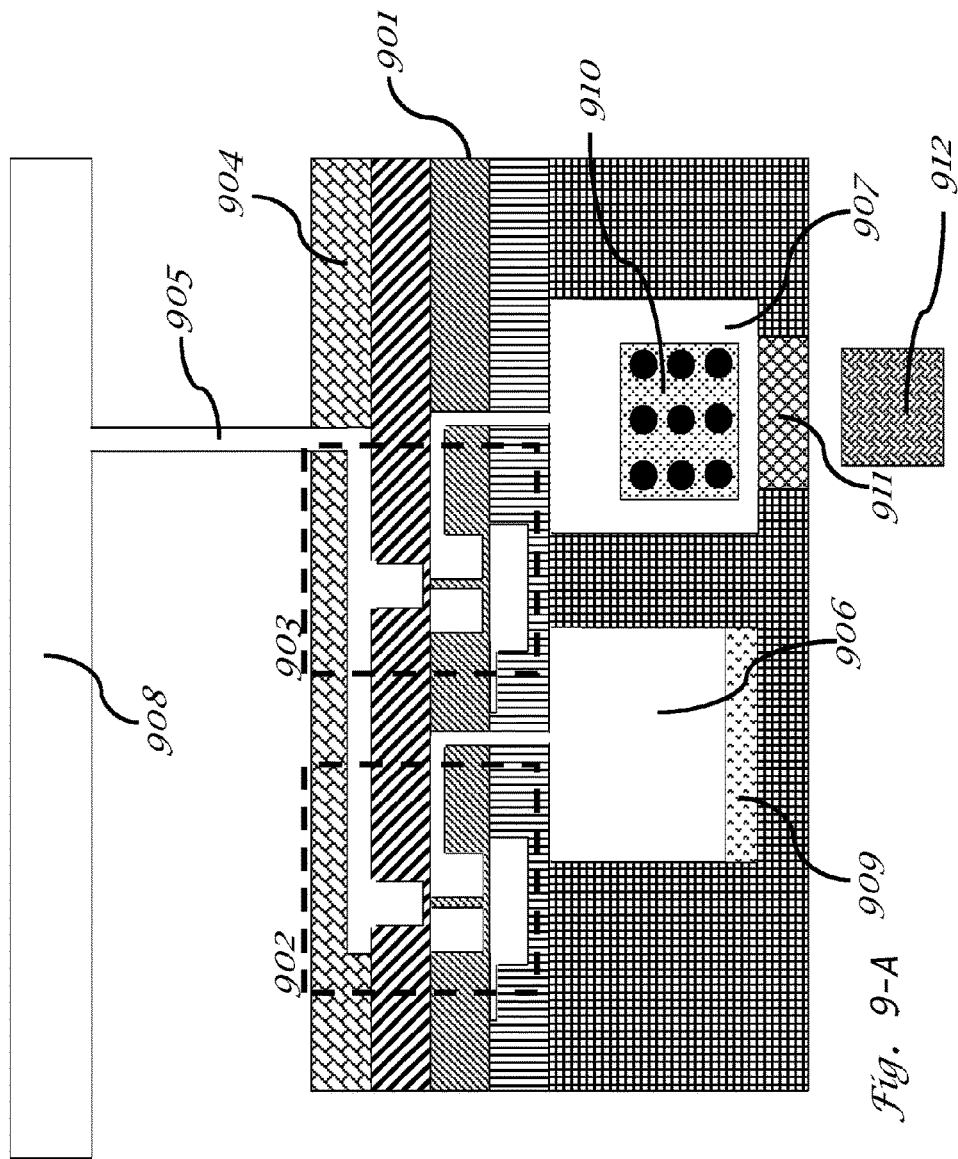

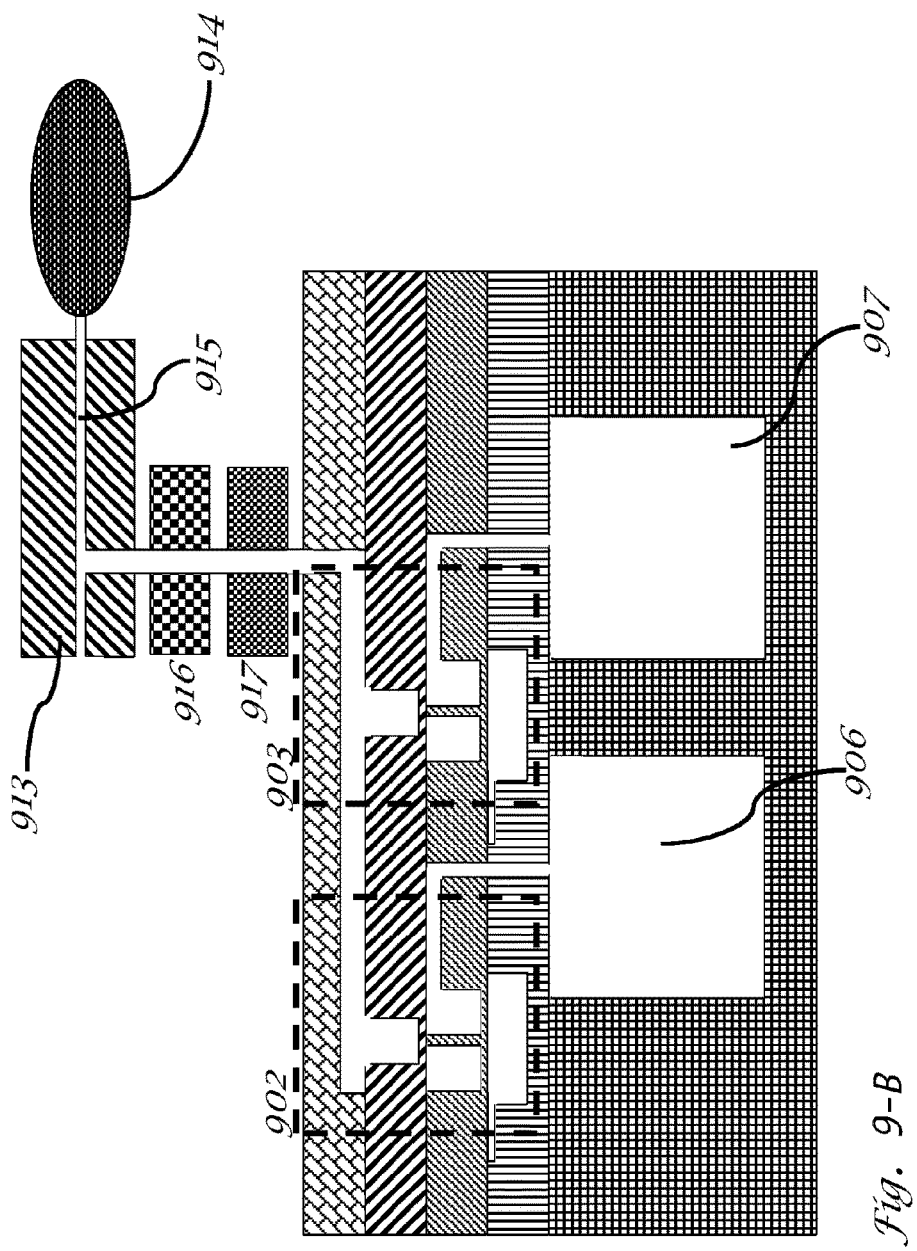

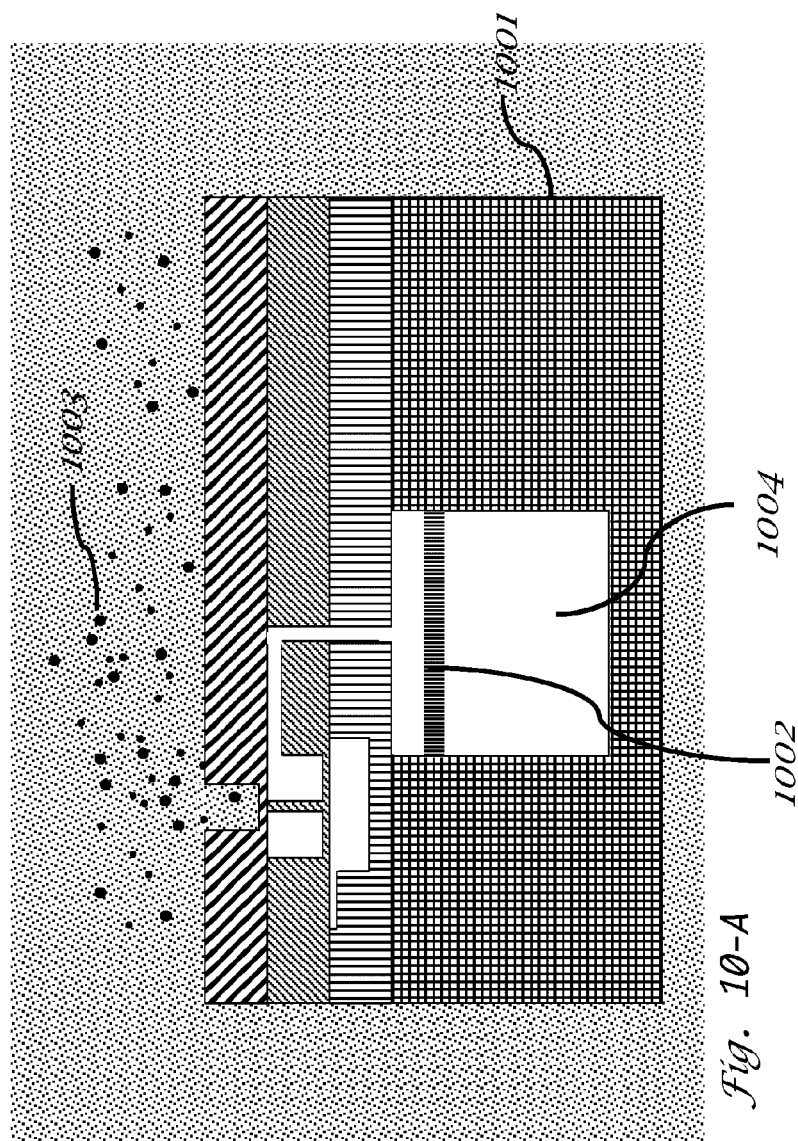

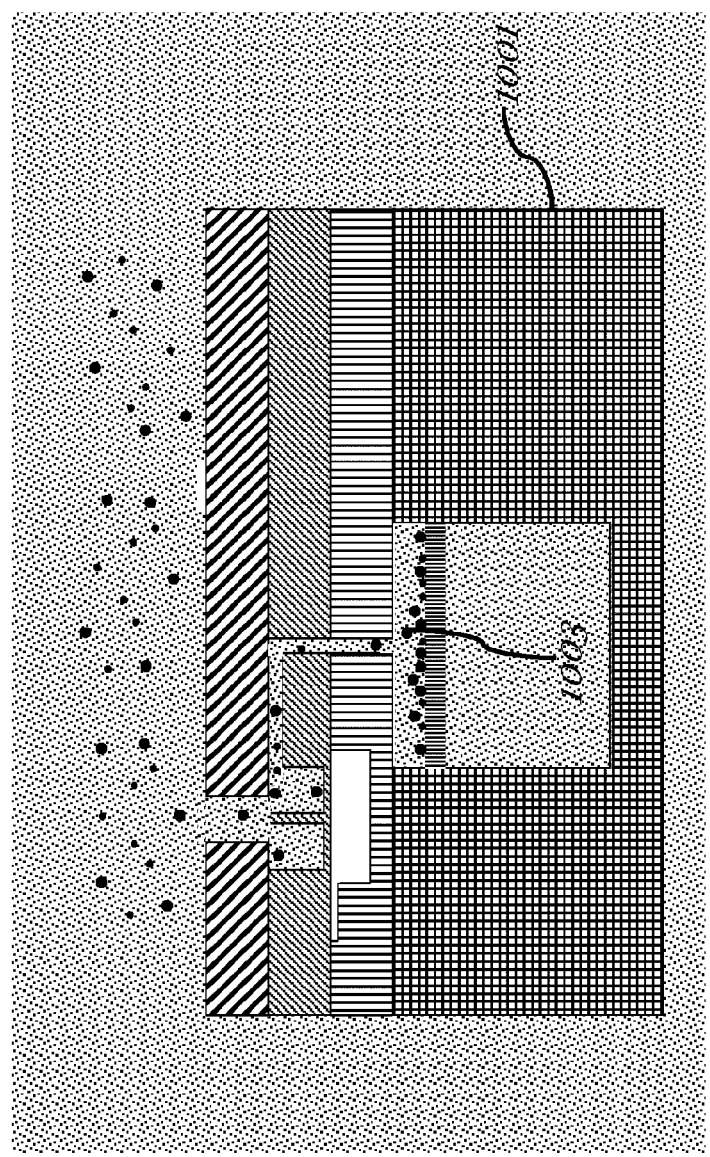
Fig. 10-B

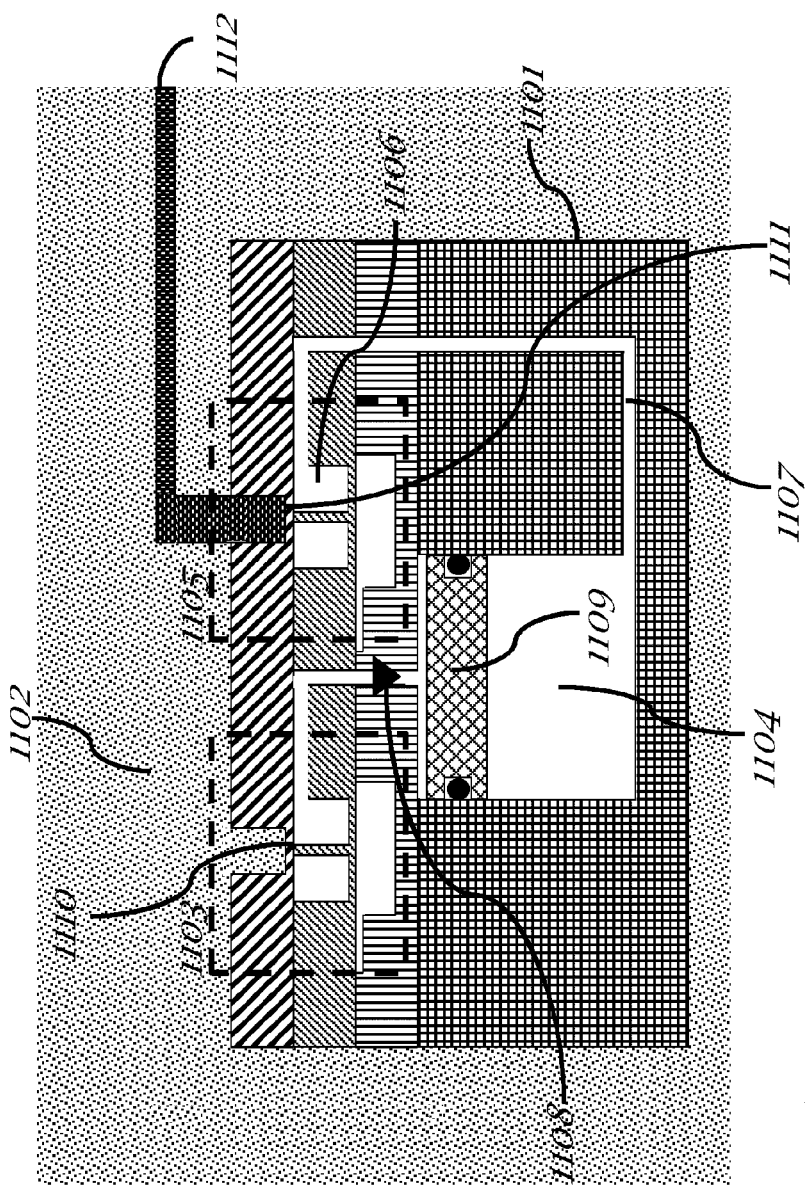
Fig. 11-A

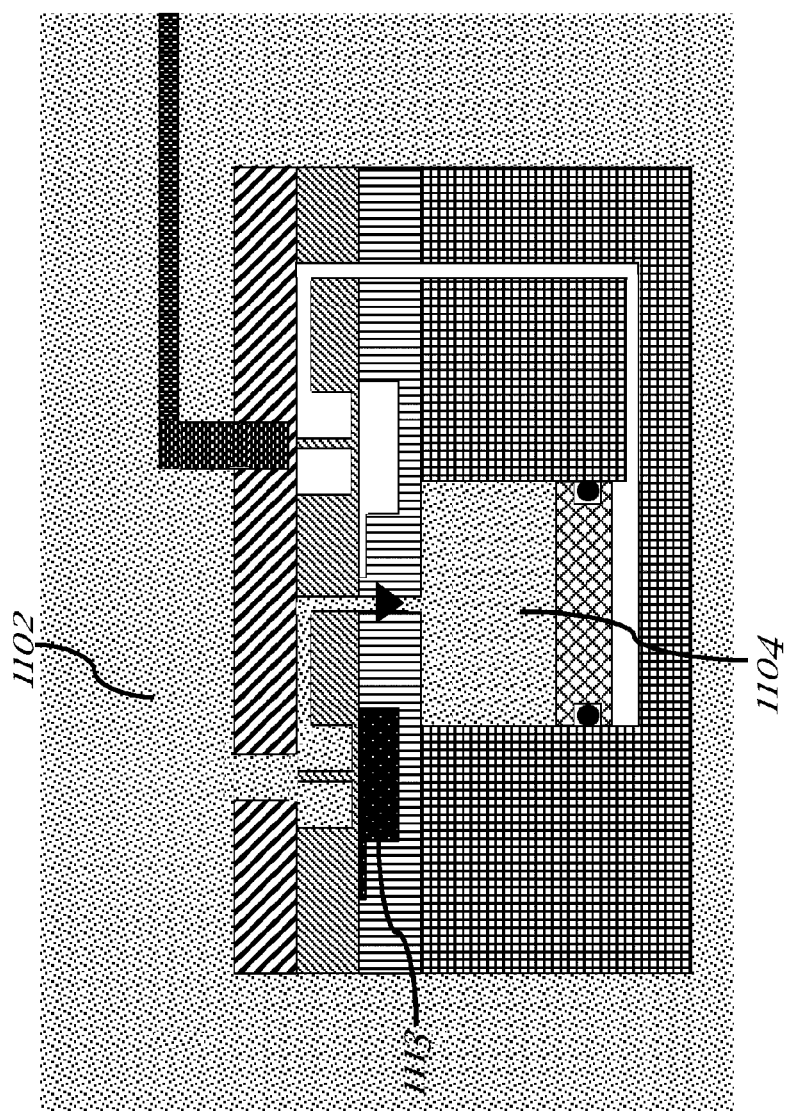
Fig. 11-B

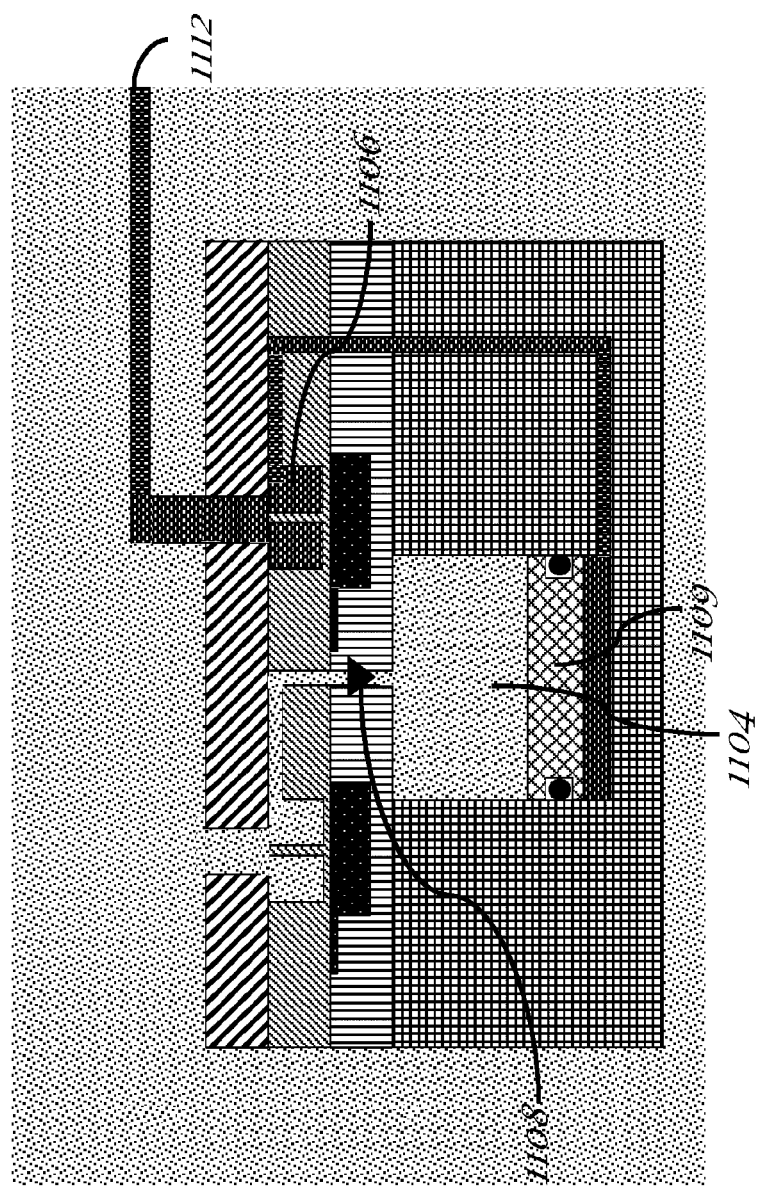
Fig. 11-C

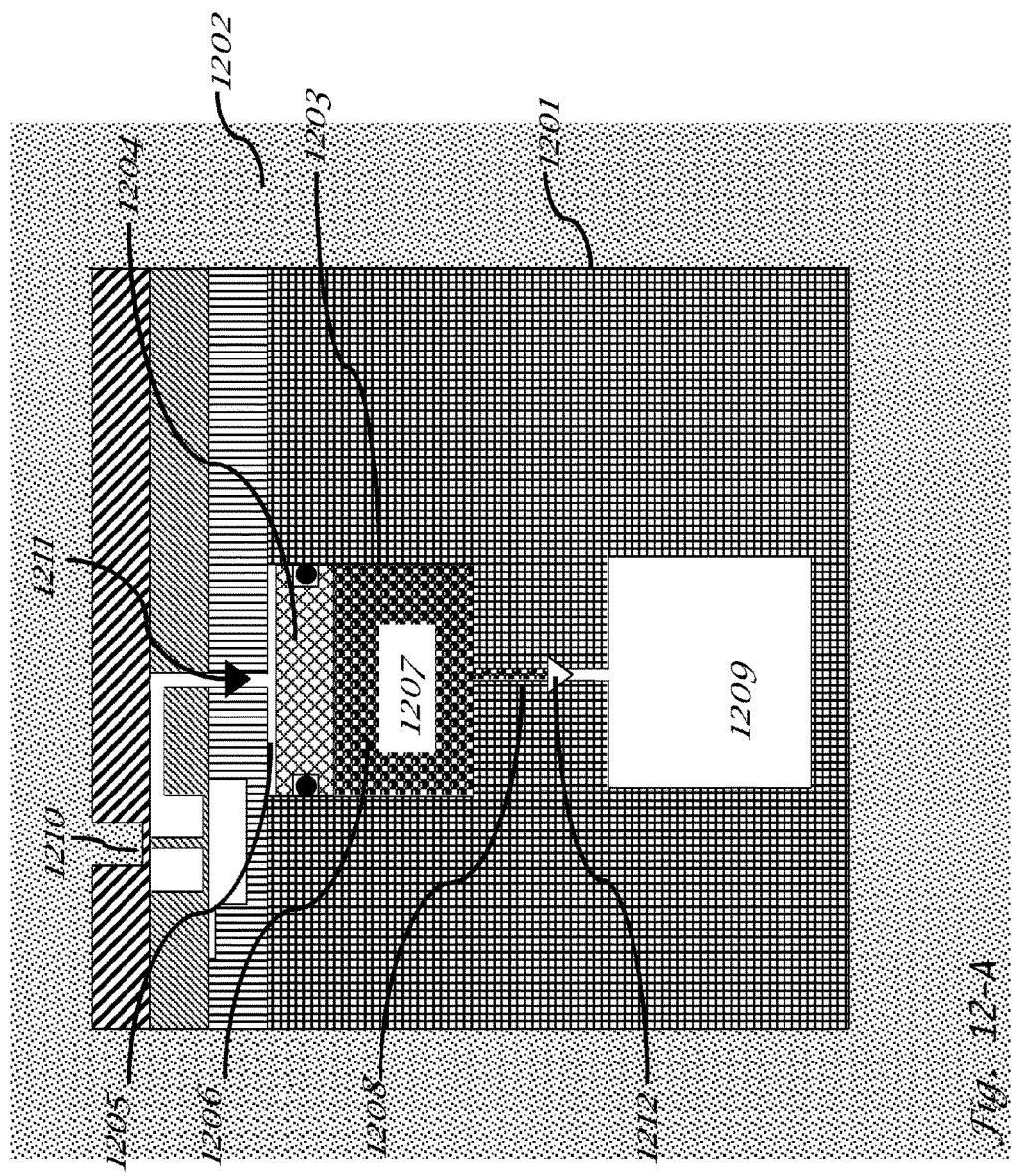
Fig. 12-A

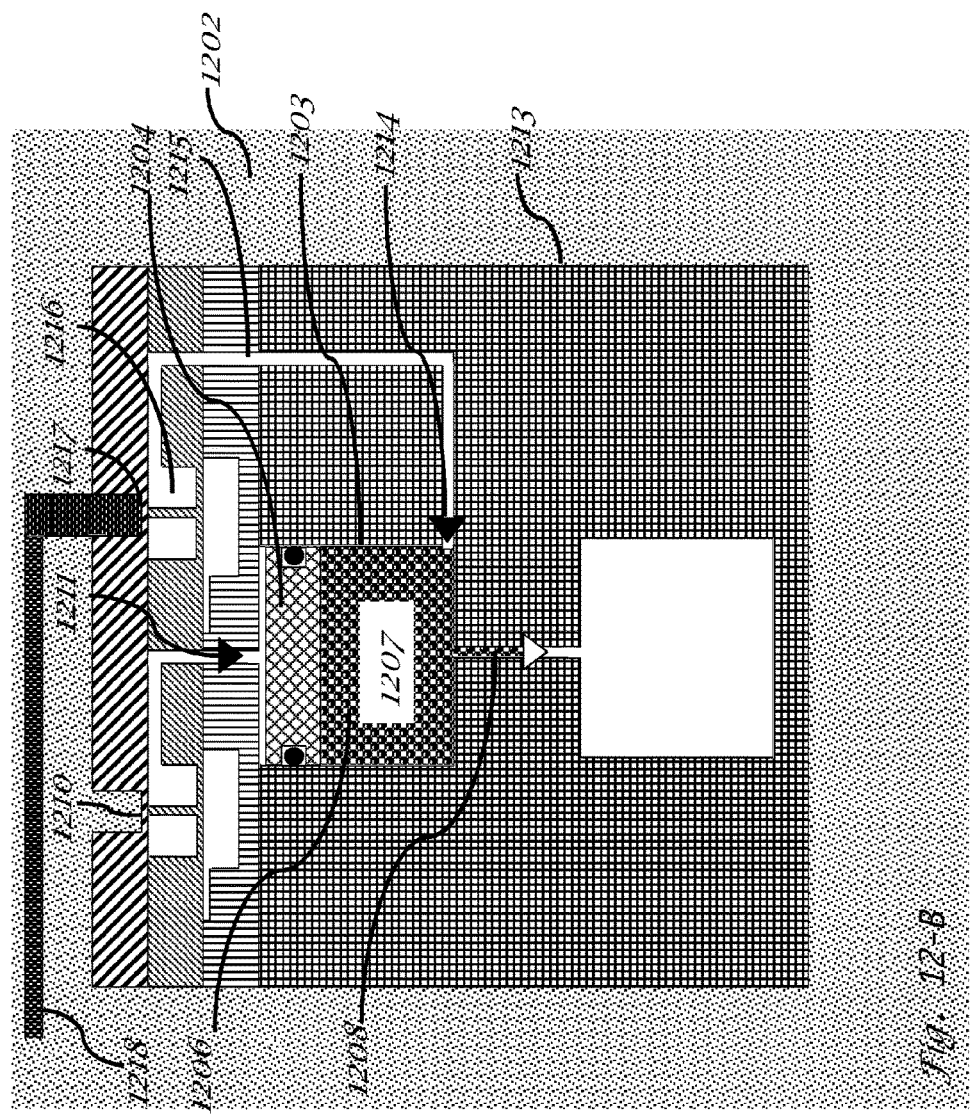

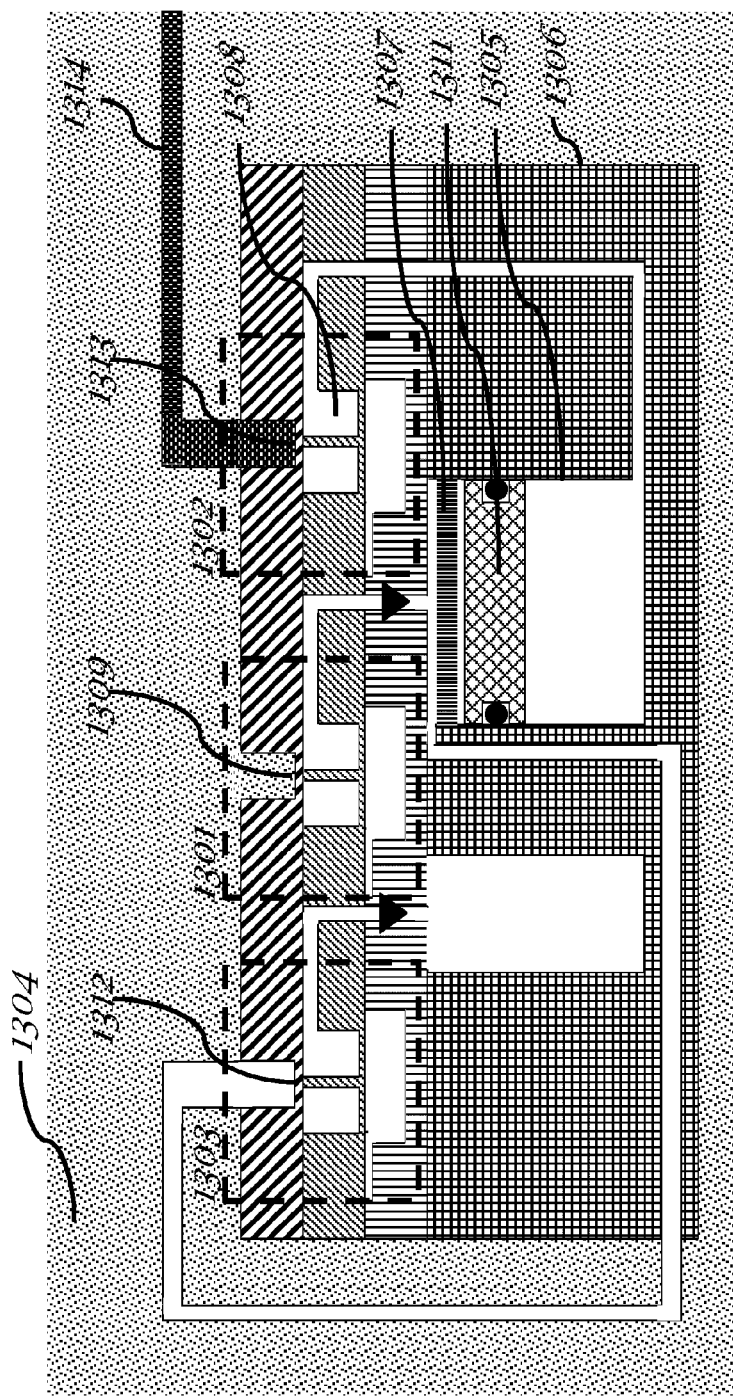
Fig. 13-A

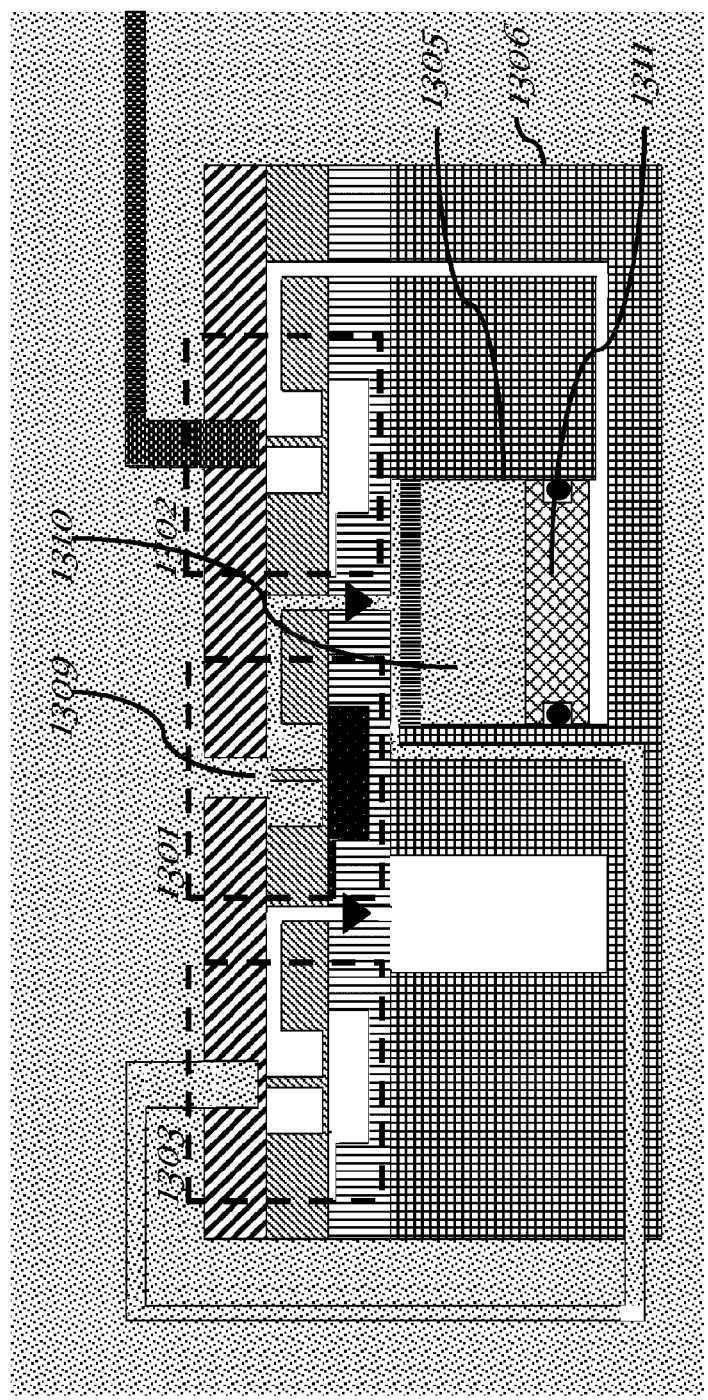
Fig. 13-B

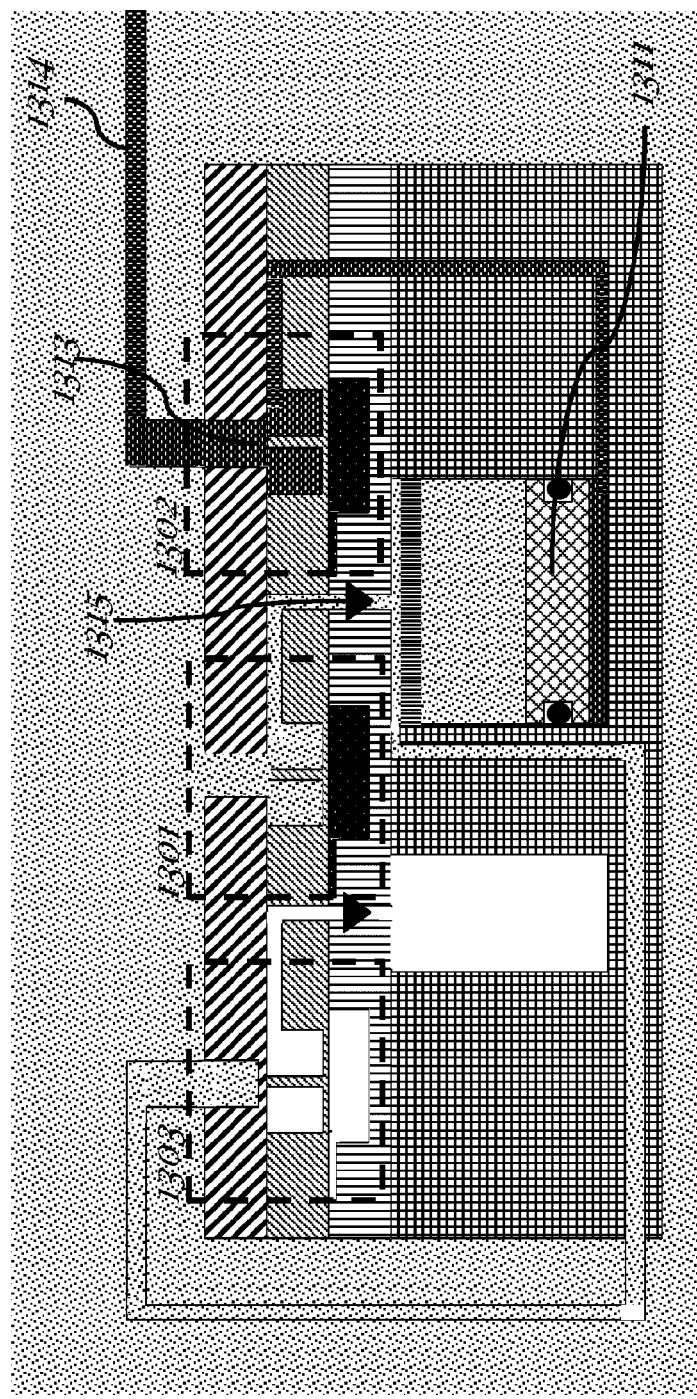
Fig. 13-C

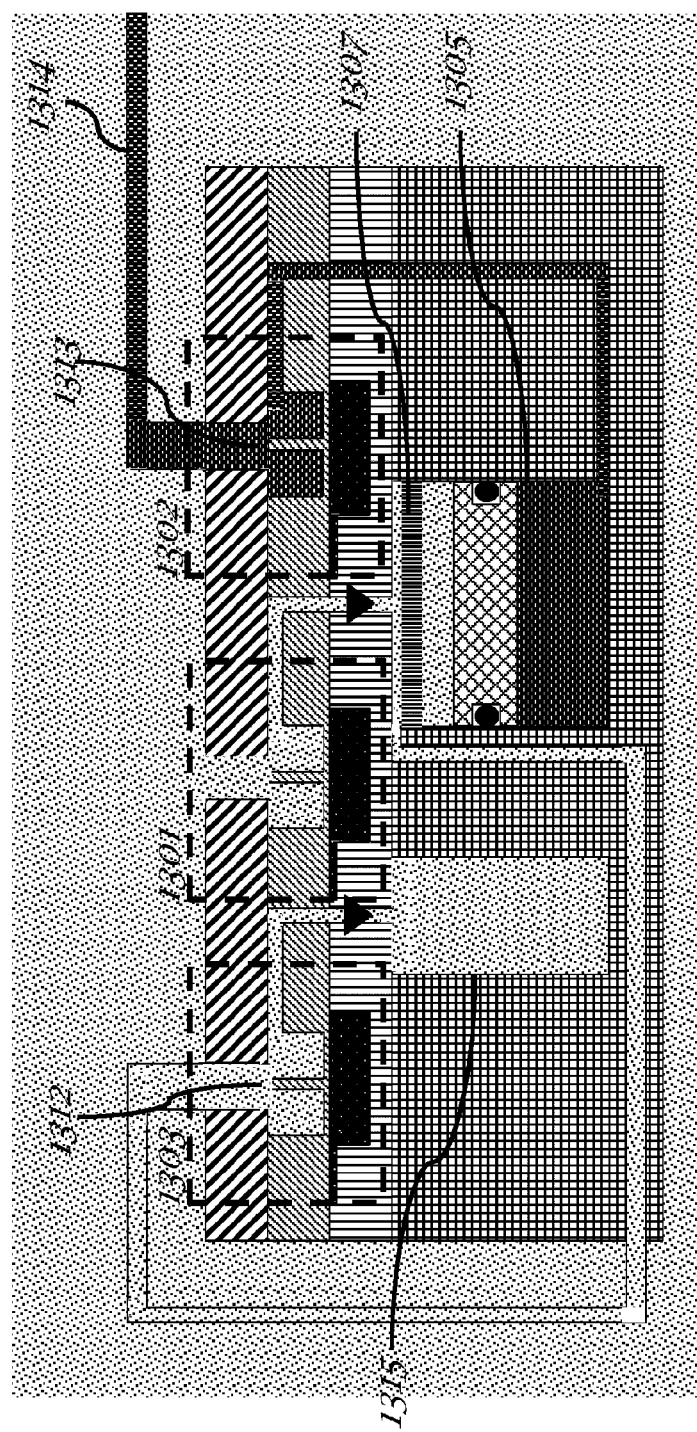
Fig. 13-D

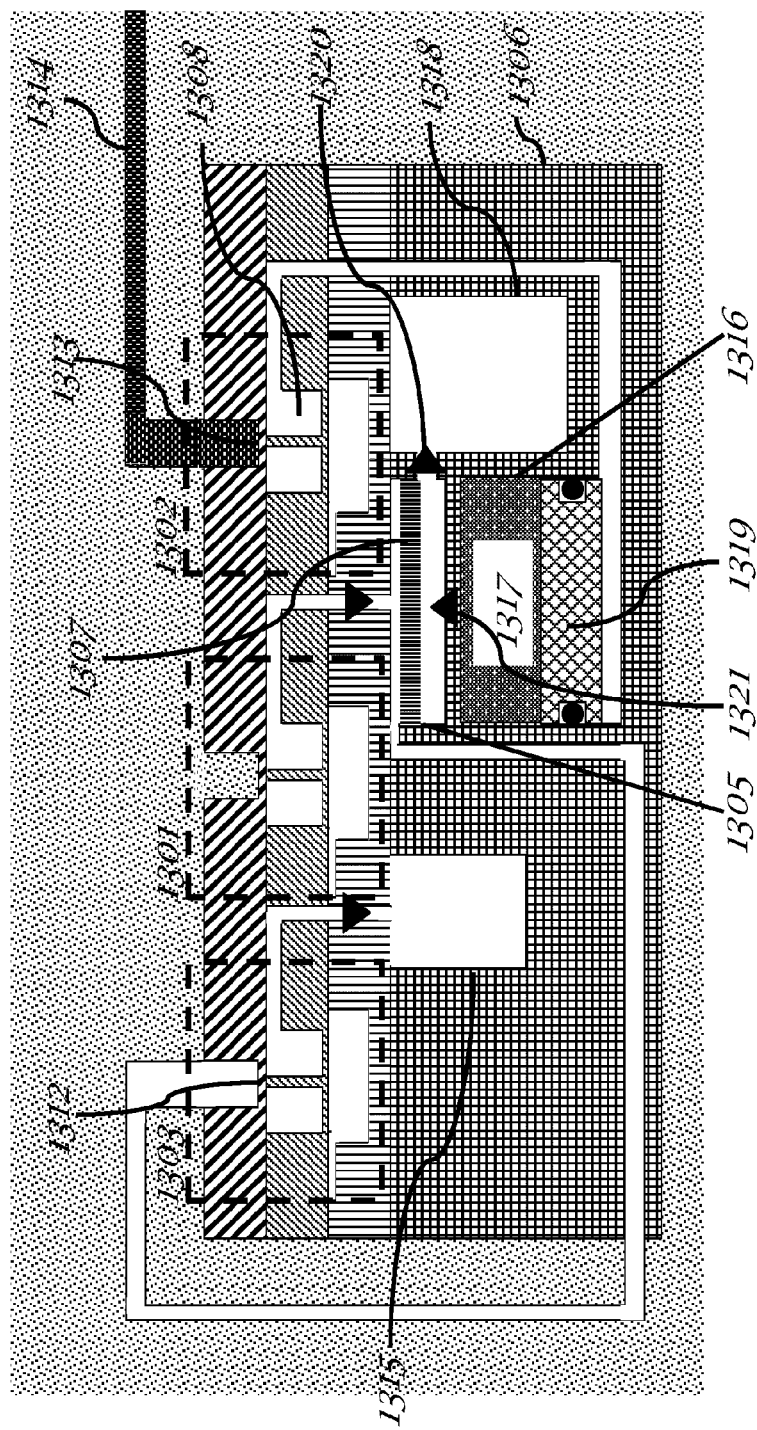
Fig. 13-E

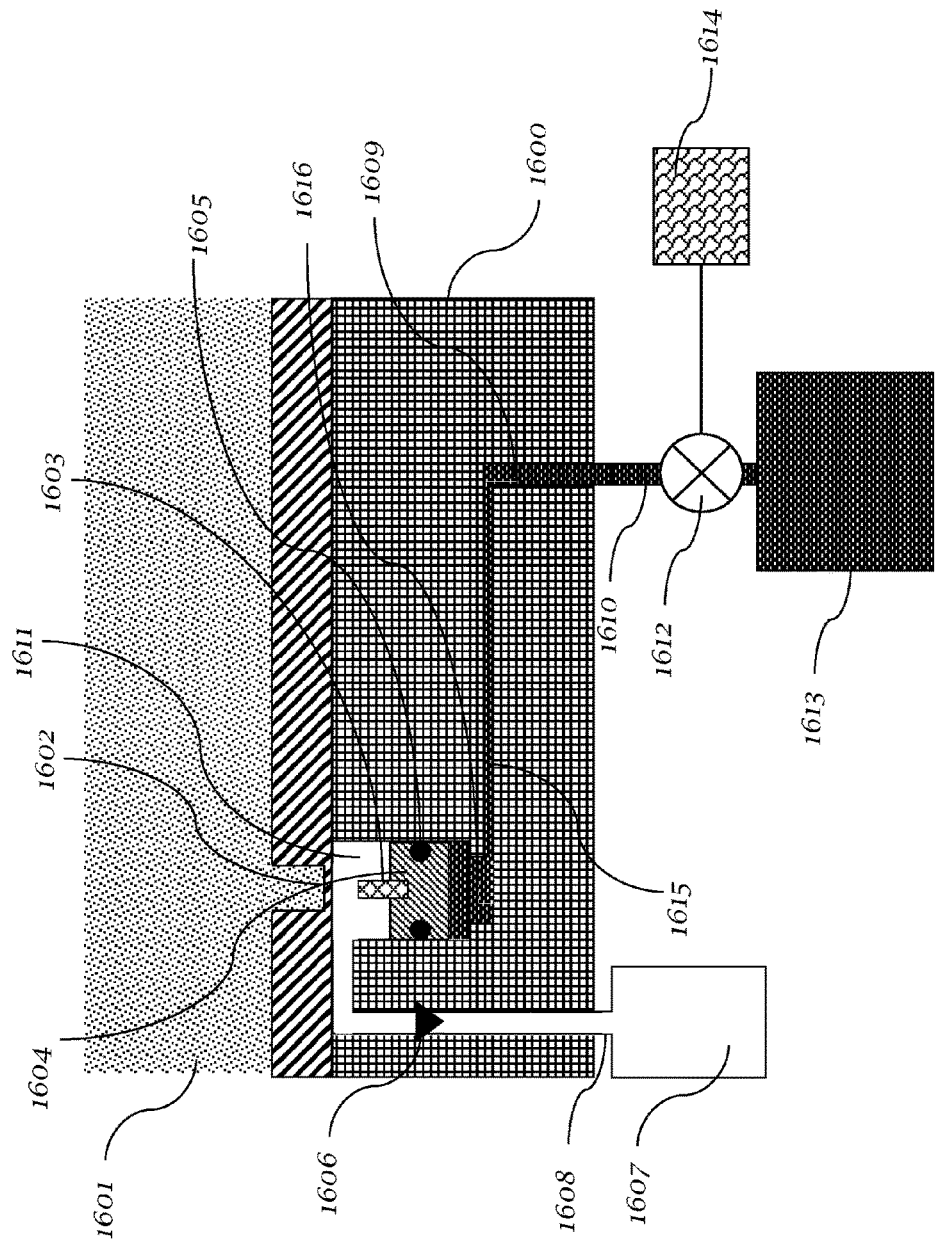
FIG. 16-A

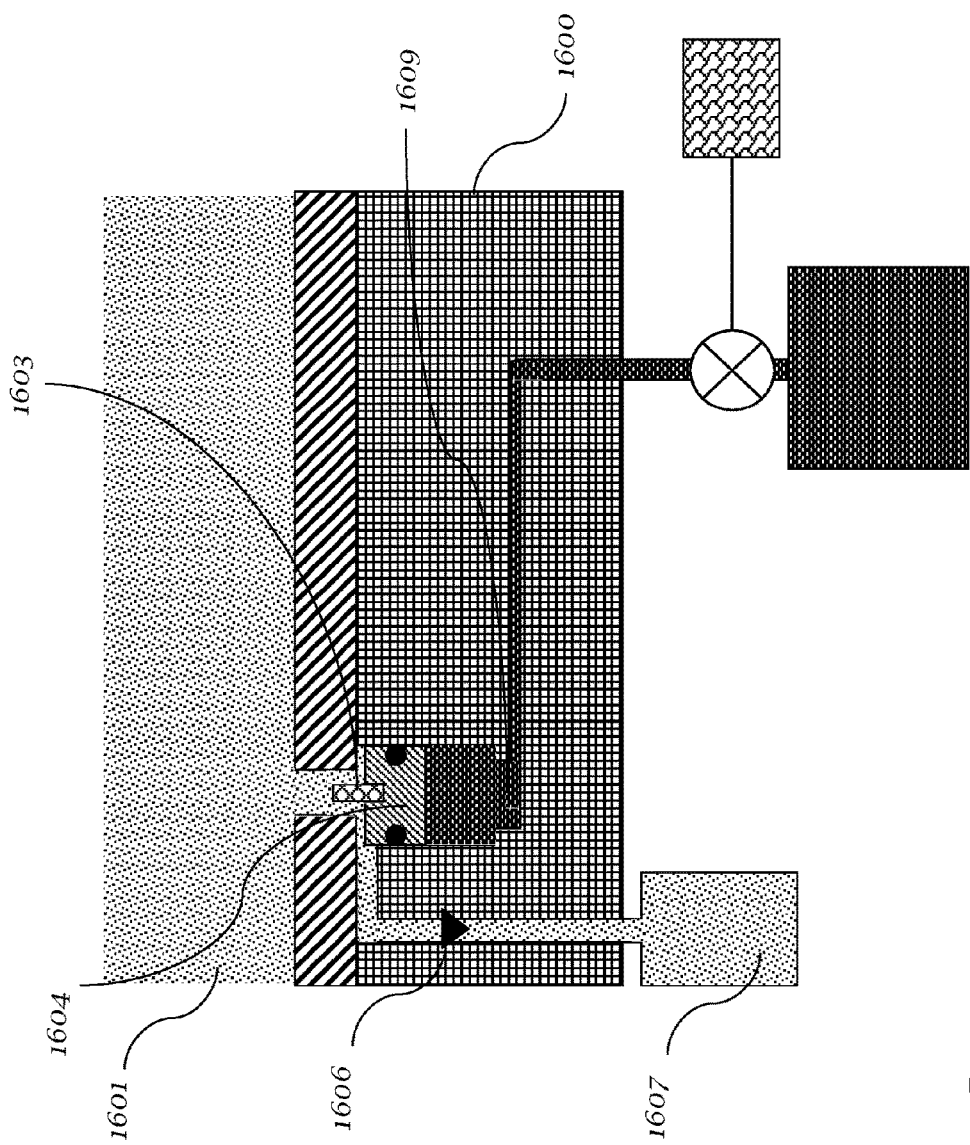
Fig. 16-B

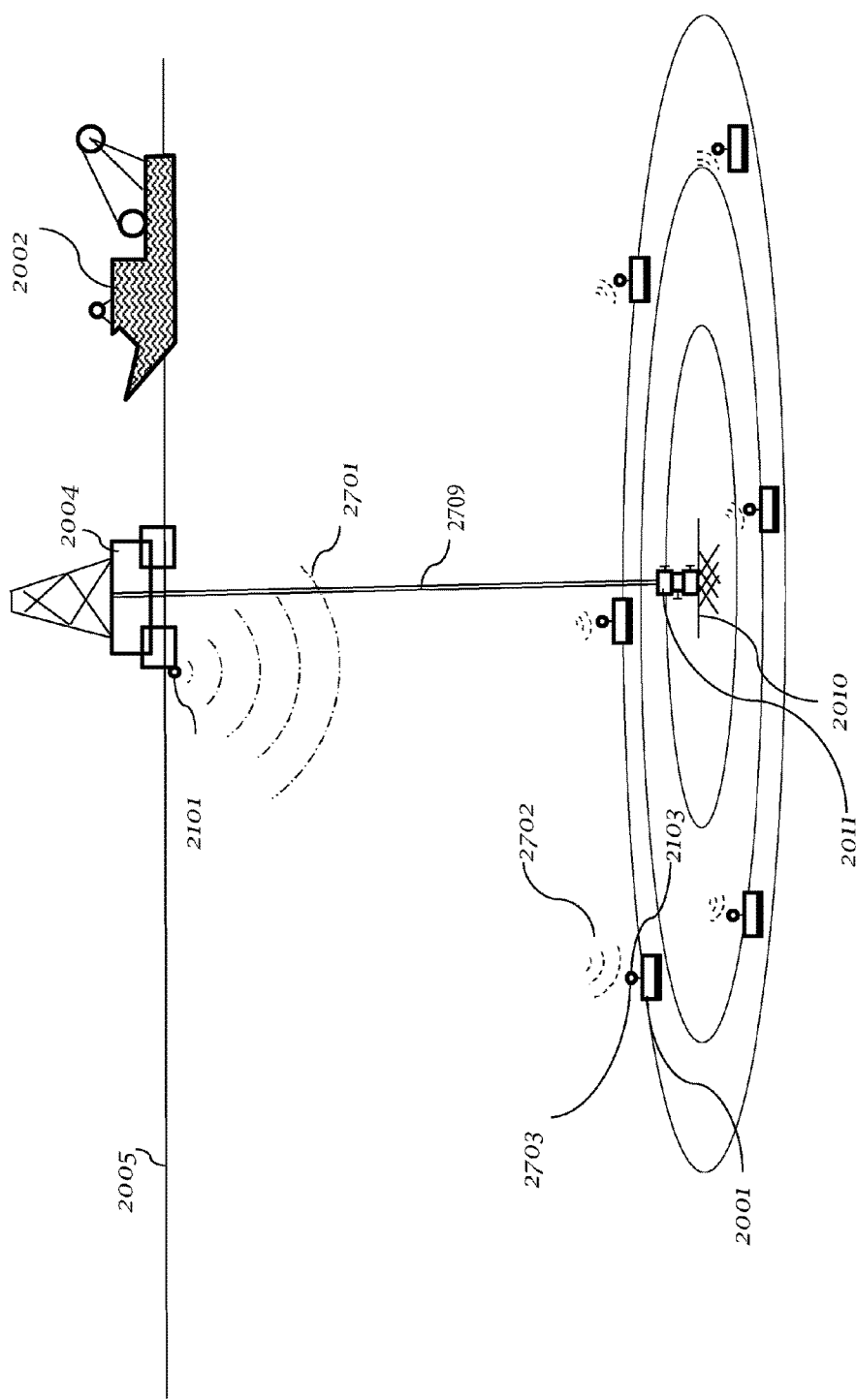
Fig. 27-A

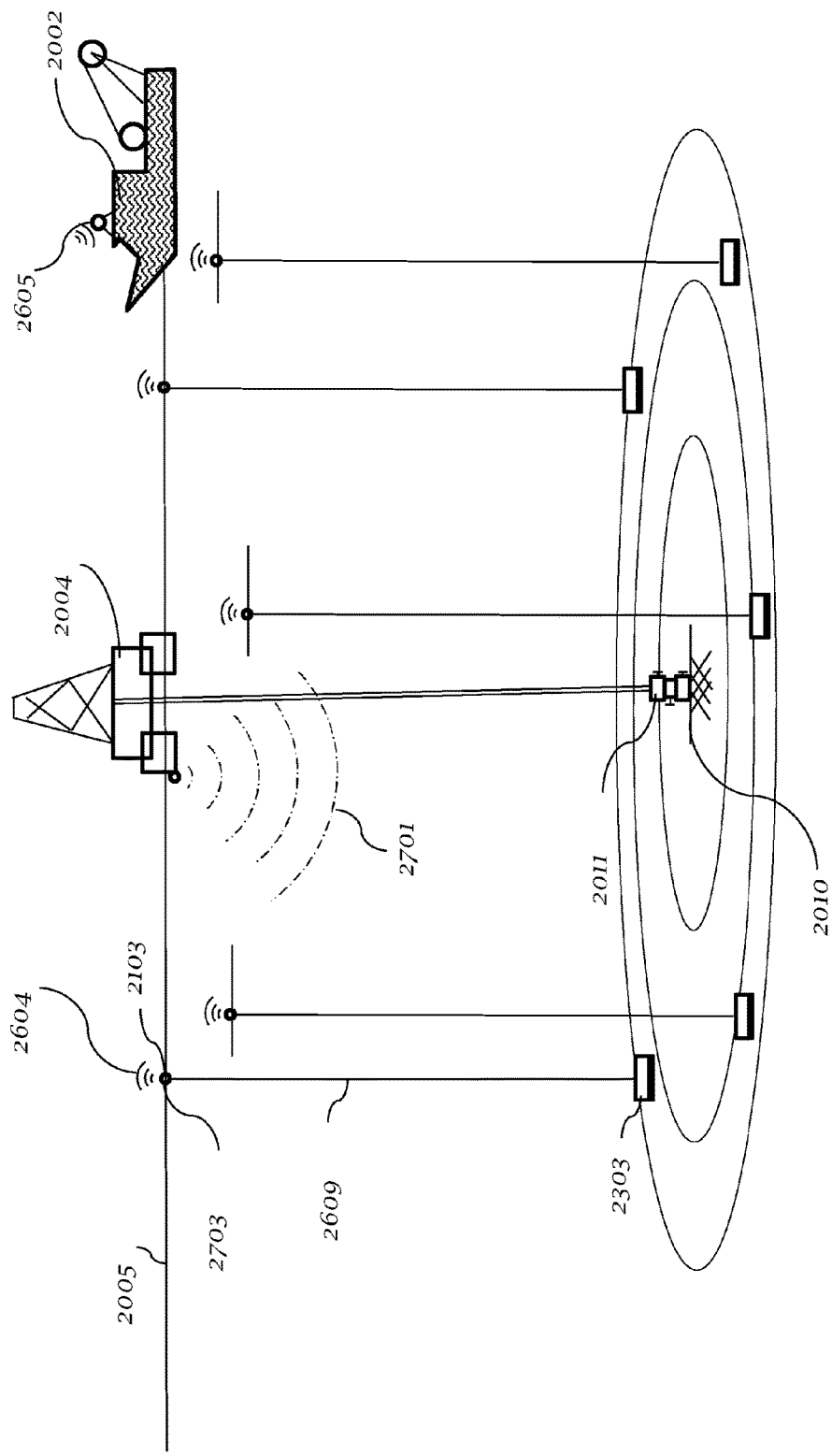
Fig. 27-B

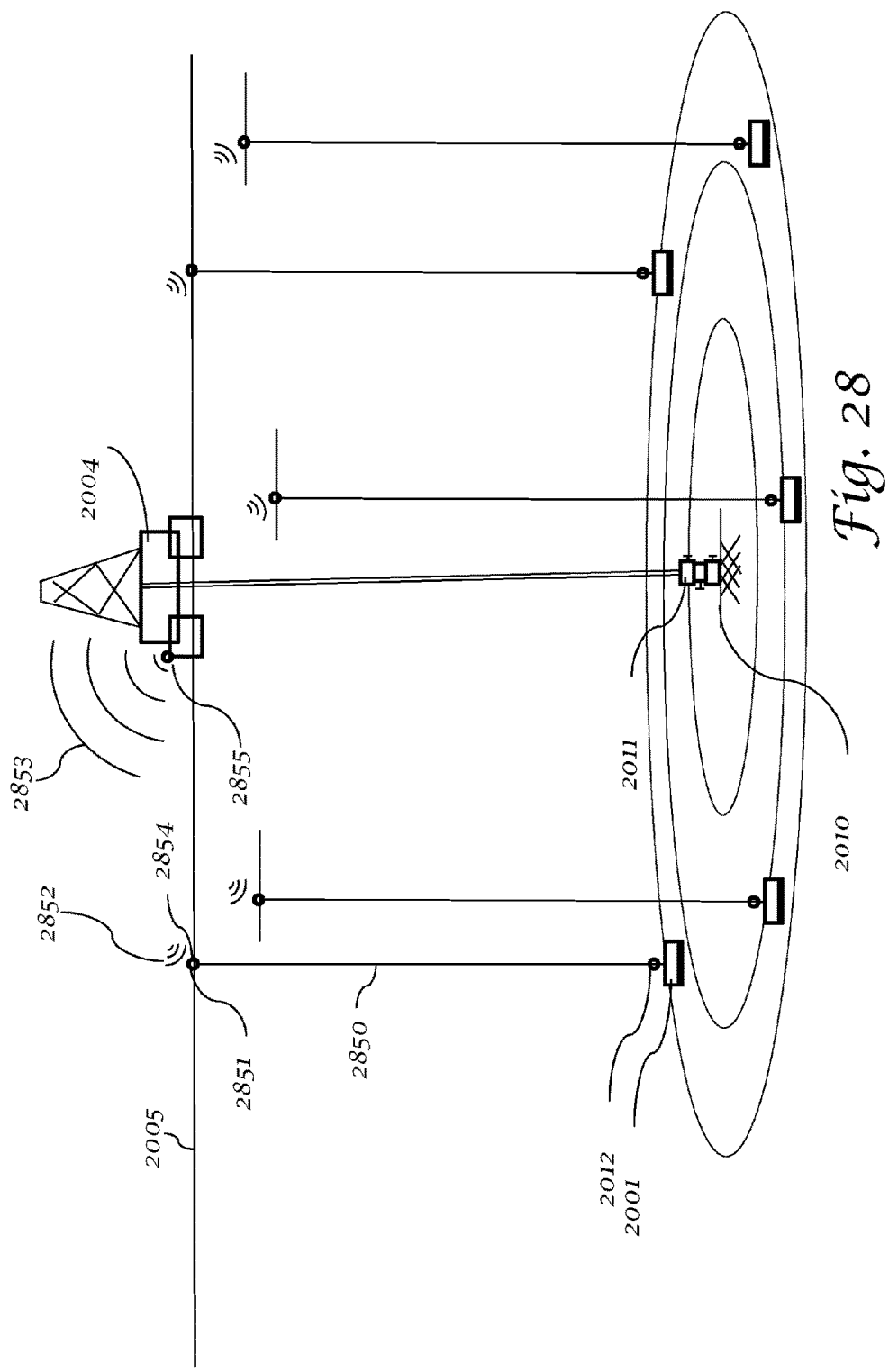

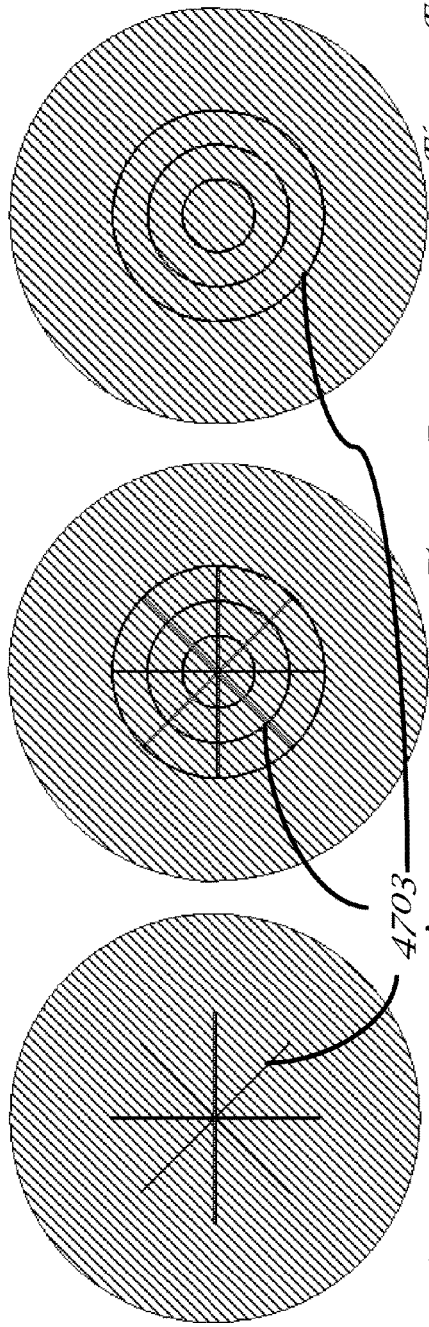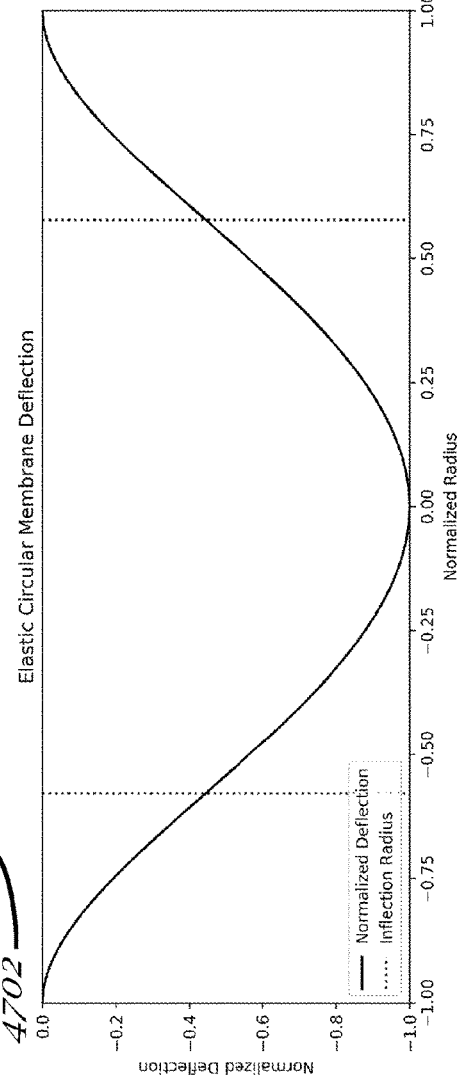

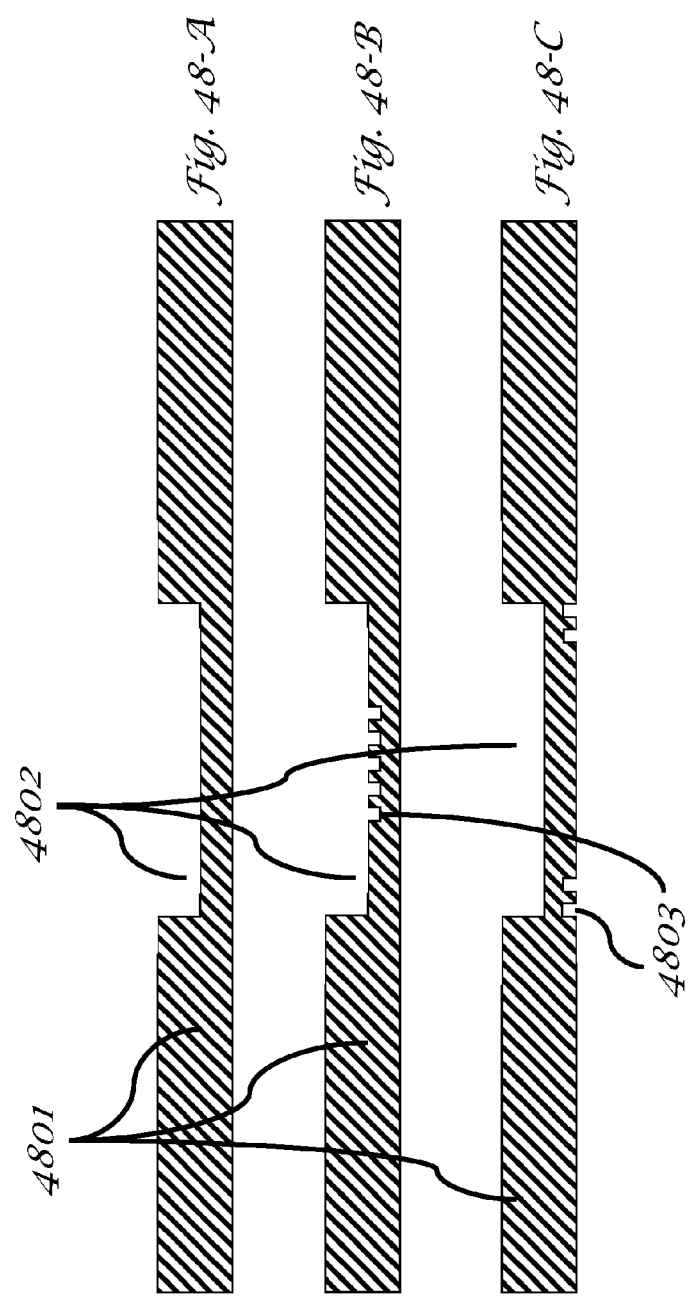

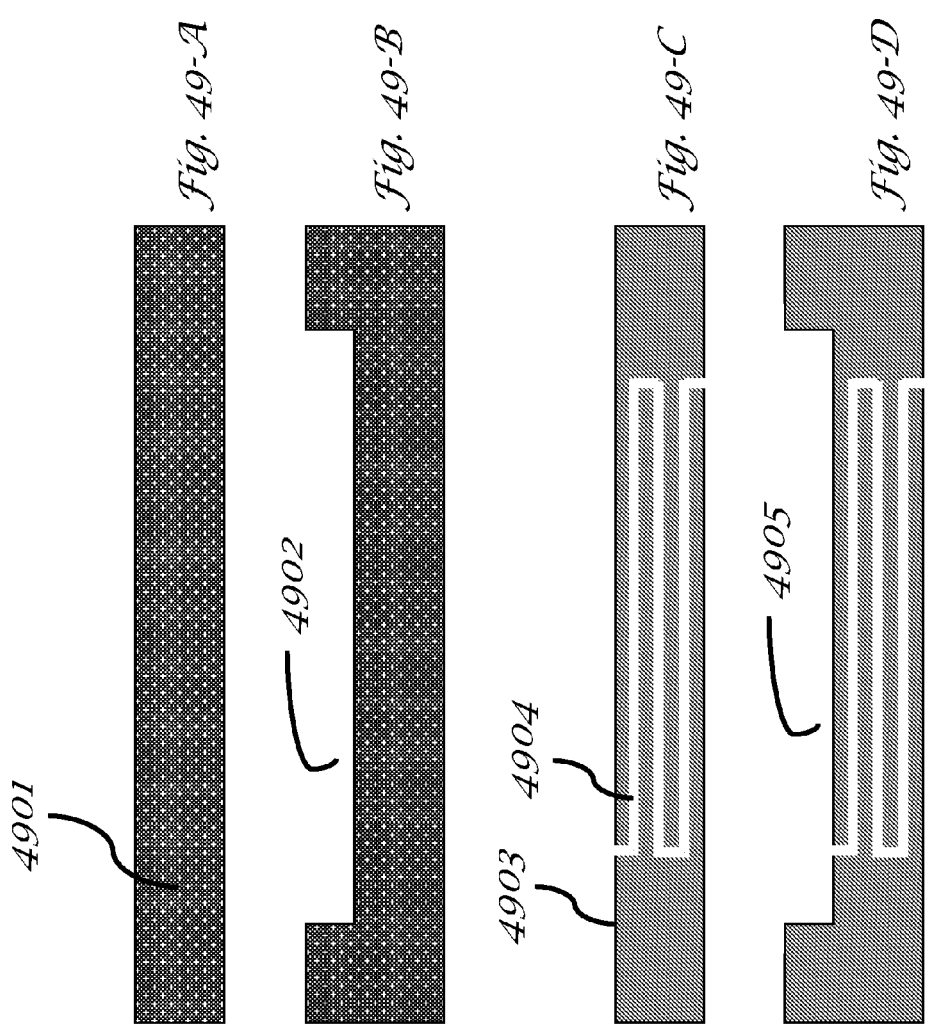

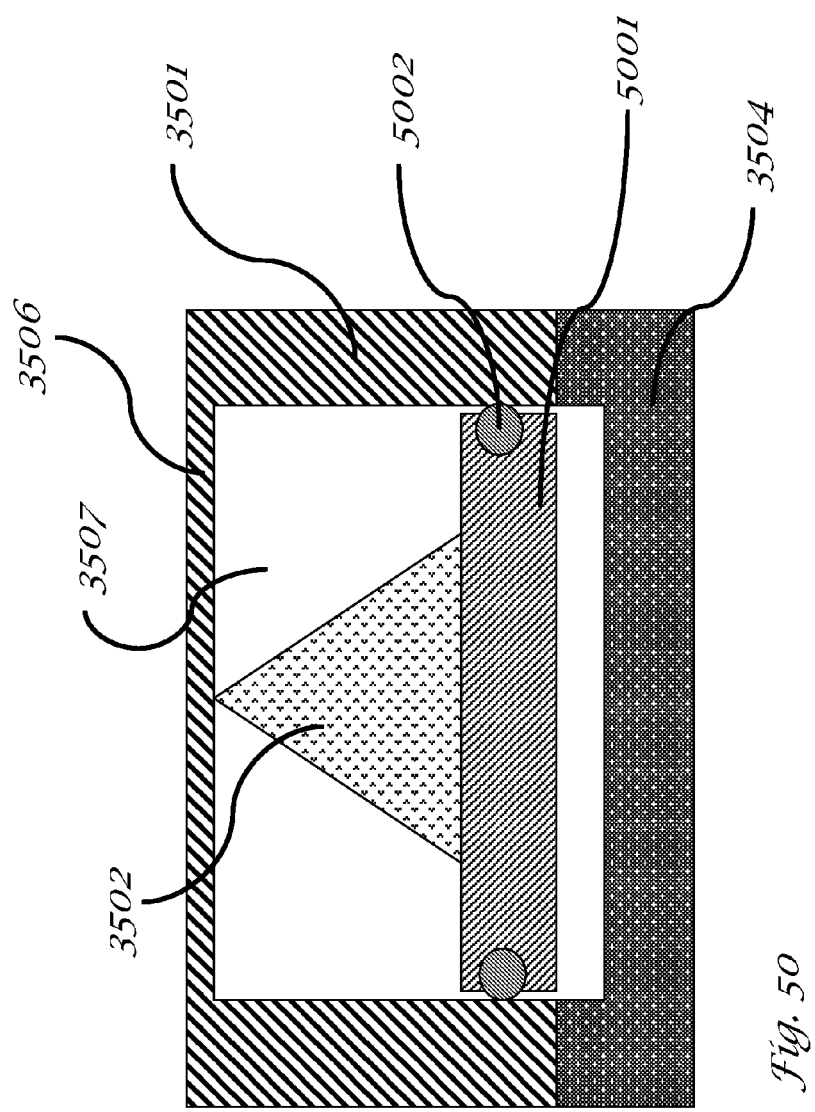

PASSIVE MICRO-VESSEL AND SENSOR

CROSS-REFERENCE TO RELATED APPLICATIONS

This application is a continuation in part of U.S. application Ser. No. 14/244,292, filed Apr. 3, 2014, entitled "Passive Micro-vessel and Sensor," which in turn is a continuation in part of U.S. application Ser. No. 13/760,879, filed Feb. 6, 2013, entitled "Passive Micro-vessel and Sensor," which in turn is a continuation in part of U.S. application Ser. No. 13/025,467, filed Feb. 11, 2011, entitled "Passive Micro-vessel and Sensor," which in turn claims priority from U.S. provisional patent application Ser. No. 61/337,998 filed Feb. 12, 2010, entitled "Passive Micro-vessel and Sensor." Each of the above-described applications is hereby incorporated herein by reference, in its entirety.

TECHNICAL FIELD

The present invention generally relates to an electrically passive device capable of communicating its position by acoustic emission at specific time intervals, and/or of retrieving and/or sensing/and/or determining characteristics of fluid samples at, for example, specific time intervals, and/or of time-release of particles, chemical products, or pharmaceutical products. More particular embodiments of the present invention relate, for example, to an electrically passive vessel for acquiring samples or releasing various particle/products in a subsurface formation (such as a geological or marine formation) or a living body, with the optional capability of providing measurements on the sample, and/or communicating its position via acoustic emissions.

BACKGROUND ART

Obtaining and analyzing samples of fluid from subsurface reservoir formations is often conducted during oil and gas exploration. Such operations are hindered by the harsh subterranean environment specific to oilfields, including high temperature and pressure (HPHT), corrosive fluids, and severely constrained geometry. The difficulty in acquiring and performing measurements on fluidic samples in such an environment are further complicated by use of electronic sensors that typically require power, monitoring and/or telemetry.

Several oil-field related operations, such as fracturing a geological formation, would greatly benefit from the capability of producing a map of the subterranean fracture geometry, and of the fracture evolution in time. Such capability does not currently exist. A similar need exists for a technology which can be used in monitoring and performing fracture analysis of subterranean carbon dioxide sequestration reservoirs.

Measurements of fluid properties and composition from an oil well are difficult to perform in the oilfield environment. The capability to inject very small sensing devices far into a geological formation by use of a Proppant or similar means of sensor transport, and to be able to determine their position and the precise moment when they perform a measurement or acquire a sample would greatly benefit the industry.

Measurements need to be performed in other types of situations, where the deployment of active sensing systems with on-board electronics and data transmission capabilities may either be impossible due to environmental issues (for example temperatures and pressures that are too high) or may prove to be too expensive to justify economically. Typical examples involve measurements within aquifers, potable water wells, or in a submarine environment. Such an environment may be a lake, or a sea or ocean. Still further environments include where or when there is a lack of power, such as in remote areas of the world.

The capability to perform viscosity measurements on fluid samples is extremely important in a variety of industries: chemical engineering, food industry, oilfield, to name a few. Usually this is accomplished using large laboratory instruments such as capillary viscometers and rheometers, or by using portable lighter weight instruments. In most cases, these instruments are operated using electrical power, and require sample manipulations that are difficult to automate. In some environments such instruments may be impractical due to their size (such as in difficult to reach areas, or within downhole oilfield tools), may be dangerous due to their electrical operation (inside explosive environments such as refinery facilities and tanks, near oil and gas wells), may be incompatible with the shocks or vibrations (within an oil well), or may be simply difficult to adapt. In this case new types of viscosity measurements need to be devised that avoid such inconveniences.

Samples often need to be acquired in explosive atmospheres (ATEX environments) such as inside refinery tanks (to determine the fluid quality and stratification), within refineries or gas plants or other facilities dealing with explosive environments. In such situations the sampling equipment should not pose a risk of generating an explosion, as would be the case if an electrical spark were created. All-mechanical systems that are ATEX-certified are currently used in the industry to perform this type of sampling.

Furthermore, samples may need to be acquired from fluids that are at high pressure, such as in a chemical factory, a refinery, inside an oil well, or at high depth within the ocean. When pressure is lowered, such samples may change (or degrade) by undergoing a thermodynamic phase transition leading to phase separation (i.e. gas may separate from oil, or asphaltenes may precipitate from heavy oil), in a possibly irreversible manner. Sample containers in this case may need to be filled slowly, at controlled inflow into the sample vial or chamber, in order to preserve the thermodynamic equilibrium and prevent, for example, a pressure shock that may lead to phase separation or other irreversible changes in the sample constituency. Such samples may also need to be maintained at high-pressure conditions subsequent to sample acquisition (for example during sample tool retrieval, or during transportation to a remote laboratory), to prevent sample degradation and maintain the sample characteristics unchanged.

Additionally, samples are often required in environments that pose objective risks and dangers, or that are physically remote, or where frequent sampling using manual devices may prove impractical: sites of nuclear disasters, military battlegrounds, biohazard or chemical hazard areas, terrorist attack sites, remote natural resources such as rivers and lakes, coastal waters and other offshore locations, deep water and sub-sea environments. In such cases, robotic equipment may need to be deployed, and the capability to take and analyze such samples may provide important information that cannot be acquired using the on-board in-line sensors present on such equipment. Such equipment may consist of autonomous or remotely-operated vehicles or robots; remotely-operated underwater vehicles; autonomous underwater vehicles such as buoyancy-driven gliders and wave gliders; airborne or ground drones; other type of robotic equipment.

Samples often need to be acquired and analyzed to detect trace levels of certain contaminants that may be too dilute to enable direct detection. Sample pre-concentration may be required in such cases, by methods such as filtration using mechanical filters, polymeric filters, fiber glass filters, affinity columns, solid phase extraction columns, gas chromatography pre-concentration tubes and columns, or other types of material showing particular affinity for the contaminant, and possibly included in porous or packed form. Particular care needs to be taken when acquiring such samples to prevent scavenging of the sample by, or its adsorption to, the materials of the sampling vial or chamber, or of the transport tubes. The filter material may need to be backflushed, often with a different solution, to remove filter cake buildup and to generate a pre-concentrated sample that may need to be stored into a separate vial or container for transport, storage, or for further manipulation and/or analysis. Alternatively, the filter itself may be retrieved and analyzed, after applying an optional extraction protocol, using laboratory equipment such as gas chromatography, high precision liquid chromatography (HPLC), mass spectroscopy, gamma ray spectroscopy, or other analytical chemistry, biochemical, biological, or nuclear equipment, and possibly after solvent or thermal desorption.

Often there is a need to perform a chemical or biochemical reaction on the acquired sample, by bringing it in contact with a known quantity of chemical or biochemical reagent that will lead to a property change as a consequence of the reaction. The chemical or biochemical reagent may be present as a liquid, solid, powder, gel, gas, emulsion or foam, and it may be attached to, or immobilized on, a solid substrate such as the walls of a vial, a strip of metal, tissue, plastic, paper (as is the case of colorimetric test strips). The reagent may be lyophilized. Often, the (bio)chemical reaction results in color change, which can be detected optically by spectrophotometric absorbance or by colorimetry. Other times direct fluorescence of the sample, or the presence of a fluorescent byproduct, can be detected by fluorescence measurements. Many other properties of the sample may be measured such as (without limitation) optical absorbance, chemiluminescence, color, turbidity, fluorescence intensity, index of refraction, conductivity, density, viscosity. In some cases the usage of a microplate with multiple wells may be necessary to prepare a sample and perform measurements on it.

Certain chemical or biochemical sample preparation protocols may require more complex sample manipulations, such as reaction with a first reagent, waiting for an incubation or reaction time, and then bringing the sample in contact with a second reagent. This sequence may need to be repeated several times.

For pollution monitoring, often samples are not acquired instantaneously but rather over longer periods of time. The rate of sample intake may be proportional to flow velocity in the body of water being sampled. This technique provides "integrated" water samples, which allow in some circumstances to determine the average pollution of the body of water over a period of time, rather than instantaneous pollution.

In certain applications, the moment when a sample needs to be acquired may not be known in advance, so that a pre-programmed sampling sequence may not be appropriate. In this case, individual control of the moment when each sample is performed may be required. For example, samples may need to be acquired in the aftermath of an unforeseen accident, or as directed by an external signal.

In some cases, there may be a need to acquire a larger number of samples than the capabilities of a single sampling device. In this case, multiple sampling devices may need to be used in a "daisy chain configuration", in such a way that once a device acquires its maximum number of samples, it automatically triggers the next device that will take over the sampling tasks. Using this approach, the total number of samples that can be acquired is not limited by the capabilities of an individual device.

Often there is a need for injecting, or liberating, small particles or small amounts of chemicals at predefined times into a remote environment, or into an environment which is difficult to access. Such small particles or chemicals may be used as tracers, may participate in chemical reactions, or may be used as pharmaceuticals. Exemplary environments where such particles, chemicals, or pharmaceuticals may be injected include without limitation oil and water reservoirs, pre-existing or induced fractures within such reservoirs or within other geological formations, oil, water and/or gas wells, water bodies such as lakes, rivers and oceans, or a human body. It may be desired that such particles or chemicals react in an aggressive way with the fluid present in the remote environment, for example by producing an explosion or producing a rapid release of energy Monitoring of hazardous waste disposal reservoirs and of adjacent aquifers for contamination mapping and leaching is also a very important domain, where the need for miniaturized and economical sensing solutions is prominent.

Unintended leaks, spills or discharges occur frequently around industrial sites, and may affect environments such as the deep ocean (off-shore environment), a river, a lake, an estuary, the coastal water, or the atmosphere. In the case of an event concerning an unintended discharge, leak, nuclear or chemical spill from an industrial site or other facility, there is an inherent desire within the industry to understand the impacts of that event on the environment. In addition, it would be desirable to be able to gather accurate data concerning the distribution and movement of the pollution over time as it passes through the environment.

There are many factors that may affect the complex interaction of a leak into a marine environment, including ocean currents, wind, waves, thermoclines, buoyancy, pressure, formation of gas hydrates and phase transitions just to name a few. In order to make the best possible predictions using 3 dimensional models (in space) and 4 dimensional models (over time) as an off-shore leak progresses, real data points are required to be entered into the models. Samples taken at different points and different times around the spill area are a valuable method for determining the progression of a spill through the environment. However, technology today is very limited in terms of deployment and ability to acquire a significant number of samples at multiple depth points, at multiple radial points from the source and at multiple points in time. Sample acquisition systems may need to be deployed in a way that is non-intrusive to the normal operations in and around the industrial facility (which may be a drilling rig, an off-shore platform, a ship, a tanker, a pipe etc.), both on the ocean surface and in the subsea. In the early hours and days after an event occurs, resources are normally dedicated to critical tasks other than environmental monitoring or sampling. Additionally, in most cases, the sampling capability is also not located at the industrial site, but more likely on-shore and may take days for the equipment to reach the offshore facility. There is a need for a system that is put in place around an industrial facility as a precautionary measure at an early stage in the project. Furthermore, the position of the system should be accurately determined at the time of installation. Acquired samples and subsea systems also need to be easily retrievable by an ocean vessel at the ocean surface.

In the case that a sampling system is placed in the marine environment for an extended period of time, biofouling and biogrowth tends to develop on the system, including at the sampling intake ports. Similarly, in a deep-water environment near hydrocarbon production facilities, there is a risk of methane hydrate formation. This provides a serious risk of blockage, contamination and/or unrepresentative sampling. Thus the need for a system that is able to not only remain in standby mode ready for deployment, but also be in a protected environment that rejects any biogrowth or methane hydrate from forming during the standby period.

Often there are cases where a sampling unit or an array of sampling units needs to be deployed in a non-static environment, such as when there is a natural ocean current or wave motion due to winds, or other movement within the water column. This movement may, or may not, be in the same direction at all times, may not be predictable, and may cause the sampling unit or string of units to be in a position that is not vertically above the original anchoring point, or vertically below a buoy or similar water-surface mooring point. Consequently, this may cause error in the assumed position data associated with the sampling unit or array.

Currently, sample loading and measurement protocols for microbiological measurements often need to be performed manually, requiring specialized labor and equipment and incurring significant costs. In addition, such measurements require the collection of a representative sample from the environment being monitored (that may be a lake, a river, a pool, a reservoir, a groundwater well, an estuary, coastal water, drinking water, wastewater on any other water source), and transportation to a specialized laboratory where the measurements are performed. This protocol provides a risk of human error in the sampling and/or transportation procedure, leading to an unrepresentative sample being collected, or to sample contamination and/or degradation during transport. There is a need therefore for a device that is capable to perform the sampling and analysis operation in-situ, in a repeatable and reproducible manner, thus bypassing certain human intervention steps that are prone to creating errors.

In certain applications, there is a need for very precisely controlling the moment when each sample is being acquired in a series of sampling operations. These moments may depend of certain external events that cannot be predicted or anticipated at sampler installation, and therefore the sample acquisition moments cannot be pre-programmed in the sampler design.

A sampler may also require a means to actuate the sampling mechanism in a rapid manner upon the receipt of the signal to sample following external trigger activation, such as in the seconds or milliseconds following the receipt of the signal. Furthermore, a sampling device may require means for confirming that a sample was actually acquired, for recording the exact time when each sample was acquired (also known as a timestamp), as well as a certain amount of information corresponding to the sampling process, such as the total duration over which a sample container was filled, the total amount that was sampled etc.

It is important that any timing mechanism used to trigger the acquisition of a fluid sample be accurate, however in certain applications such timing may not prove accurate enough. For example, timing errors in fluidic clocks may occur due to small manufacturing imperfections that may change the overall timing of the sample acquisition. For example, a ten percent relative error in the volume of a timing cavity will result in a ten percent relative error in the timing of that particular sample acquisition. If the overall timing was designed to be ten hours, a ten percent error will introduce a one-hour absolute error in the timing, so the sample may be acquired an hour prior to, or an hour later than the scheduled time.

Such timing errors provided by fluidic clocks may become particularly problematic when a series of samples needs to be acquired in sequence. For example, assume one sample needs to be acquired every hour for a period of twenty four hours. Twenty four sampling devices are deployed at $t=0$, device numbered n ($1<n<24$) having a time constant of n hours prior to triggering the acquisition of its corresponding sample. If there is a ten percent error in the fluidic clock of each sampling device, that means that it is likely that the order of the sampling events will be disturbed. For example, the 10th device may acquire its sample at $t=11$ h, and the 11th device at $t=10$ h, thus they will be out of order.

SUMMARY OF THE INVENTION

In accordance with an embodiment of the invention, a system may include one or more sampling devices, each device including at least one sampling mechanism. Each sampling mechanism includes a timing diaphragm, a timing cavity, a mechanical structure and an isolated cavity. Each of these parts may be built on a single physical substrate, or may be separate parts that are connected together by tubes, pipes, o-ring or gasket joints, or other types of mechanical or fluidic fixtures known to the person skilled in the art. Each sampling mechanism further includes a conduit that may be a microfluidic channel or a capillary tube, and that may have a predefined geometry. Upon applying pressure to a timing fluid within the conduit, said timing fluid being a liquid or a gas, the timing fluid advances within the microfluidic channel at a speed, for example, that may be dictated by the applied pressure, the predefined channel geometry and/or known timing fluid properties. Upon reaching the timing cavity and filling it after a timing interval, the timing fluid applies pressure to the timing diaphragm which ruptures and/or collapses the mechanical structure, thus allowing the external fluid to enter the isolated cavity, which may then further lead to a sampling chamber. The isolated cavity and the sampling chamber may be part of the same assembly as the sampling mechanisms, or they may be separate parts that are connected using some form of fluidic or mechanical fixture known to the person skilled in the art. The timing diaphragm's movement may be partially restricted by using any type of mechanical system known to the person skilled in the art, such as, without limitation, a mechanical stop, a spring, a boss, a support or any combination thereof. Such restriction may protect the timing diaphragm from breaking under the effect of one, or both, of timing fluid pressure and external fluid pressure.

In accordance with related embodiments of the invention, the sampling mechanism may include, in the place of the timing diaphragm, a piston that may be, for example, configured to move within the isolated cavity upon applying pressure to one side of the piston. The sampling mechanism may further include a conduit that may be a microfluidic channel or a capillary tube, and that may have a predefined geometry. Upon applying pressure to a timing fluid (liquid or gas) within the conduit, said timing fluid advances within the microfluidic channel at a speed, for example, that may be dictated by the applied pressure, the predefined channel geometry and known timing fluid properties. Upon reaching the timing cavity and filling it after a timing interval, the timing fluid applies pressure to one side of the piston, which advances within a piston cavity and, upon reaching the mechanical structure, applies mechanical stress to the mechanical structure causing it to rupture and/or collapse, thus allowing the external fluid to enter the isolated cavity, which may then further lead to a sampling chamber. The piston may include a piercing structure, which may, for example, be a protrusion that concentrates the stress applied to the mechanical structure. Such protrusion may be a needle, a pin, a raised boss, or any other type of structure known in the art, and it may be separate from the piston or an integral part of it. The isolated cavity and the sampling chamber may be part of the same assembly as the sampling mechanisms, or they may be separate parts that are connected using some form of fluidic or mechanical fixture known to the person skilled in the art.

In accordance with further related embodiments of the invention, the combination of channel geometry, timing cavity volume, applied timing fluid pressure and timing fluid properties may be chosen such that the timing fluid advances within the channel at a speed that will assure filling of the timing cavity in a time interval that falls within a time range of interest for the given application. Said time range of interest may be, without limitation, depending on the given application, less than 100 milliseconds, between 0.1 milliseconds and 10 milliseconds, or between 10 millisecond and 1 second, or between 1 seconds and 100 seconds, or of longer or shorter duration. That range of interest may extend to many days, weeks and months.

In accordance with related embodiments of the invention, the mechanical structure may be made of an inorganic material, a non-polymeric material, silicon, glass, ceramic and combinations thereof. The mechanical structure may be insoluble in water, bodily fluids, oil, crude oil, oil field fluid, salt water, sea water and combinations thereof. The conduit may be, without limitation, initially at least partially filled the timing fluid, or in other embodiments, the timing fluid may be the external fluid that enters from the isolated cavity. The device may include a plurality of sampling mechanisms. At least one sampling mechanism may have a conduit having different dimensions than another sampling mechanism, and/or a timing cavity of different volume from another timing mechanism, such that the timing fluid of the different sampling mechanisms reach and fill their associated timing cavities at different times. The sampling mechanism may include a check valve that allows flow of fluid into the sampling chamber but prevents flow of fluid out of the sampling chamber. The device may release a weight upon sample acquisition so as to maintain a constant mass and not modify its submerged weight and buoyancy.

In accordance with related embodiments of the invention, the sampling chamber may include a compressed spring and a piston, one side of the piston in contact with the sampling chamber and the other side in contact with the external fluid, such that prior to sampling being initiated the spring is compressed by the piston due to external fluid pressure being applied to the piston, and upon sampling being initiated, the hydrostatic pressure on both sides of the piston equalizes and the elastic force of the spring displaces the piston, thus acquiring a sample at controlled speed and with minimal change to the overall submerged weight and buoyancy of the device. The travel of the piston may be restricted due to the presence of a mechanical fixture such as a stop or a ridge.

In accordance with further related embodiments of the invention, a conduit, such as a microfluidic channel or capillary tube, may be implemented between the mechanical structure and the sampling chamber, or within the sample chamber itself, such that upon the collapse of rupture of the mechanical structure, the sample enters the sampling chamber at a low flow rate controlled by the conduit, and fills the sampling chamber over a controlled period of time.

In accordance with yet further related embodiments of the invention, the device may force the sample to come in contact, upon or prior to entering the sampling chamber, with a filter that may be one of the following (without limitation): a mechanical filter, a solid phase extraction column, a hydrocarbon filter, a gas chromatography preconcentrator, a filter to collect and concentrate radioactive material, a biological filter, an absorbent medium, a scavenging medium, a hydrophobic material, and hydrophilic material, or any combination thereof. The filters may, optionally, be later retrieved and analyzed, to provide time-series data concerning the contaminant of interest at the location of the device.

In accordance with further related embodiments of the invention, an acoustic signal may be emitted from the device upon the mechanical structure rupturing and/or collapsing. The isolated cavity and the mechanical structure may be shaped to emit a predetermined acoustic signal upon the mechanical structure collapsing. The device may include a plurality of sampling mechanisms, each sampling mechanism having an acoustic signature upon collapse of its associated mechanical structure, wherein the acoustic signatures of the sampling mechanisms vary. The device may include a plurality of sampling mechanisms, wherein at least one sampling mechanism has a conduit, such as a microfluidic channel or capillary tube, having different dimensions than another sampling mechanism, such that the timing fluid of the different sampling mechanisms reach their associated cavities at different times so as to produce multiple acoustic events that occur at different times. The sampling chamber may include a sensor element for performing a detection and/or a measurement on the fluid. The sensor element may include, for example, a material that interacts with the fluid and/or electrodes allowing an electrochemical measurement to be performed on the fluid sample. The device may be electrically passive. The isolated cavity may include a micro-particle, a nano-particle, a chemical product, and/or a pharmaceutical product, which is released into the environment after the collapse and/or rupture of the mechanical structure separating the isolated cavity from the exterior environment. The chemical in question may react in an aggressive way with the environment, such as by generating an explosion or some other form of rapid energy release. The device may include a filter and/or a sieve to retain broken mechanical structure parts from entering at least one of the isolated cavity and the environment surrounding the device.

In accordance with still further related embodiments of the invention, the system may include a sampling chamber for receiving fluid from the isolated cavity, the sampling chamber partially pre-filled with a culture medium that allows select classes of microorganisms to develop and grow, such that once a sample is acquired, the sample comes in contact with the culture medium. If the sample is contaminated with the select classes of microorganisms, these will multiply, over an incubation period, due to the presence of the culture medium. The sampling chamber may further include a temperature control mechanism that ensures that the sample temperature is maintained within a range that is optimal for sample incubation. The sampling chamber may further include chemical and/or biological reagents allowing the detection of the presence and/or of the quantity of said microorganisms. Such detection may be performed optically, for example by monitoring the color of the sample via an optical absorption measurement, or by monitoring its fluorescence.

In accordance with yet further related embodiments of the invention, communications may be provided with a sampling device or a system of multiple sampling devices by means of a wired or wireless link, so as to remotely trigger the beginning of one or multiple sample acquisition operations. Examples of such means of communication include a mechanical, acoustical, electrical or electromagnetic wired or wireless link, for example, and without limitation, a mechanical cable or lever, a serial communication cable, a parallel communication cable, an electrical triggering cable, an electromagnetic wave using a mobile telephony network or a radio frequency or satellite connection, a pressure wave such as an acoustic or sound wave using an acoustic module (such as sonar and/or a hydrophone, a speaker and a microphone, or similar), a wi-fi or Bluetooth connection, an optical signal such as a laser signal, or any other form of acoustic, electrical, electromagnetic, acoustic or mechanical communication means and/or trigger known to the person skilled in the art.

In accordance with another related embodiment of this invention, a sampling device may be provided that may be remotely triggered. The sampling device may include a passive timing mechanism with a short time constant that allows, such that upon receipt of the trigger signal, a sample can be acquired within a relatively short time interval. Such a passive timing mechanism may combine appropriately-sized timing cavity and timing channel, a timing fluid of appropriate viscosity and a timing fluid pressure of appropriate magnitude, to result in a short timing interval prior to breaking the associated mechanical structure. Such a time interval may be less than 100 ms. In various applications, the time interval may range from 0.1 ms to 10 ms or 10 ms to 1 s In other time applications the required timing may be significantly longer.

In accordance with still further related embodiments of the invention, a monitoring system is provided for monitoring the sampling acquisition process, and, without limitation, to record a time-stamp, allowing precise recording of sample acquisition time by the sampling device.

The monitoring may be achieved by using a pressure measurement performed inside the sample chamber, as triggered by a processor or at predefined times, preferably in a periodic manner. Optionally, a second pressure measurement may be performed to monitor the pressure of the external medium. Pressure sensors may be in communication with a processor that can process their data and record it in a memory module, and/or transmit it to an external data recording system using a wired or wireless connection. The timestamp of the sample acquisition ($t_{ramp}$) may be inferred by monitoring the sample chamber pressure sensor for a significant deviation from the initial pressure in the sample chamber ($p_{ini}$). In various embodiments, the sample chamber may include a pressure switch that activates once the pressure inside the chamber increases past a given threshold. The moment of the activation of the pressure switch corresponds to the timestamp of the sample, $t_{samp}$. This timestamp may be recorded by the monitoring system. In various embodiments of the invention, the pressure curve recorded from the pressure sensor inside the sample chamber may be used to determine a sample fill-up duration $\Delta t$ by recording the time $t_{fill}$ when pressure stabilizes within the sample chamber, and subtracting from this value the time corresponding to beginning of the sample acquisition $t_{samp}$: $\Delta t = t_{fill} - t_{samp}$. In various embodiments, the value $p_{ini}$ of the initial pressure in the sample chamber prior to sample acquisition, the value $p_{fin}$ at which pressure has stabilized in the sample chamber after the sample acquisition, and $p_{ext}$, the pressure measured by the sensor monitoring the pressure of the external medium, may be used to determine the total volume of the sample acquired.

In accordance with further related embodiment of the invention, the sample chamber may include optical elements for monitoring and performing a measurement of, without limitation, turbidity, absorbance, color, transmittance, autofluorescence, or fluorescence, or any combinations thereof. The sample chamber may incorporate certain optical components, either inside the sample container or in its proximity, in order to assure that the light travels across or around, or otherwise interacts with the sample in an optimal way. The sample chamber may be equipped with, for example: one or several optical windows allowing an optical measurement to be performed on the sample contained within the sample chamber, one or multiple light sources, optical detectors, sensors or recording devices (such as, without limitation cameras, individual photodiodes or arrays thereof, other types of optical sensors, phototransistors, avalanche photodiodes, photomultipliers), mechanical positioning assemblies, fibers, diaphragms, mirrors, optically absorbing surfaces, optical filters of all kinds (such as, without limitation neutral filters, band-pass filters, low-pass filters, high-pass filters, dichroic filters) or any other type of optical component or device known to the person skilled in the art, or any combination or configuration thereof.

In another embodiment of the invention, the exact time of the sample acquisition (its timestamp) is measured optically, by monitoring a change in the optical properties of the sample chamber. Said monitoring may include an absorbance measurement performed on the acquired sample at a wavelength where the sample fluid absorbs light (such that the measured absorbance will be higher after sample acquisition than prior to it). Alternatively, the monitoring may involve an optical signal (or lack thereof) related to the deviation of the light path due to the change in optical refraction index caused by the sample acquisition within the sample chamber.

Any other type of measurement, optical or not, that is known to the person skilled in the art, may be used to determine whether a sample has been acquired within the sample chamber. This may include a conductivity measurement, a temperature measurement, an electrochemical measurement, an optical measurement, a physical measurement, a force measurement, a deflection measurement, a chemical measurement, a biological or biochemical measurement, or any combination thereof.

In accordance with further related embodiments of the invention, a passive timing mechanism of improved precision is described, involving a sampling device that includes multiple sampling mechanisms capable of timing and performing the acquisition of multiple (n) samples in an electrically-passive way, whereas the electrically-passive timing mechanism corresponding to sample i+1 is triggered at a time instant that is related to the time of acquisition of sample i. More particularly, at least one of the one or more devices includes a first sampling mechanism and a second sampling mechanism, wherein the piercing of the mechanical structure and acquisition of a sample by the first sampling mechanism acts as a trigger for activating the timing mechanism of the second sampling mechanism.

In accordance with yet further related embodiment of the invention, a sampling device may include two sampling mechanisms such that there are, without limitation, two timing diaphragms (or, for example, two pistons), two connected timing cavities, two mechanical structures and two isolated cavities. The first mechanical structure separates an external fluid from the first isolated cavity. Each sampling mechanism further includes a conduit that may be a microfluidic channel or a capillary tube, and that may have a predefined geometry. Upon applying pressure to a timing fluid within the conduit, said timing fluid being a liquid or a gas, the timing fluid advances within the microfluidic channel at a speed, for example, that may be dictated by the applied pressure, the predefined channel geometry and known timing fluid properties. The timing fluid conduit is also connected, by a tube or similar fluidic connection, to the second mechanical structure. Upon reaching the connected timing cavities and filling them after a timing interval, the timing fluid applies pressure to the two timing diaphragms simultaneously, thus destroying their corresponding mechanical structures, e.g. by rupturing and/or collapsing them. The first mechanical structure, once destroyed, allows a sample of the external fluid to be acquired by enabling the external fluid to enter the isolated cavity, which may then further lead to a sampling chamber. The second mechanical structure, once destroyed, opens a passage for the timing fluid to enter the timing fluid conduit of a subsequent sampling mechanism, thus acting as an effective trigger for timing the acquisition of the next sample.

In accordance with still further related embodiments, a tool may incorporate the above-described device. The tool may have an interior flow-line through which a sample fluid is capable of circulating and in which the one or more devices are positioned, wherein said sample fluid when circulating in the interior flow-line contacts the devices. The tool may include a pad capable of being pushed into a formation wall to receive fluid, and a pump for pumping formation fluid into the interior flow-line. The tool may further include at least one microphone for receiving acoustic emissions from the one or more devices. Other microphones may be located at different positions on the ground in the area surrounding a well, or within wells drilled elsewhere in the formation. The tool may include a processor for performing a time-stamping of the received acoustic emissions and/or a determination of device positioning. The tool may include a retrieval mechanism for retrieving the devices from an underground formation. The retrieval mechanism may include one of a pumping device and a suction device.

In accordance with still further related embodiments, the above-described device may be injected from the surface into an underground formation by pumping it along with a carrier fluid or proppant through a well. Monitoring of the acoustic emissions from the device may be performed using microphones placed in the injection well, in a well drilled elsewhere in the area, or on the ground. The device may be deployed in a pipe, a well, an engine, a hydrocarbon reservoir, an aquifer, a body of water, an oil field tool, a waste disposal reservoir, a proppant formulation and/or a living body.

In accordance with another embodiment of the invention, a device for sampling a fluid includes at least one sampling mechanism, which may be electrically passive. Each sampling mechanism includes an isolated cavity, a mechanical structure and a microfluidic timing mechanism. Upon the microfluidic timing mechanism being subject to pressure, the mechanical structure collapses and/or punctures and/or ruptures after a time delay, allowing external fluid to enter the isolated cavity, which may then further lead to a sampling chamber.

In accordance with related embodiments of the invention, the microfluidic timing mechanism may include a conduit that may be a microfluidic channel or a capillary tube, and that may have a predefined geometry. Upon applying pressure to a timing fluid within the conduit, the timing fluid advances within the conduit at a speed, for example, that may be dictated by the predefined channel geometry and known timing fluid properties The microfluidic timing mechanism may include a timing cavity and a timing diaphragm, and wherein upon the timing fluid advancing and reaching/filling the timing cavity, the timing fluid applies pressure to expand the timing diaphragm, collapsing the mechanical structure and thus allowing the external fluid to enter the isolated cavity. The sample cavity may include a sensor element for performing a detection and/or a measurement on the fluid that enters the sample chamber. The isolated cavity may include a micro-particle, a nano-particle, a chemical product, and/or a pharmaceutical product, which is released into the environment after the collapse and/or rupture of the mechanical structure separating the isolated cavity from the exterior environment. The device may emit a predetermined acoustic signal upon collapse of the mechanical structure, or upon the reaction of the content of the cavity with the external environment. Such reaction may be designed to be aggressive, such as an explosion. The device may include a filter and/or a sieve to retain broken mechanical structure parts from entering at least one of the isolated cavity and the environment surrounding the device.

In accordance with further related embodiments of the invention, a system includes one or more of the above-described devices. The system further includes at least one microphone, geophone, seismometer, accelerometer and/or other type of sensor for receiving acoustic emissions from the one or more devices. A processor may timestamp the received acoustic emissions and/or determine a position of the one or more devices based, at least in part, on the received acoustic emissions. The device may be deployed within a pipe, a well, an engine, a hydrocarbon reservoir, an aquifer, a body of water, an oil field tool, a waste disposal reservoir, a proppant formulation and/or a living body.

In accordance with another embodiment of the invention, a system for sampling a fluid includes at least one device, which may be electrically passive. Each device includes a mechanical structure, and a microfluidic timing mechanism that, upon the microfluidic timing mechanism being subjected to pressure, collapses the mechanical structure after a time delay. Upon collapse the mechanical structure emits an acoustic signature, and may allow fluid to enter a sample chamber. The system further includes a microphone for receiving the acoustic signature, and a processor operatively coupled to the microphone. The processor may, for example, extract the position of the device based, at least in part, on the received acoustic signature.

In accordance with another embodiment of the invention, a method includes deploying a device in a fluid. An acoustic cavity within the device is opened to the fluid at a time determined by an electrically passive timing mechanism. The device emits an acoustic signature when the cavity is opened.

In accordance with related embodiments of the invention, a sample may be acquired upon opening of the cavity. The acoustic signature may be detected using, at least in part, one or more microphones, geophone, accelerometer and/or other type of sensor. The detected acoustic signature may be time-stamped. The position of the device may be extracted from the detected acoustic signature using, without limitation, triangulation, compressional signal processing, and/or shear signal processing. The device may be deployed in a geological formation or a formation fracture. For example, the device may be pumped into the geological formation. Deploying the device may include using the device in a hydraulic fracturing operation. The device may be deployed in a fluid within a pipe, a fluid within a well, a fluid within an engine, a hydrocarbon reservoir, an aquifer, a body of water, a fluid within an oil field tool, a waste disposal reservoir, a proppant formulation and/or a living body.

In accordance with further related embodiments of the invention, the timing mechanism may include a timing diaphragm or a piston, a timing cavity, and a conduit that may be a microfluidic channel or a capillary tube, and that may have a predefined geometry. Upon applying pressure to a timing fluid within the conduit, the timing fluid advances within the microfluidic channel at a speed, for example, that may be dictated by the predefined channel geometry and known timing fluid properties. Upon reaching and filling the timing cavity after a timing interval, the timing fluid applies pressure to the timing diaphragm or piston which opens the acoustic cavity within the device to the external fluid. The conduit may be, without limitation, initially at least partially filled with the timing fluid. In other embodiments, the timing fluid may be, without limitation, the external fluid that enters from the isolated cavity.

In accordance with still further embodiments of the invention, at least one of a micro-particle, a nano-particle, a chemical product, a material, and a pharmaceutical product may be stored within the device and released into the external fluid upon collapse of the acoustic cavity. The particles, product or material that is released may react aggressively with the environment, thus generating a further acoustic signal. A sample of the external fluid may be stored within the device upon collapse of the acoustic cavity.

In accordance with another embodiment of the invention, a device includes an isolated cavity that is initially inaccessible to an exterior environment, and an electrically passive timing mechanism. A mechanical structure separates the isolated cavity from the exterior environment, such that at the end of a timing interval the timing mechanism acts on the mechanical structure in a way that ruptures and/or collapses it, thus bringing the isolated cavity in contact with the exterior environment.

In accordance with a related embodiment of the invention, the device timing mechanism may include a timing membrane or piston, a timing cavity, and a conduit that may be a microfluidic channel or a capillary tube, and that may have a predefined geometry. Upon applying pressure to a timing fluid within the conduit, the timing fluid advances within the microfluidic channel at a speed, for example, that may be dictated by the predefined channel geometry and known timing fluid properties Upon reaching and filling the timing cavity after a timing interval the timing fluid applies pressure to the timing diaphragm or piston which collapses the mechanical structure, thus allowing external fluid to enter the isolated cavity. The conduit may be, without limitation, initially at least partially filled with the timing fluid. In other embodiments, the timing fluid may be, without limitation, the external fluid that enters from the isolated cavity.

In accordance with further related embodiments of the invention, the device may include an external device for applying pressure to the timing fluid. The mechanical structure may be an isolation membrane and/or diaphragm. The isolated cavity may include a sampling chamber, the sampling chamber including a check valve that allows flow of fluid into the sampling chamber but prevents flow of fluid out of the sampling chamber. An acoustic signal may be emitted from the device upon rupture of the mechanical structure. The isolated cavity and the mechanical structure may be shaped to emit a predetermined acoustic signal upon the mechanical structure collapsing. The isolated cavity may include a sensor element for performing a detection and/or a measurement on the fluid. The sensor element may include a material that interacts, such as chemically, with the fluid. The sensor element may include an electrode, allowing, for example, an electrochemical measurement to be performed on the fluid sample. The sensor element may be a Micro-Electro-Mechanical Systems (MEMS) device that may be microfabricated.

In accordance with further embodiments of the invention, the external device for applying pressure to the timing fluid may include a device such as an accumulator, that incorporates a piston or a membrane, to which a force is transmitted using any means known in the art, such as a cushion of compressed gas, or a mechanical spring, or contact with a reservoir of fluid that is itself pressurized. The said reservoir of fluid may be the external fluid itself. Alternatively, the external device for applying pressure to the timing fluid may include a flexible bag, itself placed within a pressurized reservoir, such as the pressure of the reservoir is transmitted to the timing fluid. Such a reservoir may be pressurized by any means known in the art, such as by using a compressed gas cushion, or a mechanical spring mechanism, or contact with a reservoir of fluid that is itself pressurized. The said reservoir of fluid may be the external fluid itself In accordance with further related embodiments of the invention, two systems, each including multiple sampling devices that are timed such as to acquire the corresponding samples at different times, may have the mechanical structure of the last sampling device of the first system connected to the timing fluid reservoir of the second system. At the same time, the sampling cavity of the last sampling device of the first system may be connected to the timing fluid channels of the second device. In this configuration, the collapse or rupture of the mechanical structure of the last sampling device of the first system triggers the start of the sampling using the second system, thus allowing the systems to be connected in a daisy-chain configuration.

In accordance with yet further embodiments of the invention, the isolated cavity may include a micro-particle, a nano-particle, a chemical product, and/or a pharmaceutical product, which is released into the environment after the collapse and/or rupture of the mechanical structure separating the isolated cavity from the exterior environment. The device may include a filter and/or a sieve to retain broken mechanical structure parts from entering at least one of the isolated cavity and the environment surrounding the device.

In accordance with additional related embodiments of the invention, the device may include a plurality of isolated cavities, a plurality of passive timing mechanisms, and a plurality of mechanical structures. At least one of the passive timing mechanisms may have a timing interval different from the other timing mechanisms, such that the mechanical structures associated with the at least one passive timing mechanism ruptures and/or collapses at a different time.

In accordance with still further related embodiments of the invention, a system may include a plurality of the above-described devices, wherein each device has an acoustic signature upon collapse of its associated mechanical structure, wherein the acoustic signatures of the devices vary. A system may include a plurality of the above-described devices, wherein at least one device has a conduit having different dimensions than another device in the system, such that the timing fluid of the different sampling mechanisms reach their associated cavities at different times so as to produce multiple acoustic events that occur at different times. A tool may incorporate one or more of the above-described devices, the tool having an interior flow-line through which a sample fluid is capable of circulating and in which the one or more devices are positioned, wherein said sample fluid when circulating in the interior flow-line contacts the devices. The tool may further include at least one microphone for receiving acoustic emissions from the one or more devices, and a processor for performing timestamping of the received acoustic emissions and/or determination of device positioning. A method using at least one of the above-described devices may include deploying the device within one of a pipe, a well, an engine, a hydrocarbon reservoir, an aquifer, a body of water, a waste disposal reservoir, an oil field tool, a proppant formulation and a living body.

In accordance with yet further related embodiments of the invention, a system may include a plurality of the above-described devices, wherein the system is incorporated into an underwater measurement system. The system may be attached or otherwise embedded in a cable. The cable may be further attached to a fixed buoy, or towed through a body of water by a ship or an underwater vehicle.

In accordance with another embodiment of the invention, a method includes deploying a device in an external fluid. A cavity is opened within the device to the external fluid, at a time determined by an electrically passive timing mechanism. Upon the cavity opening, a micro-particle, a nano-particle, a chemical product, and/or a pharmaceutical product is released from the cavity into the external fluid, and/or a sample of the external fluid may be stored within the device. The particle or chemical or pharmaceutical product stored within the cavity may react in an aggressive or explosive way with the external environment.

In accordance with related embodiments of the invention, the passive timing mechanism may include a timing diaphragm or a piston, a timing cavity; a conduit that may be a microfluidic channel or a capillary tube, and that may have a predefined geometry. Upon applying pressure to a timing fluid within the conduit, the timing fluid advances within the microfluidic channel at a speed, for example, that may be dictated by the predefined channel geometry and known timing fluid properties. Upon reaching the timing cavity after a timing interval, the timing fluid applies pressure to the timing diaphragm or piston which opens the cavity within the device to the external fluid. The conduit may be, without limitation, initially at least partially filled with the timing fluid. In other embodiments, the timing fluid may be, without limitation, the external fluid that enters from the isolated cavity.

In accordance with further related embodiments of the invention, deploying the device may include pumping the device into a geological formation and/or a formation fracture. The device may be deployed in a pipe, a well, an engine, a hydrocarbon reservoir, an aquifer, a body of water, an oil field tool, a waste disposal reservoir, a proppant formulation and/or a living body.

In accordance with still further embodiments of the invention, the method may include emitting by the device an acoustic signature when the cavity is opened. The acoustic signature may be detected using, at least in part, one or more microphone. A position of the device may be extracted from the detected acoustic signature using triangulation, compressional signal processing, and/or shear signal processing.

In accordance with another embodiment of the invention, a device includes an electrically passive timing mechanism and a mechanical structure. At the end of a timing interval, the timing mechanism ruptures the mechanical structure so as to emit an acoustic signal.

In accordance with related embodiments of the invention, the device may include an isolated cavity, wherein the mechanical structure separates the isolated cavity from the exterior environment, and wherein rupturing the mechanical structure brings the isolated cavity in contact with the exterior environment. The mechanical structure may be an isolation membrane.

In accordance with further embodiments of the invention, the timing mechanism may include a timing diaphragm or a piston, a timing cavity, and a conduit that may be a microfluidic channel or a capillary tube, and that may have a predefined geometry. Upon applying pressure to a timing fluid within the conduit, the timing fluid advances within the microfluidic channel at a speed, for example, that may be dictated by the predefined channel geometry and known timing fluid properties. Upon reaching and filling the timing cavity, the timing fluid applies pressure to the timing diaphragm or piston, which ruptures and/or collapses the mechanical structure, which thus may allow external fluid to enter the isolated cavity. The conduit may be, without limitation, initially at least partially filled with the timing fluid. In other embodiments, the timing fluid may be, without limitation, the external fluid that enters from the isolated cavity. The isolated cavity may include a sampling chamber, the sampling chamber including a check valve that allows flow of fluid into the sampling chamber but prevents flow of fluid out of the sampling chamber. The sampling chamber may include a sensor element for performing at least one of a detection and a measurement on the fluid. The sensor element may include a material that interacts with the fluid. The sensor element may include electrodes allowing an electrochemical measurement to be performed on the fluid sample.

In accordance with further related embodiments of the invention, the mechanical structure may be shaped to emit a predetermined acoustic signature upon rupturing. The device may be microfabricated.

In accordance with still further related embodiments of the invention, a system includes a plurality of the above-described devices, wherein each device has an acoustic signature upon rupture of its associated mechanical structure, wherein the acoustic signatures of the devices vary. The system may be incorporated into an underwater measurement system. The devices may be attached to a cable. The cable may be towed through a body of water by one of a ship and an underwater vehicle. The device(s) may be used during a hydraulic fracturing operation.

In accordance with various embodiments of the invention, the timing fluid in the above-described embodiments may either be a Newtonian fluid of known viscosity or a non-Newtonian fluid of known rheology. A complex non-Newtonian shear-thinning fluid may have a number of advantages, namely the fact that the non-Newtonian timing fluid will have a very high viscosity at low shear stress (i.e. at low applied pressure), but the viscosity will drop rapidly as the stress is increased. In various embodiments of the invention, a complex non-Newtonian fluid may be used as a timing fluid, resulting in a timing mechanism which only becomes active once the ambient pressure has reached a certain threshold value and providing additional versatility to the timing mechanism.

In accordance with another embodiment of the invention, a system includes one or more devices. Each device includes an isolated cavity that is initially inaccessible to an external fluid and an electrically passive timing mechanism. Each device further includes a mechanical structure that separates the isolated cavity from the exterior environment, such that at the end of a timing interval the timing mechanism acts on the mechanical structure to rupture and/or collapse the mechanical structure, thus bringing the isolated cavity in contact with the external fluid.

In accordance with related embodiments of the invention, the mechanical structure may be made of an inorganic material, a non-polymeric material, silicon, glass, or a ceramic, or combinations thereof. The mechanical structure may be insoluble in a liquid, such as water, bodily fluids, oil, crude oil, oil field fluid, salt water, or sea water, or combinations thereof.

In accordance with further related embodiments of the invention, the isolated cavity may be in fluidic communication with a sampling chamber. A one-way check valve may be included between the isolated cavity and the sampling chamber that allows fluid flow into the sampling chamber. The sampling chamber may include one or more chemical and/or biological reagents. The system may further include a filter for filtering fluid upon or prior to entering the sampling chamber. The filter may be a mechanical filter, a solid phase extraction column, a hydrocarbon filter, a gas chromatography preconcentrator, a packed column, a filter that collects and concentrates radioactive material, a biological filter, an absorbent medium, a scavenging medium, a hydrophobic material, or a hydrophilic material, or a combination thereof.

In accordance with yet further related embodiments of the invention, the sampling chamber of a first device of the one or more devices may include a piston and/or a flexible membrane that separates the sampling chamber into a first portion and a second portion, with the first portion in fluidic communication with the isolated cavity. The second portion may be in fluidic communication with an auxiliary chamber via a conduit, wherein the second portion is initially filled with a secondary liquid, and wherein upon rupture and/or collapse of the mechanical structure, fluid from the external environment enters the sampling chamber and applies pressure to the piston, which moves at a rate based, at least in part, on the value of the pressure of the external fluid, the viscosity of the secondary liquid and/or the geometry of said conduit. The conduit may include a constriction or a capillary tube.

In accordance with still further related embodiments of the invention, the one or more devices may include a second device, wherein the mechanical structure of the second device separates the isolated cavity of the second device from a pressurized fluid. The isolated cavity of the second device is in fluidic communication with the second portion of the sampling chamber, such that at the end of a timing interval the timing mechanism of the second device acts on the mechanical structure of the second device to rupture and/or collapse the mechanical structure of the second device, thus bringing the isolated cavity of the second device and the second portion of the sample chamber in fluidic communication with the pressurized fluid. The timing mechanisms of the first and second device may be configured such that the mechanical structure of the second device ruptures and/or collapses after the mechanical structure of the first device ruptures and/or collapses.

In accordance with related embodiments of the invention, the one or more devices may include a third device having a mechanical structure in fluidic communication with the first portion of the sampling chamber, such that rupture and/or collapse of the mechanical structure of the third device allows fluid communication between the first portion of the sampling chamber and a second sampling chamber. The timing mechanism of the third device may be configured such that the mechanical structure of the third device ruptures and/or collapses after the mechanical structure of the second device ruptures and/or collapses. The sampling chamber and/or the second sampling chamber may include a reagent.

In accordance with further related embodiments, the first portion of the sampling chamber may include a filter for retaining certain components from fluid entering the sampling chamber, the filter positioned within the sampling chamber such that fluid flowing between the sampling chamber and the second sampling chamber transports the retained filtered components. The system may further include: a first reservoir between the piston and the first portion of the sampling chamber, the first reservoir filled with a fluid and/or a reagent solution in fluidic communication with the first portion, such that fluid can flow from the first reservoir to the first portion of the sampling chamber; and a second reservoir in fluidic communication with the first portion of sampling chamber, the second reservoir for receiving overflow from the first portion of the sampling chamber, wherein upon the collapse and/or rupture of the third devices mechanical structure, the fluid and/or reagent solution from the first reservoir flows through the filter and into the second sampling chamber.

In accordance with yet further related embodiments of the invention, the passive timing mechanism may include a timing diaphragm or a piston, a timing cavity and a conduit that may be a microfluidic channel or a capillary tube, and that may have a predefined geometry. Upon applying pressure to a timing fluid within the conduit, the timing fluid advances within the microfluidic channel at a speed, for example, that may be dictated by the predefined channel geometry and known timing fluid properties. Upon the timing fluid reaching the timing cavity and filling it after a timing interval, the timing fluid applies pressure to the timing diaphragm or piston which ruptures and/or collapses the mechanical structure thus allowing external fluid to enter the isolated cavity. The conduit may be, without limitation, initially at least partially filled with the timing fluid. In other embodiments, the timing fluid may be, without limitation, the external fluid that enters from the isolated cavity.

In accordance with still further related embodiments of the invention, the one or more devices may include a first and second device, wherein the isolated cavity of the first device is coupled to the timing cavity of the second device via a conduit. Upon rupture and/or collapse of the mechanical structure of the first device, external fluid enters the isolated cavity of the first device and further communicates with the timing cavity of the second device. The timing cavity of the second device fills and the external fluid pressure is applied to the timing diaphragm or piston of the second device, causing the mechanical structure of the second device to collapse and/or rupture.

In accordance with yet further related embodiments of the invention, the system further includes a controller configured to determine viscosity of the external fluid based on, at least in part, a measurement associated with the time of rupture and/or collapse of the one or more devices. The measurement may be an acoustic measurement, an electronic measurement, or an optical measurement, or a combination thereof. The system may further include a third device, the isolated cavity of the second device in fluidic communication with the timing mechanism of the third device, wherein the timing mechanisms of the second and third devices differ.

In accordance with further related embodiments of the invention, the system may further include a manifold. The manifold is in fluidic communication with the isolated cavity of each device upon rupture and/or collapse of their associated mechanical structure. Additionally, a sampling conduit is in fluidic communication with the manifold and the external fluid. The sampling conduit may further be in communication with a reagent reservoir that holds a reagent. A mixer may be utilized for mixing the reagent and the fluid from the external environment. The sampling conduit may include a sensor for performing measurements on fluid within the sampling conduit.

In accordance with still further related embodiments of the invention, the system may include a first and a second group of the one or more devices, wherein the isolated chamber of one of the devices in the first group of devices is coupled to the timing mechanism of each of the devices in the second group, such that the mechanical structures of the second group rupture and/or collapse after the mechanical structure of the one of the devices. The external fluid of the at least one or more devices may differ.

In accordance with further related embodiments of the invention, the system may further include a triggering mechanism configured to turn on and/or off the timing mechanism of at least one of the devices upon an external command. The triggering mechanism includes a component selected from a check valve, a solenoid valve, a one-shot valve, a fluidic switch, a MEMS component, a detonator and any combination thereof.

In accordance with another embodiment of the invention, a method for determining viscosity of an external fluid is provided. The method includes deploying a system in an external fluid, the system including a plurality of devices. An isolated cavity of a first device is opened at a time determined by an electrically passive timing mechanism of the first device, such that the external fluid enters the isolated cavity of the first device. The isolated cavity of the first device is in fluidic communication with a timing mechanism of the second device. An isolated cavity of a second device is opened at a time determined by the timing mechanism of the second device. Viscosity of the external fluid is determined based on, at least in part, a measurement associated with the opening of the isolated cavities of the first and second devices.

In accordance with related embodiments of the invention, the passive timing mechanism of each device may include a timing diaphragm or a piston, a timing cavity; and a conduit in fluidic communication with the timing cavity. Upon applying pressure to a timing fluid within the conduit, said timing fluid advances within the conduit and upon reaching the timing cavity and filling it after a timing interval, the timing fluid applies pressure to the timing diaphragm or piston which ruptures and/or collapses the mechanical structure thus allowing external fluid to enter the isolated cavity.

In accordance with further related embodiments of the invention, determining viscosity may include performing a measurement, such as an acoustic measurement, an electronic measurement, an optical measurement, or combinations thereof.

In still further related embodiments of the invention, the isolated cavity of the second device is in fluidic communication with a timing mechanism of a third device. The method further includes opening an isolated cavity of the third device, at a time determined by the timing mechanism of the third device, wherein the timing mechanisms of the second and third devices differ. Determining viscosity of the external fluid may be based on, at least in part, a measurement associated with the opening of the isolated cavities of the first, second and third devices.

In accordance with another embodiment of the invention, a method includes deploying a system in an external fluid, the system including one or more devices. An isolated cavity of a first device of the one or more devices is opened, at a time determined by an electrically passive timing mechanism of the first device, such that the external fluid enters the isolated cavity of the first device, the isolated cavity of the first device in fluidic communication with a sampling chamber.

In accordance with related embodiments of the invention, the sampling chamber may include one or more chemical and/or biological reagents. The method may include filtering the fluid upon or prior to entering the sampling chamber. The filter may be a mechanical filter, a solid phase extraction column, a hydrocarbon filter, a gas chromatography preconcentrator, a packed column, a filter that collects and concentrates radioactive material, a biological filter, an absorbent medium, a scavenging medium, a hydrophobic material, a hydrophilic material, or combination thereof. The method may include preventing backflow of the fluid from the sampling chamber to the isolated cavity.

In accordance with yet further related embodiment of the invention, the sampling chamber of the first device may include a piston and/or a flexible membrane that separates the sampling chamber into a first portion and a second portion, the first portion in fluidic communication with the isolated cavity. The second portion may be in fluidic communication with an auxiliary chamber via a conduit, wherein the second portion is initially filled with a secondary liquid, and wherein upon opening the isolated cavity of the first device, the external fluid enters the first portion of the sampling chamber and applies pressure to the piston, which moves at a rate based, at least in part, on the value of the pressure of the external fluid, the viscosity of the secondary liquid and/or the geometry of said conduit.

In accordance with still further related embodiments of the invention, the one or more devices may include a second device, an isolated cavity of the second device in fluidic communication with the second portion of the sampling chamber. The method may further include opening the isolated cavity of a second device, at a time determined by a timing mechanism of the second device, bringing the isolated cavity of the second device and the second portion of the sample chamber in fluidic communication with a pressurized fluid. The timing mechanisms of the first and second device are configured such that the mechanical structure of the second device ruptures and/or collapses after the mechanical structure of the first device ruptures and/or collapses.

In accordance with further embodiments of the invention, the one or more devices may include a third device having a mechanical structure in fluidic communication with the first portion of the sampling chamber. The method further includes rupturing and/or collapsing the mechanical structure of the third device, allowing fluid communication between the first portion of the sampling chamber and a second sampling chamber. A timing mechanism of the third device is configured such that the mechanical structure of the third device ruptures and/or collapses after the isolated cavity of the second device opens. The sampling chamber and/or the second sampling chamber may include a reagent.

In accordance with still further related embodiments of the invention, the method may include filtering components from fluid entering the sampling chamber, the filtering positioned within the sampling chamber such that fluid flowing between the sampling chamber and the second sampling chamber includes the filtered components. There may be a first reservoir between the piston and the first portion of the sampling chamber, the first reservoir filled with a fluid and/or a reagent solution in fluidic communication with the first portion, such that fluid can flow from the first reservoir to the first portion of the sampling chamber. There may be a second reservoir in fluidic communication with the first portion of sampling chamber, the second reservoir for receiving overflow from the first portion of the sampling chamber, wherein upon opening the third devices mechanical structure, the fluid and/or reagent solution from the first reservoir flows through the filter and into the second sampling chamber.

In accordance with another embodiment of the invention, an electrically passive sampling device such as in the described-above embodiments, may be used to sample fluid in highly flammable or explosive environment, such as refinery equipment, pipes and tanks, fuel tanks, gas tanks, oilfield separation reservoirs, oilfield production and exploration rigs, oilfield wellhead equipment. The intrinsic electrically-passive nature of the device assures that no electrical spark risk is present, by design. Such a sampling device may furthermore be used to acquire individual samples at different times, or at different depths. This would allow, for example, the acquisition of samples at different depths within a refinery tank to understand the details of the composition variations by depth, or of the stratification that may take place in such tanks.

In accordance with another embodiment of the invention, an electrically passive sampling device such as in the described-above embodiments, may be placed near a nuclear facility, in an atmospheric and/or aquatic environment, the start of the sampling program being triggered upon the occurrence of an external event such as, without limitation, an accident alert, a power outage, a military attack, a terrorist attack and/or a natural disaster.

In accordance with another embodiment of the invention, an electrically passive device/system such as in the described-above embodiments, is deployed in an urban or suburban location, the start of the sampling program being triggered upon the occurrence of an external event such as, without limitation, an accident alert, a chemical accident, a nuclear accident, a military attack, a terrorist attack and/or a natural disaster.

In accordance with another embodiment of the invention, an electrically passive device/system such as in the described-above embodiments, is mounted on a water supply line or pipe. Sampling may be triggered by an external event such as, without limitation, a user signal, a signal from an in-line measurement system, an external event such as an accident alert, a military attack, a terrorist attack and/or a natural disaster.

In accordance with another embodiment of the invention, an electrically passive device/system such as in the described-above embodiments, is mounted on a ground-based or aerial vehicle, robot or drone. Sampling may be triggered by an external event such as, without limitation, a user signal, a signal from an in-line measurement system, an external event such as an accident alert, a military attack, a terrorist attack and/or a natural disaster.

In accordance with another embodiment of the invention, an electrically passive device/system such as in the described-above embodiments, is mounted on a submerged device such as, without limitation, a mechanical structure, a rig, a cable, a submarine, a remotely operated underwater vehicle, an autonomous underwater vehicle, a glider, a ship or a buoy. Sampling may be triggered by an external event such as, without limitation, a user signal, a signal from an in-line measurement system, a signal from the submerged device, a fluorescence signal, an external event such as an accident alert, a military attack, a terrorist attack and/or a natural disaster.

In accordance with another embodiment of the invention, a multitude of devices/systems such as in the above-described embodiments may be deployed at different locations surrounding a structure to be monitored, such that the data collected from analyzing the different samples, either in-situ or after retrieval, is used to generate a map of the evolution of the component of interest in multiple dimensions (up to three spatial coordinates and time). Example could be the monitoring of the pollution generated by an offshore oil well, from a tanker or pipe accident, from a chemical plant, from a nuclear power plant, from car traffic, contamination from a military attack or from a terrorist attack and/or a natural disaster.

In accordance with another embodiment of the invention, a method for acquiring at least one sample from a fluid is provided. The method includes deploying at least one device in the fluid. Each device includes a sampling mechanism having an isolated cavity that is initially inaccessible to the external fluid; an electrically passive timing mechanism including a piercing structure; and a mechanical structure separating the isolated cavity from the exterior environment. At the end of a timing interval the piercing structure of the timing mechanism pierces the mechanical structure, bringing the isolated cavity in contact with the external fluid.

In accordance with related embodiments of the invention, the timing interval may be less than 100 ms. The method may further include storing a sample of the fluid within the cavity. The passive timing mechanism may include a piston. The method may further include emitting by the device an acoustic signature when the mechanical structure is pierced.

In accordance with further related embodiments of the invention, the piston may be configured to move within the isolated cavity, the timing mechanism may be configured to advance the piston, and advancement of the piston causes the piercing structure to pierce the mechanical structure. The piston may include the piercing structure. The timing mechanism may include a conduit, the method further including applying pressure to a timing fluid within the conduit causing the piston to advance such that the piercing structure pierces the mechanical structure, allowing external fluid to enter the isolated cavity. The timing mechanism may include a timing cavity, the conduit in fluidic communication with the timing cavity, the method further comprising applying pressure to the timing fluid within the conduit such that the timing fluid advances within the conduit and upon reaching the timing cavity and filling it after a timing interval, the timing fluid applies pressure to a side of the piston, causing the piston to advance such that the piercing structure pierces the mechanical structure, allowing external fluid to enter the isolated cavity. The timing interval may be predetermined based, at least in part, on geometry of the channel, volume of the timing cavity, pressure applied to the timing fluid, or timing fluid properties, or any combination thereof. The at least one device may include a plurality of sampling mechanisms having varying timing cavity volumes.

In accordance with yet further related embodiments of the invention, at least one of the one or more devices includes a plurality of sampling mechanisms having varying timing intervals. The timing mechanism of each sampling mechanism may include a timing cavity, and a conduit in fluidic communication with the timing cavity, the method further comprising applying pressure to a timing fluid within the conduit, such that the timing fluid advances within the conduit and fills the timing cavity, the timing interval of each sampling mechanism may be predetermined based, at least in part, the volume of the timing cavity, and wherein the plurality of sampling mechanisms have varying timing cavity volumes.

In accordance with still further related embodiments of the invention, the sampling mechanism further includes a sampling chamber coupled to the isolated cavity. The method may further include decoupling the sampling chamber from the isolated cavity.

Accordance with further related embodiments of the invention, the method may include applying a trigger signal to start the timing mechanism. The one or more devices may include a first device and a second device, and wherein applying the trigger signal to the second device is based, at least in part, on the acquisition of a sample by the first device. At least one of the one or more devices may include a first sampling mechanism and a second sampling mechanism, and wherein applying the trigger signal to the second sampling mechanism is based at least in part, on the acquisition of a sample by the first sampling mechanism.

In accordance with yet further related embodiments of the invention, the method may further include recording sample acquisition time of each sample. Each sampling mechanism may include a sample chamber for storing an acquired sample, the method further including monitoring the sample chamber using one of an optical sensor, a conductivity sensor, a temperature sensor, a force sensor, a deflection sensor, a chemical sensor, a biological sensor, a pressure sensor and a pressure switch, or a combination thereof, so as to detect the acquired sample. Each device may include a sample chamber for storing an acquired sample, the sample chamber at least partially filled with a culture medium, a chemical reagent or a biological reagent, or a combination thereof.

In accordance with an embodiment of the invention, a system for acquiring samples in a body of fluid includes a containment unit that is negatively buoyant relative to the body of fluid. A sampling array is tethered to the containment unit, the sampling array including a plurality of sampling devices positioned along the array, for sampling the body of fluid at varying depths.

In accordance with related embodiments of the invention, the sampling array may include a buoyancy device. One or more of the sampling devices may be positively buoyant relative to the body of fluid. The system may include a latching mechanism for releasably holding the tethered sampling array in an initial position relative to the containment unit. A trigger mechanism may control the latching mechanism to release the sampling array, wherein the sampling array, still tethered to the containment unit at a first end, ascends in the body of fluid. The trigger mechanism may control the latching mechanism by providing to the latching mechanism an acoustic signal, an electric signal, an optical signal, an electromagnetic signal, or a mechanical signal, or a combination thereof. The containment unit may include a receiver for receiving a control signal that may be an acoustic signal or an optical signal, the trigger mechanism controlling the latching mechanism as a function of the control signal. The trigger mechanism may check at predefined times for receipt of the control signal, and if the control signal is not received after a period of time, the trigger mechanism controls the latching mechanism so as to release the sampling array, such that the sampling array, still tethered to the containment unit at the first end, ascends in the body of fluid. The system may further include a surface buoyancy device configured to remain at the surface of the body of fluid, the surface buoyancy device including a transmitter/receiver device configured to receive a deployment signal, and upon receipt of the deployment signal, transmit a control signal to the trigger mechanism, causing the trigger mechanism to release the sampling array, such that the sampling array, still tethered to the containment unit at the first end, ascends in the body of fluid. The trigger mechanism may include an acoustic release, a device commonly used in fields such as oceanography. The latching mechanism may include a fusible wire and means of sending an electrical current through the fusible wire, leading to the melting of the fusible wire and the release of the sampling array. The latching mechanism may further include means to providing mechanical advantage to the strength of the fusible wire.

In accordance with further related embodiments of the invention, upon each sampling device acquiring all their samples, the sampling array may be configured to automatically release from its tether with the containment unit. The sampling array may include a Global Positioning System (GPS), and a transmitter for transmitting GPS coordinates. The system may further include an installation/retrieval tether and the containment unit may include a latch mechanism for releasably connecting the tether.

In accordance with still further related embodiments of the invention, the sampling array may include an accelerometer, a tiltmeter, a gyroscope, a relative bearing device, an inclinometer, or a compass, or any combination thereof, for providing positional information of the sampling array relative to the containment unit. The system may further include a memory device for recording the positioning information.

In accordance with yet further related embodiments of the invention, each sampling device may include one or more sampling mechanisms each having an electronically passive timing mechanism, each sampling mechanism configured to acquire a sample at a time determined by their associated electronically passive timing mechanism. Each sampling mechanism may further include an isolated cavity that is initially inaccessible to an external fluid, and a mechanical structure separating the isolated cavity from the exterior environment, wherein at the end of a timing interval the timing mechanism pierces the mechanical structure, bringing the isolated cavity in contact with the body of fluid. Each sampling mechanism may further include a trigger mechanism for triggering each timing mechanism. Each timing mechanism may be configured to be triggered upon deployment of the system in the body of fluid.

In accordance with further related embodiments of the invention, the system may further include a monitoring system for recording sample acquisition time of each acquired sample. Each sampling device may include a sample chamber for storing an acquired sample, and the monitoring system includes one of an optical sensor, a conductivity sensor, a temperature sensor, a force sensor, a deflection sensor, a chemical sensor, a biological sensor, a pressure sensor and a pressure switch, or a combination thereof. Each sampling device may include a sample chamber for storing an acquired sample, the sample chamber at least partially filled with a chemical reagent, an absorption medium, a biocide, a biological reagent, or a combination thereof. The system may further include a secondary buoyancy device held in an undeployed position within or proximate the containment unit, the secondary buoyancy device configured upon activation to extend to the surface of the body of fluid via a tether attached to the containment unit, such that the tether can be retrieved on the surface along with the containment unit.

In accordance with another embodiment of the invention, a method for acquiring samples in a body of fluid is provided. The method includes deploying a containment unit that is negatively buoyant relative to the body of fluid, a sampling array tethered to the containment unit, the sampling array including a plurality of sampling devices positioned along the array, for sampling the body of fluid at varying depths.

In accordance with related embodiments of the invention, the sampling array may include a buoyancy device. One or more of the sampling devices may be positively buoyant relative to the body of fluid.

In accordance with further related embodiments of the invention, the sampling array may be buoyant relative to the body of fluid, and the containment unit includes a latching mechanism for releasably holding the tethered sampling array in an initial position relative to the containment unit, the method further including controlling the latching mechanism so as to release the sampling array, such that the sampling array, still tethered to the containment unit at a first end, ascends in the body of fluid. Controlling the latching mechanism may include providing to the latching mechanism an acoustic signal, an electric signal, an optical signal, an electromagnetic signal, or a mechanical signal, or a combination thereof. The containment unit may include a receiver for receiving a control signal selected from the group consisting of an acoustic signal and an optical signal, and wherein controlling the latching mechanism is based, at least in part, on receipt of the control signal by the receiver. The method may further include: checking, by the receiver at predefined times, for receipt of the control signal; and, if the control signal is not received by the receiver after a predetermined period of time, controlling the latching mechanism to release the sampling array, such that the sampling array, still tethered to the containment unit at the first end, ascends in the body of fluid. The trigger mechanism may include an acoustic release, a device commonly used in fields such as oceanography. The latching mechanism may include a fusible wire and means of sending an electrical current through the fusible wire, leading to the melting of the fusible wire and the release of the sampling array. The latching mechanism may further include means to providing mechanical advantage to the strength of the fusible wire.

In accordance with further related embodiments of the invention, the method may further include deploying a surface buoyancy device configured to remain at the surface of the body of fluid, the surface buoyancy device including a transmitter/receiver device, the containment unit including a receiver device. The method further includes: receiving at the transmitter/receiver device a trigger signal; transmitting, by the transmitter/receiver device, a command signal to the containment unit upon receipt of the trigger signal; and receiving, by the receiver device, the command signal, whereupon the latching mechanism is controlled to release the sampling array, such that the sampling array, still tethered to the containment unit at the first end, ascends in the body of fluid.

In accordance with still further related embodiments of the invention, the method may further include, upon each sampling device acquiring all their samples, releasing the sampling array from its tether with the containment unit, such that the sampling array ascends to the surface. The sampling array may include a Global Positioning System (GPS) and a transmitter, the method further including transmitting the GPS coordinates via the transmitter.

In accordance with yet further related embodiments of the invention, the method may include determining position information of the sampling array relative to the containment unit. Determining position information of the sampling array relative to the containment unit may include using an accelerometer, a tiltmeter, a gyroscope, a relative bearing device, an inclinometer, or a compass, or any combination thereof, so as to provide positional information of each sampling device of the sampling array relative to the containment unit. The position information may be stored on a memory device.

In accordance with further related embodiments of the invention, each sampling device may include one or more sampling mechanisms each having an electronically passive timing mechanism. The method may further include acquiring, by each sampling mechanism, a sample at a time determined, at least in part, by their associated electronically passive timing mechanism. Each sampling mechanism may further include: an isolated cavity that is initially inaccessible to an external fluid; and a mechanical structure separating the isolated cavity from the exterior environment, the method further including, at the end of a timing interval determined by the timing mechanism, piercing the mechanical structure, bringing the isolated cavity in contact with the body of fluid. The method may include triggering each timing mechanism so as to start the timing interval. Each timing mechanism may be configured to be triggered upon deployment of the system in the body of fluid.

In accordance with still further related embodiments of the invention, the method may further include determining sample acquisition time of each acquired sample, and storing the determined sample acquisition times in a memory device. Each sampling device may include a sample chamber for storing an acquired sample, wherein determining sample acquisition time of each sample includes using one of an optical sensor, a conductivity sensor, a temperature sensor, a force sensor, a deflection sensor, a chemical sensor, a biological sensor, a pressure sensor and a pressure switch, or a combination thereof. Each sampling device may include a sample chamber for storing an acquired sample, the sample chamber at least partially filled with a chemical reagent, an absorption medium, a biocide, a biological reagent, or a combination thereof.

In accordance with yet further related embodiments of the invention, the method may further include holding a secondary buoyancy device in an undeployed position within or proximate the containment unit; releasing the secondary buoyancy device via a tether attached to the containment unit so that it reaches the surface of the body of fluid; and retrieving the tether along with the containment unit.

In accordance with further related embodiments of the invention, deploying the containment unit may include positioning the containment unit so that it rests at a predetermined position on the bottom floor of the body of fluid.

Positioning the containment unit may include using one of a surface vessel or a remotely operated underwater vehicle (ROV), or a combination thereof. Positioning the containment unit may include using a GPS system.

In accordance with another embodiment of the invention, a device includes an isolated cavity that is initially inaccessible to the external fluid. The device includes a device body including one or more structural elements supporting a mechanical structure, the mechanical structure separating the isolated cavity from the external fluid. The device further includes a piercing structure for piercing the mechanical structure, and an electrically passive timing mechanism including a fluidic timing cavity. At the end of a timing interval fluid within the timing cavity causes a piercing structure to pierce the mechanical structure, causing the mechanical structure to collapse, rupture and/or fracture, wherein an acoustic signal is emitted when the mechanical structure is pierced.

In accordance with related embodiments of the invention, the structural elements may be made of a material that is different from the mechanical structure. The structural elements may include a ceramic, a metal, a plastic or a resin, or combinations thereof, and the mechanical structure may include silicon, a ceramic, a sapphire or glass, or combinations thereof.

In accordance with further related embodiments of the invention, the structural elements, the mechanical structure, the timing mechanism and/or the piercing structure may be manufactured using additive manufacturing technologies. The additive manufacturing technology may be stereolithography, polyjet, inkjet printing, plastic laser sintering, direct metal laser sintering, fused deposition modeling, 3D printing in ceramic technology, or combinations thereof. The structural elements, mechanical structure, timing mechanism, and/or piercing structure may be manufactured using MEMS etching techniques such as deep reactive ion etching, inductively coupled plasma reactive ion etching, isotropic wet etching, anisotropic wet etching or combinations thereof.

In accordance with still further related embodiments of the invention, the mechanical structure may be more brittle than the structural elements. The piercing structure may be made from a material that is different from the mechanical structure. The piercing structure may be made from the same material as the structural elements. The piercing structure and the structural elements may be coupled via linkages that permit movement of the piercing structure. The piercing structure, the structural elements and the linkages may be manufactured monolithically.

In accordance with yet further related embodiments of the invention, the mechanical structure has a top and bottom surface, the top surface for facing the external fluid and the bottom surface for facing the piercing structure, wherein the mechanical structure may include partially etched geometry on the top surface and/or the bottom surface.

In accordance with further related embodiments of the invention, the external fluid entering the fluidic timing cavity may apply pressure to a timing diaphragm and/or piston so as to drive the piercing structure into the mechanical structure, causing the mechanical structure to collapse, rupture or fracture. The timing diaphragm may include a metal, a polymer, or a combination thereof. The electrically passive timing mechanism may include a porous structure and/or material that allows the external fluid to seep into the fluidic timing cavity, at a slow rate, causing the mechanical structure to collapse, rupture or fracture after a time delay. The electrically passive timing mechanism may include a fluidic circuit that allows the external fluid to enter the fluidic timing cavity at a slow rate, causing the mechanical structure to collapse, rupture or fracture after a time delay.

In accordance with still further related embodiments of the invention, a method of making the device may include using MEMS etching techniques. The MEMS etching techniques may include deep reactive ion etching, inductively coupled plasma reactive ion etching, isotropic wet etching, anisotropic wet etching, or combinations thereof, which may be used to make the structural elements, the piercing structure, the passive timing mechanism and/or the mechanical structure.

In accordance with yet further related embodiments, a method of making the device includes using an additive manufacturing technology. The additive manufacturing technology may include stereolithography, polyjet, inkjet printing, laser sintering, fused deposition modeling, 3D printing, or combinations thereof, which may be used to make the structural elements, the piercing structure, the passive timing mechanism, and/or the mechanical structure. The structural elements may include a metal, a ceramic, a plastic a resin, or combinations thereof, with the mechanical structure including silicon, ceramic, sapphire, or combinations thereof. The method may further include using MEMS technology to make the mechanical structure.

In accordance with still further related embodiments of the invention, the mechanical structure has a top and bottom surface, the top surface for facing the external fluid and the bottom surface for facing the piercing structure, wherein a method of making the device includes partially etching the top surface and/or the bottom surface.

In accordance with yet further related embodiments of the invention, a method of making the device includes coupling the piercing structure and the structural elements via linkages so as to permit movement of the piercing structure. The method may further include monolithically manufacturing the piercing structure and the structural elements.

BRIEF DESCRIPTION OF THE DRAWINGS

The foregoing features of the invention will be more readily understood by reference to the following detailed description, taken with reference to the accompanying drawings.

FIGS. 2(a-d) show the device of FIG. 1 in more detail, in accordance with an embodiment of the invention. FIG. 2(c) shows the device with the sample chamber filled with sample fluid. FIG. 2(d) shows the device ready to be interrogated after surface retrieval.

FIG. 4 shows a passive timing device that includes a pharmaceutical product for release within a human body, in accordance with an embodiment of the invention.

FIG. 5 shows a passive timing device that includes a filter for containing the broken diaphragm particles, in accordance with an embodiment of the invention.

FIG. 8A shows a viscosity measurement system that may be fully passive, in accordance with an embodiment of the invention.

FIG. 8B shows another viscosity-measurement system, in accordance with an embodiment of the invention.

FIG. 9A shows a sampling and measurement system that includes a manifold, in accordance with an embodiment of the invention.

FIG. 9B shows an external sampling conduit connected via a T-junction to a reagent reservoir, in accordance with an embodiment of the invention.

FIG. 10A shows a device that may be used to acquire a sample from a contaminated external fluid, in accordance with an embodiment of the invention.

FIG. 10B shows the device of FIG. 10A after sampling, in accordance with an embodiment of the invention.

FIGS. 11A-C shows a system capable of acquiring a sample from an external fluid, and maintaining it at a desired pressure for extended periods of time, in accordance with an embodiment of the invention. FIG. 11A shows the system prior to acquiring a sample. FIG. 11B shows the system after acquiring the sample. FIG. 11C shows the system after sample pressurization.

FIG. 12A shows a device for performing a sampling operation from a high-pressure external fluid without shocking the fluid, in accordance with an embodiment of the invention.

FIG. 12B shows the device of FIG. 12A that further allows the sample to be maintained at a high pressure after sampling, in accordance with an embodiment of the invention.

FIGS. 13A-D show, in chronological order, operations performed by a system that, in addition to sampling at a time controlled by a passive timing mechanism, integrates a mechanism allowing the subsequent transfer of the sample from an initial sampling chamber to another sampling chamber after a given amount of time, in accordance with an embodiment of the invention. FIG. 13A shows the system prior to acquiring a sample. FIG. 13B shows the system after collapse of a first device's mechanical structure. FIG. 13C shows the system after the later collapse of a second device's mechanical structure. FIG. 13D shows the system after the later collapse of a third device's mechanical structure. FIG. 13E shows the system of FIGS. 13A-D modified such that the sampling chamber 1305 including a first reservoir and a second reservoir.

FIG. 16(a) shows a sampling device that uses a piston in place of a timing diaphragm, and includes an optional triggering system, in accordance with an embodiment of the invention.

FIG. 16(b) shows the sampling device from FIG. 16A after the piston has pierced the mechanical structure, thus enabling the acquisition of a sample, in accordance with an embodiment of the invention.

FIG. 27(a) shows an override signal being emitted by a transmitter at the surface and detected by the sampling systems, in accordance with an embodiment of the invention.

FIG. 27(b) shows the override signal activating a buoyancy device to carry a retrieval tether to the surface for subsequent retrieval of the unactivated sampling systems from a body of water, in accordance with an embodiment of the invention.

FIG. 28 shows a sampling system in standby mode having an additional buoyancy device which remains at ocean surface level, and includes a data transmitter/receiver device, so that when a trigger signal is received, the device is able to send a deployment command via a cable to trigger the sampling system and/or release the sampling deployment buoyancy device, in accordance with an embodiment of the invention.

FIG. 47A shows typical elastic deflection of a circular clamped membrane under hydrostatic pressure applied to the top side, in accordance with an embodiment of the invention.

FIG. 47B shows a cross-section through a circular mechanical structure, and one possible positioning of the top-side etched geometry, in accordance with an embodiment of the invention.

FIGS. 47C, 47D, 47E shows top views of possible top-side etched geometries, in accordance with various embodiments of the invention.

FIG. 48A shows a mechanical structure geometry which has a membrane-like portion delimited by etching, in accordance with an embodiment of the invention.

FIGS. 48B and 48C show additional exemplary geometries of the membrane-like portion of the mechanical structure, in accordance with various embodiments of the invention.

FIG. 49 show different ways to manufacture the passive timing mechanism of the device, in accordance with various embodiments of the invention. More particularly, FIG. 49A shows the passive timing mechanism as a porous structure.

FIG. 49B shows the timing cavity integrated to the passive timing mechanism.

FIG. 49C show the passive timing mechanism as a fluidic circuit wherein the timing cavity is not integrated to the passive timing mechanism.

FIG. 49D shows the passive timing mechanism as a fluidic circuit wherein the timing cavity is integrated to the passive timing mechanism.

FIG. 50 shows the device of FIG. 35, but where the timing diaphragm is replaced by a piston structure, in accordance with an embodiment of the invention.

DETAILED DESCRIPTION OF SPECIFIC EMBODIMENTS

In illustrative embodiments, an electrically passive device and method for in-situ acoustic emission, and/or releasing, sampling and/or measuring of a fluid or various material(s) is provided. The device may provide a robust timing mechanism to release, sample and/or perform measurements on a predefined schedule, and, in various embodiments, emits an acoustic signal sequence(s) that may be used for triangulation of the device position within, for example, a hydrocarbon reservoir or a living body. Details are discussed below.

Figure 1:
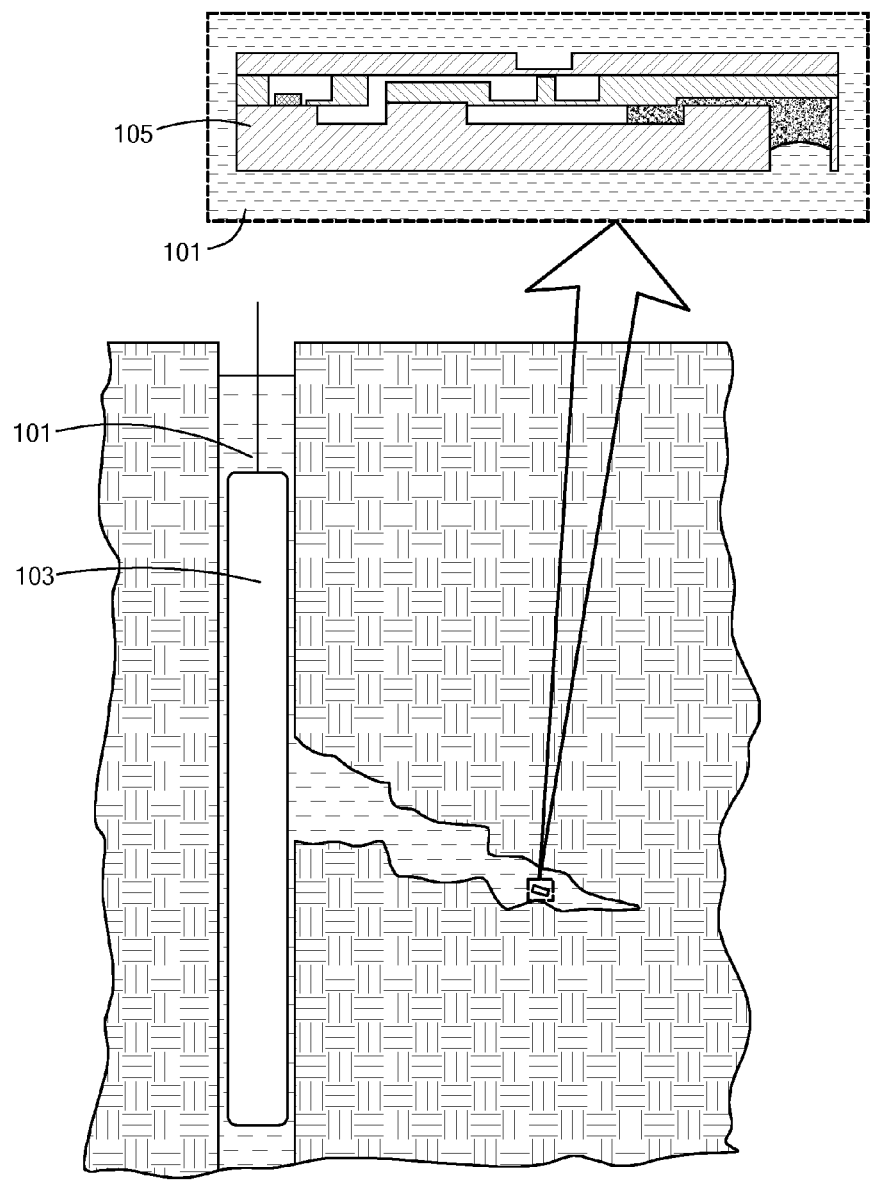
FIG. 1 shows deployment of a device for use in sampling hydrocarbons during fracturing or fluid injection operations, in accordance with an embodiment of the invention.

FIG. 1 shows deployment of a device 105 for use in sampling hydrocarbons during fracturing or fluid injection operations, in accordance with an embodiment of the invention. It should be noted that discussion of the specific device 105 shown, for use in sampling hydrocarbons, is for illustrative purposes only. Other device configurations and applications are within the scope of the present invention. For example, the device 105 may be deployed in a wide range of environments including, without limitation, within a pipe, a well, an engine, a hydrocarbon reservoir, an aquifer, a body of water, an oil field tool, a waste disposal reservoir, a proppant formulation and a living body to release, sample or measure various fluids (including a gas) or other material(s).

The device 105 may be deployed, without limitation, in downhole fluid 101 within a fracture in an underground formation. The device may be, for example, pumped or otherwise injected, into the rock matrix. The device 105 may work in combination with conventional oilfield measurement tools 103 or autonomous battery-operated sensors, that may be placed in the well in hydraulic communication with the fracture where the device 105 is injected. The device 105 may be used at very high pressures or temperatures, thus providing a pathway to performing measurements within wells which are currently inaccessible to existing sensor technology due to, without limitation, severely constrained geometry, corrosive fluids, elevated pressure and/or temperature. Examples of adverse well environments include recently developed deep-sea well reservoirs in the Gulf of Mexico. The device 105 may be used in areas with no available power. The device 105 may be used in explosive environments or atmospheres, where electric equipment poses a risk of explosion. The device 105 may be used for water and/or air quality monitoring in and around cities, chemical plants, nuclear sites, offshore platforms and other oilfield structures, military missions and battlegrounds. The device 105 may be used in robots such as marine remotely-operated underwater vehicles, autonomous underwater vehicles, airborne or ground drones and vehicles, and other types of robotic equipment. The device 105 may be used where and/or when there is no power available, such as in certain remote area.

The device may be of any size, dependent for example, on the application. In various embodiments, the device may be fabricated, at least in part, using micromachining or microsystem technology, using, for example, silicon, glass and/or ceramics. In various embodiments, certain portions of the device may not be included in the micromachined process, such as the sampling chamber (described in more detail below), which may be, for example, a separate vial or other container.

Figure 2A:
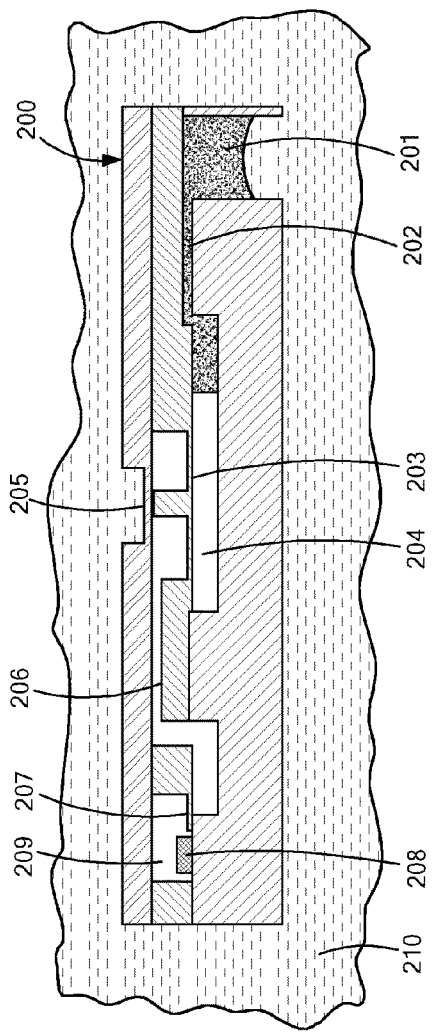
FIG. 2(a) shows the device prior to activation.

FIGS. 2(a-d) show the device in more detail, in accordance with various embodiments of the invention. FIG. 2(a) shows the device 200 prior to activation. The device 200 includes at least one sampling mechanism for obtaining a sample of the external oil-well fluid 210.

In illustrative embodiments, the sampling mechanism includes a microfluidic timing mechanism for obtaining the fluidic sample. More particularly, the microfluidic timing mechanism may include a conduit that may be a microfluidic channel 202 or a capillary tube. The conduit may be partially filled with a timing fluid 201 (in other embodiments, the timing fluid may be without limitation, the external fluid that enters from the isolated cavity 206, described in more detail below). Capillary trapped timing fluid 201 may initially be held in place within the microfluidic channel by, without limitation, surface tension. The microfluidic channel 202 leads to a timing cavity 204 that may be of known volume. The timing cavity 204 may initially be, without limitation, empty.

Upon applying pressure to the timing fluid 201, the timing fluid 201 advances within the microfluidic channel 202 into the timing cavity 204 such that it causes a mechanical structure 205 to rupture (and/or collapse) after a time delay. The mechanical structure 205 may be insoluble in the environment or fluid in contact with the device. The mechanical structure 205 may be insoluble in water, bodily fluids, oil, oil field fluid, crude oil, salt water, or sea water, or combinations thereof. The mechanical structure 205 may be made of an inorganic material, a non-polymeric material, silicon, glass, or a ceramic, or combinations thereof. As used in this description and the accompanying claims, the term "inorganic" shall have the meaning indicated, unless the context otherwise requires: a material composed of atoms or molecules not containing carbon with, the exception of certain forms of carbon such as graphene, diamond, nanotubes and bucky-balls, which shall be considered inorganic. Examples of inorganic materials include, without limitation, all metals, all types of glasses, silicon compounds such as oxides and nitrides, ceramic materials, silicon (in all crystalline forms), quartz, diamond, sapphire, ruby, as well as all materials of geologic origin.

In accordance with various embodiments, the timing fluid may be routed, prior to entering the timing channel, through a trigger device that can enable or disable the passage of timing fluid as desired. The trigger device may be one of a check valve, an electrically-controlled solenoid valve, a fluidic switch, or any other type of active valve known in the art. Examples of different types of valves used in microfluidic devices are provided in "Components for integrated poly(dimethylsiloxane) microfluidic systems" Electrophoresis 2002, 23, 3461-3473; "Micro Total Analysis Systems: Latest Achievements" Anal. Chem. 2008, 80, 4403-4419, incorporated herein by reference in its entirety. The trigger device may also include a one-shot valve that initially blocks the passage of timing fluid and upon receipt of an external signal permanently opens the passage of timing fluid without requiring further power.

Prior to rupturing, the mechanical structure 205 isolates an isolated cavity 206, which may include a sample chamber 209, from the external environment, which may include an external fluid (which may be a gas). The mechanical structure 205 may be, without limitation, an isolation diaphragm or isolation membrane that provides a barrier from the external environment. An example of a delayed actuator with a visco-elastic timer is described in U.S. Pat. No. 4,791,251 (Carter et al.), which is hereby incorporated by reference, in its entirety.

Illustratively, the timing fluid 201 entering the timing cavity 204 may cause a timing diaphragm 203 to deflect. A piercing structure, such as a protrusion or other shaped structure on the timing diaphragm 203, may then rupture or otherwise pierce the mechanical structure 205. Various other membrane rupture mechanisms known in the art of microfluidic systems, such as in systems used to provide drug encapsulation and delivery, may be utilized (see, for example, M. Staples et al.: Pharm. Res., 23, 847 (2006); J. T. Santini et al.: Angew. Chem. Int. Ed. 39, 2396 (2000); J. H. Prescott et al.: Nat. Biotech. 24, 437 (2006), U.S. Pat. No. 7,455,667(B2), each of which is incorporated herein by reference in its entirety).

Figure 2B:
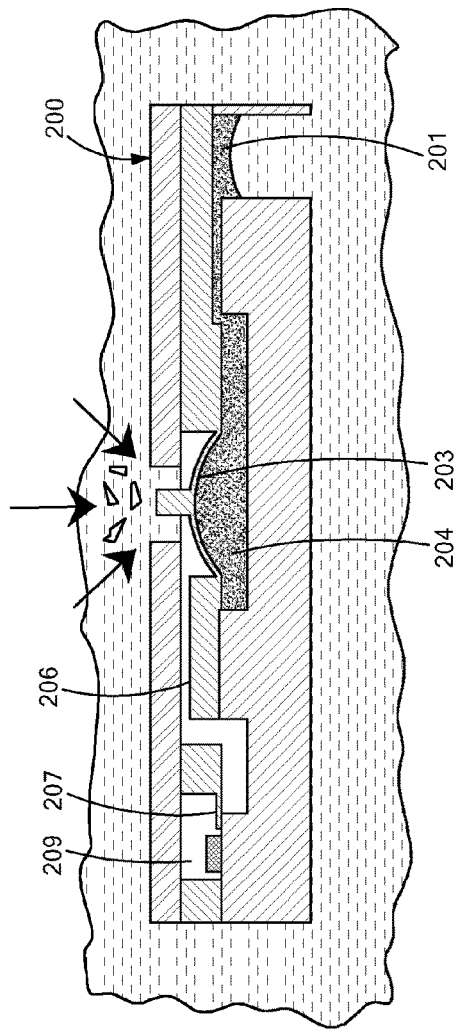
FIG. 2(b) shows the device with the isolation membrane collapsed.

FIG. 2(b) shows the device 200 with the mechanical structure 205 collapsed after applying pressure to the timing fluid 201 (and after the time delay). The collapse of the mechanical structure 205 allows external downhole fluid to enter a sample chamber 209 via an isolated cavity/communication channel 206. The sample chamber 209 may be pre-vacuumed or hold a gas prior to deployment of the device 200. A particle filter may be placed within the isolated cavity/communication channel 206 to filter any contaminants. Note that prior to collapse of the mechanical structure 205, the isolated cavity/communication channel 206 is typically inaccessible to the exterior environment. In other embodiments, the mechanical structure 205 may allow partial/filtered access to the isolated cavity/communication channel 206 prior to its collapse.

FIG. 2(c) shows the device 200 with the sample chamber 209 filled with sample fluid. An integrated one-way valve 207 (i.e., a check valve), may assure sample isolation from the external environment. An example of a micro-fabricated one-way valve is described in the following documents: S. Beeby, G. Ensel, M. Kraft: *MEMS Mechanical Sensors*, Artech House, Boston Mass. (2004); and K. W. Oh et al.: J. Micromech. Microeng., 16, R13-R39 (2006), each of which is incorporated herein by reference in its entirety.

The timing mechanism, the sampling mechanism, and/or in various embodiments, the entire device, may be electrically passive such that it does not include any powered electronic components (e.g., an electronic power source, transmitter, amplifier etc . . . ). In various embodiments, the timing mechanism, the sampling mechanism, and/or the entire device may be void of any active or passive electronic components.

The passive microfluidic timing mechanism may be based, at least in part, on the fact that the flow rate f of a Newtonian fluid through a capillary of roughly circular cross-section is proportional to the difference in pressure $\Delta P$ between the ends of the capillary multiplied by the fourth power of the hydraulic radius R, and is inversely proportional to the viscosity of the fluid $\eta$ multiplied by the length of the capillary l: $f = \pi \cdot \Delta P \cdot R^4 / (8 \cdot \eta \cdot l)$. In other embodiments, if the capillary is chosen to have a rectangular cross-section with width w and height h<w, the flowrate f can be calculated with the approximate formula: $f = (1 - 0.63 \, h/w) \cdot \Delta P \cdot w \cdot h^3 / (12 \cdot \eta \cdot l)$. Such formulae may be found in the literature, for example in the following documents: Stone, H., Stroock, A., and Ajdari, A., "Engineering Flows in Small Devices," Annual Review of Fluid Mechanics, Vol. 36, 2004, p. 381 and D. E. Angelescu: "Highly Integrated Microfluidics Design", Artech House, Norwood Mass. USA (2011), each of which is incorporated herein by reference in its entirety.

If an empty cavity of known volume (i.e., the timing cavity 204) is separated from a high-pressure fluid by a capillary of appropriate geometry, the time required to fill the timing cavity 204 can be accurately determined from knowledge of device geometry, fluid viscosity and pressure differential. Assuming the timing fluid 201 has known characteristics, and that the pressure/temperature history is recorded, the filling time of the timing cavity 204 can be fully determined by geometrical device parameters such as timing cavity 204 volume, micro-fluidic channel 202 capillary diameter and length; the fourth power dependence on diameter allows control of the fill-up time over several decades, resulting in a very versatile timing mechanism. A fully characterized timing fluid 201 may be used that advantageously may be immiscible with both hydrocarbons and water. Examples of such timing fluids include, without limitation, various silicone oils and fluorinated solvents.

Alternatively, a non-Newtonian fluid with known rheological properties can be used as a timing fluid. In one embodiment, one may use a shear-thinning fluid as a timing fluid, which will result in a flowrate which is very low at low pressures, but increases significantly once the ambient pressure (and hence the shear stress in the microchannel) reaches a certain threshold value. In another embodiment, the timing fluid may be a visco-elastic fluid which behaves as an elastic body at low shear stresses, thus completely blocking flow at low pressures. As the pressure reaches a threshold value (corresponding to the yield stress of the timing fluid), the timing fluid will start flowing. This embodiment allows the passive timing devices described above to be inactive below a certain threshold pressure, thus allowing prolonged storage at a pressure situated below the threshold pressure.

FIG. 2(d) shows the device 200 ready to be interrogated after surface retrieval. The sample fluid stored in the sample chamber 209 remains isolated from the environment by the one-way valve 207, so that various physical and chemical property measurements can be obtained. A sensor 208 may be positioned within, or otherwise operationally coupled to, the sample chamber 209 and/or isolated cavity 206, so as to provide various indications or measurements associated with the sample fluid. In various embodiments, a micro-electromechanical sensor (MEMS) design may provide hermetic encapsulation of sensor components within, for example, the sample chamber 209. The sensor 208 may include a material that chemically reacts with the fluid, and/or an electrode allowing an electrochemical measurement to be performed on the fluid sample.

The above-described timing mechanism in conjunction with passive actuators may thus be used to deploy self-triggering sample acquisition devices/vessels. For deployment within a rock matrix, such devices may be density-matched to an injection fluid by incorporating vacuum cavities of appropriate dimensions, which will facilitate passive deployment by injection as well as device retrieval.

Acoustic Emission and Triangulation

Figure 3A:
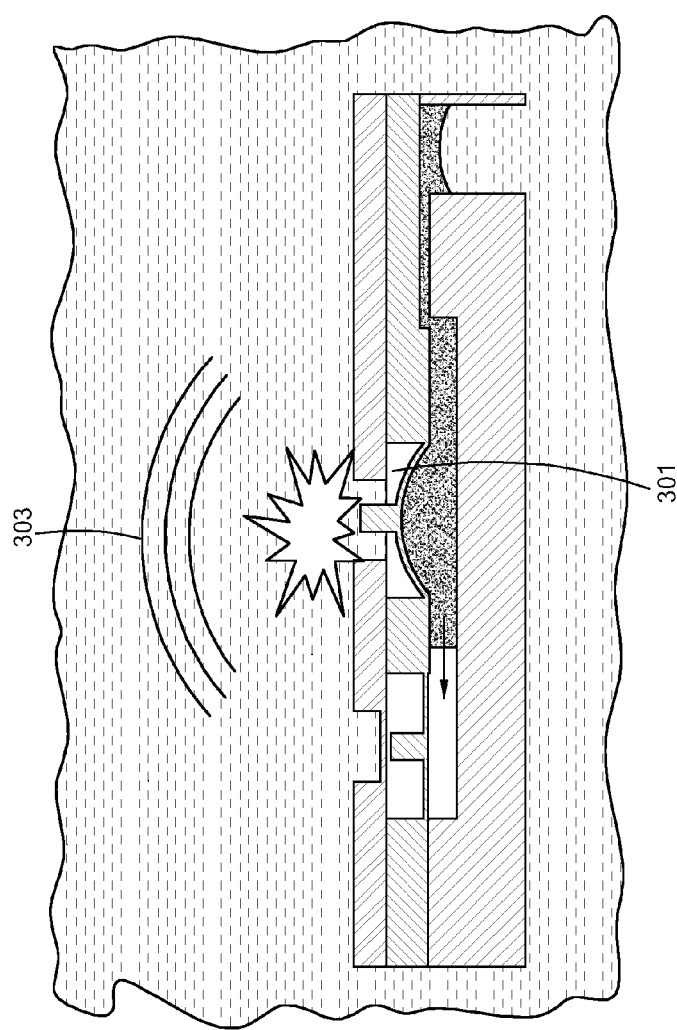
FIG. 3(a) shows a burst of acoustic energy resulting from the rupturing of an isolation membrane, in accordance with an embodiment of the invention.

The above-described device for sample acquisition may be used to generate acoustic signals. For example, in various embodiments the timing mechanism may trigger the piercing of multiple mechanical structures/isolation diaphragms, possibly in sequence. For example, if the cavity behind each isolation diaphragm has volume V (initially under vacuum), upon piercing, these cavities will suddenly collapse and/or rupture, and fill with reservoir fluid at the ambient hydrostatic pressure. The filling of the empty cavity 301 may be very sudden, and will emit a very short burst of acoustic energy 303, as shown in FIG. 3(a), in accordance with an embodiment of the invention. Laboratory studies of collapsing bubbles have been performed by others (for example, A. VOGEL, W. LAUTERBORN, R. TIMM: "Optical and acoustic investigations of the dynamics of laser-produced cavitation bubbles near a solid boundary", J. Fluid Mech., Vol. 206, pp. 299-338 (1989), which is incorporated herein by reference in its entirety), proving that the majority of the bubble energy is emitted into the acoustic transients. The total amount of energy that may be released by sudden filling of a cavity may be roughly estimated as $E = pV$, where p is the reservoir pressure. For an exemplary volume of 1 $mm^3$ and an ambient pressure of 1000 Bar (app. 14500 psi), this corresponds, without limitation, to an emission energy of 100 mJ in a time interval of approximately a fraction of a thousandth of a second to a few thousandths of a second. This corresponds to an acoustic power of over 10-1000 W during each collapse event. Such acoustic emission can then be detected and recorded using remote microphones, hydrophones, geophones, accelerometers or other types of sensors or recorders.

The timing mechanism may trigger several acoustic events in sequence, with the time delay between consecutive collapses defined by the geometry of the associated microfluidic channel and timing cavity. Each device and/or sampling mechanism may be built with a different timing sequence, or with different geometrical parameters, to provide a unique acoustic signature. Such devices may also be realized without a sampling cavity, with the sole purpose of emitting a sound at a time determined by the microfluidic timing mechanism.

Figure 3B:
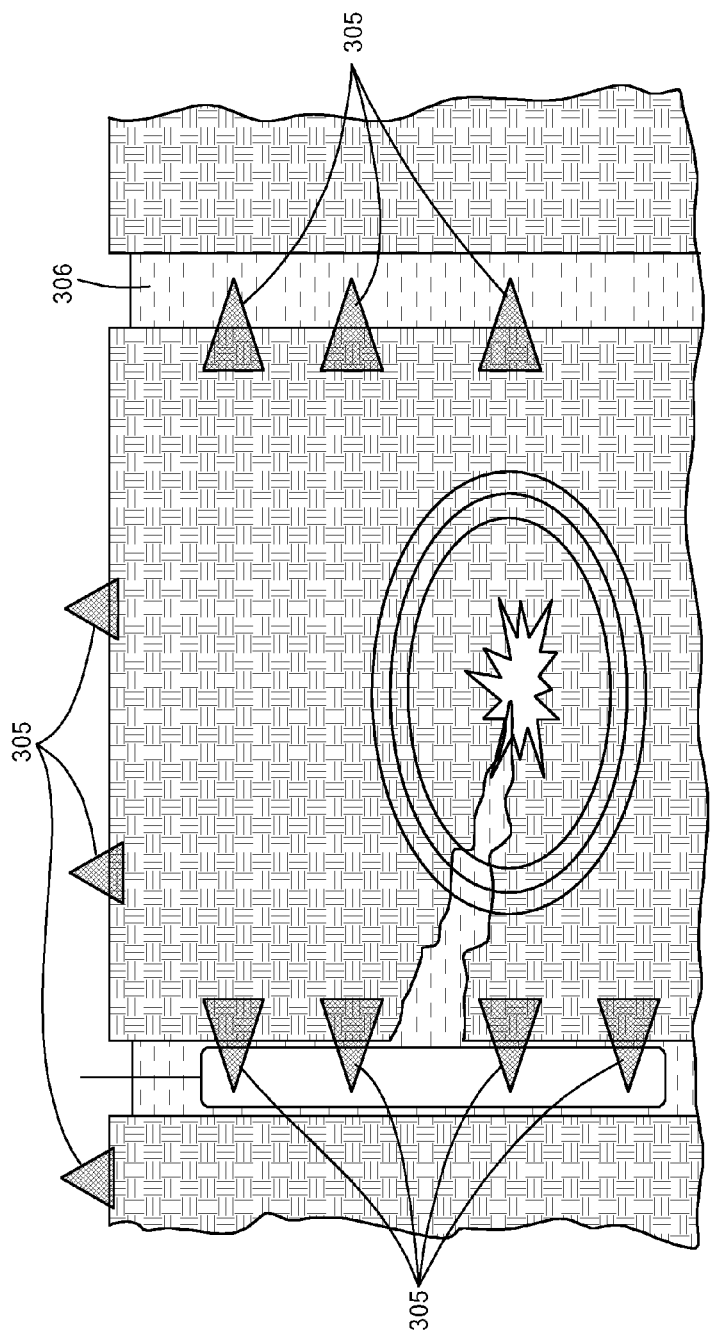
FIG. 3(b) shows multiple microphones placed at different positions in the formation, for recording the arrival time of the wavefronts caused by ruptured isolation membranes, in accordance with an embodiment of the invention.

The acoustic emission for each collapse event will create an acoustic wavefront 303 which will propagate through the fluid and the surrounding rock matrix. The velocity of the wavefront will typically be equal to the sound velocity in the fluid, or in the rock matrix. By placing multiple microphones 305 at different positions in the formation, as shown, for example, in FIG. 3(b), the arrival time of the wavefronts at each microphone 305 may be determined. Based on the time delays between the arrival of the acoustic signal at the different microphones, combined with a knowledge or an educated estimation of the sound velocity in the medium, the position of the smart vessel can then be determined, using, without limitation, triangulation, similar to an underground GPS system, or using compressional/shear signal processing. The time of the sample acquisition may also be recorded. It is noted that FIG. 3(b) is by no way limited to the shown configuration of microphones or devices. In other embodiments of this invention, additional microphones may be located on the ground around the well, or at other subterranean locations, such as in a nearby well 306, cavities, or holes.

Usage as Vehicle for Time-release of Particles, Chemical products, or Pharmaceutical Products The above-described devices may be used as vehicles for transport and time-release of, without limitation, micro- and nano-particles, chemical and/or pharmaceutical products, by including the products or particles within the isolated cavity and/or sampling chamber separated by the mechanical structure (e.g., isolation diaphragm). The timing mechanism may trigger the piercing of the isolation diaphragm after a time delay as described above, at which point the fluid surrounding the device penetrates within the cavity behind the isolation diaphragm and comes in contact with the particles, chemical and/or pharmaceutical products. The particles or products may then dissolve within, or mix with the fluid surrounding the device, thus releasing said particles or chemical or pharmaceutical products into the surrounding environment.

Said particles or chemical products or pharmaceutical products may include, without limitation, chemicals for sanitizing water or other fluids; fluorescent chemicals that may be used as flow tracers; various chemical reagents and chemical cleaning agents; pharmaceutical products such as medications or drugs; various types of nutrients; micro- or nano-particles to be used as flow tracers; materials that react in an aggressive way with the environment, such as by producing an explosion or a rapid release of energy; and/or chemically-functionalized micro- and nano-particles which can react to some environmental parameter.

In accordance with an embodiment of the invention, a passive timing device such as the one previously described may be injected into a geological formation or in a hydraulic fracture by means of pumping via an injection well. When the timing mechanism triggers the piercing of the isolation membrane, functionalized nanoparticles are released within the geological formation as described above. The nanoparticles react with the local environment, are carried by flow towards the injection well, and are retrieved from the well at the surface. The nanoparticle size may be chosen to be substantially smaller than the average pore throat diameter, which will insure that the particle will be transported by flow within the geological formation without clogging the pores. By analyzing the particles after retrieval at the surface, one will be able to infer information about the environment within the geological formation at the time of nanoparticle release. By injecting multiple such passive timing devices which are triggered at different times, one may be able to continuously monitor one or several parameters at multiple remote locations within the geological formation, which may be otherwise inaccessible.

FIG. 4 shows a passive timing device 404 that includes, without limitation, a pharmaceutical product 403 that is released within a human body 405, in accordance with an embodiment of the invention. The isolation diaphragm(s) is pierced at times set by the passive timing device, whereupon the corresponding pharmaceutical products 403 positioned, without limitation, within the isolated cavity and/or sampling chamber, are released within the human body. Multiple devices with one or more diaphragms may be utilized. Using such a system, complete treatment plans may be delivered without any active intervention, by adjusting the timing parameters and the types and quantities of pharmaceutical products within each cavity.

The device 404 may be attached to the skin of the human body 405, or may be implanted within the body. An external source of pressure, or an external pump, may be used to drive the timing fluid within the timing cavity of the device 404. In one embodiment, such external source of pressure may be, without limitation, a pressurized gas cartridge.

FIG. 5 shows a passive timing device that includes a filter 502 for containing the broken diaphragm particles, in accordance with an embodiment of the invention. Upon piercing of the mechanical structure (e.g., isolation diaphragm), the filter 502 advantageously prevents the broken diaphragm particles from passing into the external fluid, while still allowing, for example, a pharmaceutical product 501 to freely pass through. This embodiment may be particularly important if the passive timing device is going to be included within a human body.

Tool Implementation

The above-described devices may also be integrated within downhole sampling and measurements tools, such as the Modular Formation Dynamics Tester (MDT) produced by Schlumberger, the Formation Multi-Tester (FMT) produced by Baker Hughes or the Sequential Formation Tester (SQT) produced by Halliburton, or any other similar tool. Arrays of the sampling devices, integrating a plurality of devices and/or sampling mechanisms on a single microfabricated substrate, may be incorporated within the tool architecture. The above-described devices may also be integrated in production logging oilfield tools, possibly in slickline tools.

Figure 6:
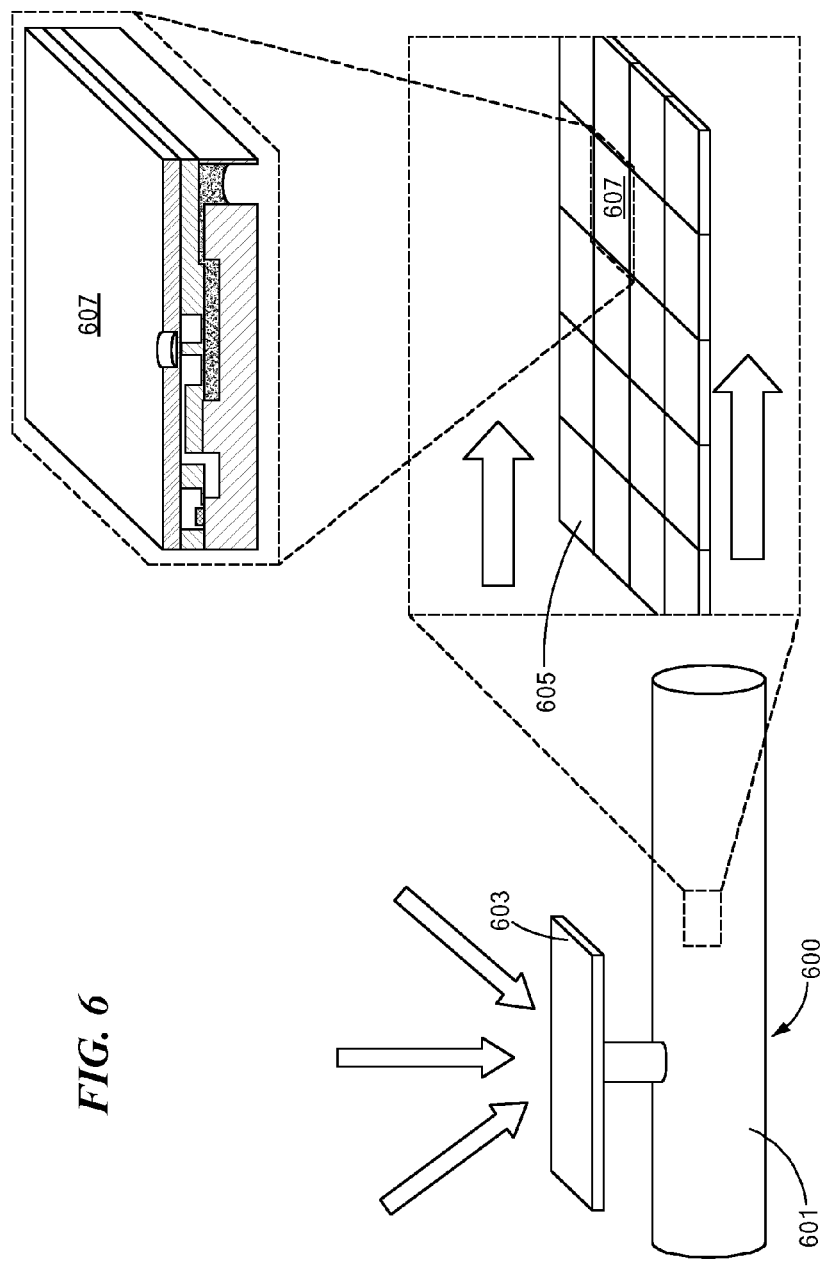
FIG. 6 shows integration of a plurality of sampling devices and/or mechanisms within an oilfield-sampling tool, in accordance with an embodiment of the invention.

FIG. 6 shows integration of a plurality of sampling devices and/or mechanisms 605 within an oilfield-sampling tool such as a MDT, a FMT or a SFT, in accordance with an embodiment of the invention. The tool 600 pushes a pad 603 into the geological formation wall, and pumps the formation fluid into an internal flow-line 601, where the fluid comes into contact with a smart sampling device array 605. Each device 607 may acquire a sample, perform a measurement, and/or emit an acoustic signal which is recorded by a microphone within the tool. The recorded acoustic signals may provide, for example, the precise time when each measurement was performed and may uniquely identify the device which performed the measurement.

The device 607 may come into contact with the formation fluid as it is pumped into the tool flowline 601. The acoustic emission events may be recorded using a microphone implemented in the tool, and later analyzed at the surface to infer the precise time of sample acquisition for each of the smart vessels in the array, thus providing very valuable time-series data.

Figure 7:
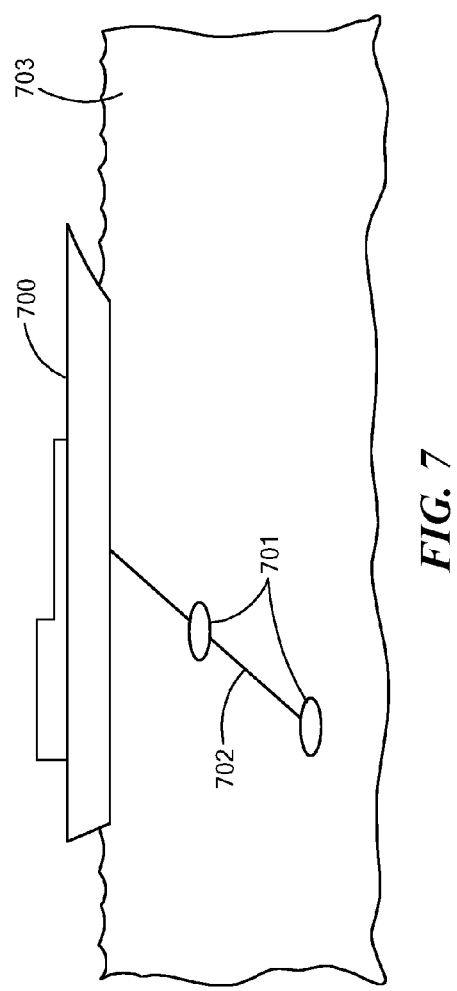
FIG. 7 shows an array of smart sampling devices embedded within an underwater measurement system which may be attached with a cable to either a buoy, a rig, a vessel or a ship, in accordance with an embodiment of the invention.

FIG. 7 shows another embodiment of the invention, where an array of smart sampling devices is embedded within a submarine measurement system 701, which may be attached with a cable 702 to, without limitation, either a buoy, a rig, a submarine, a vessel or a ship 700. The measurement system 701 may either be positioned in a stationary manner in the body of water 703, at a depth dependent, without limitation, on the length of the cable 702, or it may be dragged through the body of water by the ship 700. The smart sampling devices in the measurement system 701 perform sample acquisitions and measurements at times determined by their respective timing mechanisms, thus providing a time-series or a spatial map of measurements at a given depth.

Viscosity Measurement

FIG. 8A shows a viscosity measurement system that may be fully passive, in accordance with an embodiment of the invention. The system 801 illustratively includes two devices 805 and 806 connected together in series, in such a way that the first device's isolated cavity 802 is connected, via a conduit, such as a microfluidic channel or other type of tube of controlled dimension 803, to the timing cavity 804 of the second device. After the rupture or collapse of the first device's mechanical structure 807, the second device's timing cavity 804 will start filling with external fluid 808. The filling time of the second device's timing cavity 804, and the corresponding rupture or collapse of the second device's mechanical structure 809, may depend, at least in part, on the geometry of the conduit 803, on external pressure, and/or on the viscosity of the external fluid 808. By controlling, for example, the geometrical parameters, and by measuring external pressure, one can relate the viscosity of the external fluid to the time measured between the rupture or collapse of the first sampling device's mechanical structure 807 and that of the second device's mechanical structure 809. This allows an accurate viscosity measurement to be performed on the external fluid.

More particularly, providing that the conduit 803 has hydrodynamic resistance Rh, the external fluid has pressure P, and the timing cavity 804 has volume V, the filling time t of cavity 804 will be given by $t = Rh \times V/P$. The hydrodynamic resistance of a circular channel of radius R and length L is given by $Rh = 8 \times n \times L / (\pi \times R^4)$. The hydrodynamic resistance, for a rectangular conduit of lateral dimension h≪w and length L, can be approximated as $Rh = 12 \times n \times L / (h^3 \times w \times (1 - 0.63 \times h/w))$, where n is the viscosity of the external fluid (see, for example, D. Angelescu "Highly Integrated Microfluidics Design", Artech House 2011). By measuring the filling time of the cavity 804, therefore, one can infer the value of the hydrodynamic resistance of the conduit 803, and knowledge of the geometrical details of this conduit allows a determination of the fluid viscosity n from the above formulas: $n = t \times P \times \pi \times R^4 / (8 \times L \times V)$ for a circular conduit, and, respectively, $n = t \times P \times h^3 \times w \times (1 - 0.63 \times h/w) / (12 \times L \times V)$ for a rectangular conduit.

In accordance with further related embodiments, the viscosity-measurement device described in the above paragraph may incorporate means of controlling and/or measuring the external fluid pressure, and of recording the time between the collapse of the first device's and the second device's mechanical structures 807 and 809. The collapse of a device's mechanical structure may be detected acoustically (by detecting the acoustic signature emitted during the collapse), electrically (by recording a disruption to an electrical circuit caused by the collapse), or optically (by observing the collapse using a camera, or another type of optical system), or by any other means known to a person skilled in the art.

FIG. 8B shows another embodiment of the viscosity-measurement device incorporating an additional device 810 connected in series with devices 805 and 806 in such a way that the isolated cavity of device 806 is connected to the timing cavity of the device 810 by a second conduit 811 of controlled geometry. This second conduit 811 may have different cross-section and length from the first conduit 803, thus resulting in a different timing fluid flowrate into the timing cavity 812 of the device 810.

This difference in geometry between conduits 803 and 811 may be used to extend the measurement range of a device and measure different ranges of fluid viscosity using the viscosity-measurement device. In one embodiment, the geometry of conduit 811 may be chosen so that the filling time of cavity 812 is much longer than the filling time of cavity 804 (in case we assume equal volumes for the timing cavities 804 and 812, this corresponds to the conduit 811 having significantly higher hydrodynamic resistance than conduit 803). If viscosity of the external fluid is very low, and the filling time of the cavity 804 is too short to enable an accurate measurement, then a much more accurate measurement of viscosity may be obtained by using the filling time of cavity 811. On the other hand, for highly viscous fluids, the filling time of cavity 804 may provide a reasonably accurate measurement, such that waiting for the filling of cavity 811 may no longer be necessary. Additional devices may be connected in series, with conduits connecting the isolated cavity of one device to the timing cavity of the next, to further extend the range of accurate viscosity measurements.

Manifold Sampling and Chemical/Biochemical Measurement Device

FIG. 9A shows a sampling and measurement system 901 that includes multiple devices 902, 903 connected, via a manifold 904, to an external sampling conduit 905, in accordance with an embodiment of the invention. Upon a new sample being acquired by one of the devices, new fluid may be drawn through the sampling conduit 905. The sampling chambers 906, 907 for the devices 902, 903 may be designed with volumes such that the dead volumes within the system, the internal volume of the conduit 905 or the volume of the connecting manifold 904 be negligible in comparison to the volume of the sampling chambers 906, 907.

The sampling conduit 905 may be connected to a pipe, a fluid reservoir, or another external fluid supply 908 that needs monitoring. Each time a new sample is acquired by one of the devices 902, 903, the respective volume of fluid is drawn from the said fluid supply 908, through the conduit 905 and manifold 904, into the sampling chamber of the active device.

Each sampling chamber 906, 907 may be, without limitation, a vial, a bottle and/or another leakproof container/receptacle. One or more sampling chambers 906, 907 may include a pre-measured amount of chemical or biological reagent 909, or a combination of several such reagents 910 in liquid, solid, powder or lyophilized form, in free form or immobilized on a solid substrate. Upon sample entering the sampling chamber 906, 907, a sequence of chemical or biological reactions occur between the sample and the said reagents. Different sampling chambers 906, 907 within the same system may contain different reagents 909, 910.

In various embodiments of the invention, said chemical or biological reactions may have a visible outcome. For example, the coloration of the solution or of an immobilized reagent may change, there may be a change in turbidity, there may be a development of fluorescence, or any combination of the above.

The visible outcome may be recorded in-situ, by performing an optical measurement via, without limitation, the vial wall or via an optical window 911 embedded in the sampling chamber 907. The optical measurement may include, without limitation, acquiring an image of the sampling chamber using an external optical instrument 912 such as color or black and white camera, a spectrophotometer, a fluorescence detection device, a Raman scattering device, and/or a turbidity measurement device.

FIG. 9B shows an external sampling conduit connected, via a T-junction 913, to a reagent reservoir 914, in accordance with an embodiment of the invention. The reagent reservoir 914 may be substantially at the same pressure as the fluid being sampled. For example, and without limitation, the reagent reservoir 914 may be a bladder submerged into the external fluid being sampled, or an accumulator. A fluidic resistance 915 may be included between the reagent reservoir 914 and the T-junction 913, such as to limit the flow rate of reagent. Each time a sample is drawn in, a proportional amount of reagent is drawn in along with the sample, the mixing ratio being set passively by the said fluidic resistance.

The external sampling conduit may include a micromixer 916 downstream from the T-junction 906, 907, such that the combined sample and reagent stream is thoroughly mixed after passing through the micromixer 916.

In various embodiments of the invention, the external sampling conduit may include a microfluidic sensor 917, such that each time a sample is acquired by one of the devices, the microfluidic sensor 917 performs a measurement on the fresh stream of fluid. The measurement may include, without limitation, an optical measurement (e.g., index of refraction, absorbance, fluorescence), an electrical measurement (e.g., conductivity, resistivity, dielectric constant), an electrochemical measurement (e.g., ionic content, chemical composition), a physical measurement (e.g., viscosity, density), a chemical measurement (chemical composition), and/or biological measurement (cell count).

Preconcentration and/or Sample Filtering

FIG. 10A shows a device 1001 that may be used to sample from an external fluid contaminated with one or a combination of particles 1003, organic pollutants, biological pollutants, chemical pollutants, plankton, phytoplankton, nuclear matter, volatile organic compounds, pharmaceutical matter, or other contaminants, in accordance with an embodiment of the invention. The device 1001 includes one or more integrated filters 1002 that the sample has to come in contact with, upon or prior to entering the sampling chamber 1004. The filter 1002 may include, without limitation, one or a combination of the following: a mechanical filter, a solid phase extraction column, a packed column, a hydrocarbon filter, a gas chromatography preconcentrator, a filter to collect and concentrate radioactive material, a biological filter, an absorbent medium, a scavenging medium, a hydrophobic material and a hydrophilic material.

FIG. 10B shows the device 1001 after sampling, the filter 1002 having collected different components present in the fluid sample, such as, without limitation: particles 1003, organic pollutants, biological pollutants, chemical pollutants, plankton, phytoplankton, nuclear matter, volatile organic compounds, pharmaceutical matter, or other contaminants.

The filter 1002 may, optionally, be later retrieved and analyzed, to provide time-series data concerning the contaminant of interest at the location of the device. Analyzing the filter 1002 may require backflushing, thermal desorption or solvent washing, and/or other techniques to remove the adsorbed, absorbed, or trapped contaminants. Analysis may require analytical techniques such as, without limitation, GC/MS, HPLC, gamma ray spectroscopy. In various embodiments, the filters may be analyzed in-situ.

Maintaining Sample Integrity by Controlled Sampling and High-Pressure Preservation FIGS. 11A-C shows a system 1101 capable of acquiring a sample from an external fluid 1102, pressurizing it at a pressure higher than the pressure of the external fluid, and maintaining it at such pressure for extended periods of time, in accordance with an embodiment of the invention. Such a system 1101 advantageously may ensure that the sample will remain in single-phase configuration and will not undergo a thermodynamic transition to a multi-phase fluid. This is particularly important when sampling hydrocarbon fluid from a geological formation during oilfield drilling, wireline logging, or production operations, since the sample needs to remain in single phase throughout the transport to the analysis laboratory.

The system 1101 shown in FIG. 11A includes a sampling chamber 1104 divided into a first portion and a second portion, in accordance with an embodiment of the invention. The isolated cavity of a first device 1103 is connected via a conduit to the first portion of the sampling chamber 1104. The second portion of the sampling chamber 1104 is connected via a conduit 1107 to an isolated cavity 1106 of a second device 1105. The mechanical structure 1111 of the second device 1105 may be, without limitation, scheduled to open at a later time relative to the mechanical structure 1110 of the first device 1103. The first portion of the sampling chamber 1104 may be separated from the external fluid by a first check valve 1108, allowing fluid to enter the sampling chamber 1104 but not to leave it. The connection between the two portions of the sample chamber 1104 may include a second check valve allowing flow from the second portion of the sampling chamber 1104 to the first portion of the sampling chamber 1104, but preventing flow in the opposite direction. The first and second portions of the sampling chamber 1104 may be separated by, without limitation, a leakproof piston 1109 or a flexible membrane, allowing for the pressures in the first and second portions to be equalized without requiring physical contact of the fluids in the two portions. The mechanical structure 1110 of the first device 1103 may be connected to the fluid to be sampled 1102, with the mechanical structure 1111 of the second device 1105 connected to a pressurized fluid reservoir 1112 at a pressure that is higher than the external pressure. The pressurized fluid reservoir 1112 may incorporate, without limitation, an accumulator, a pressurized gas container, and/or a mechanical spring.

FIG. 11B shows the system 1101 with the timing fluid cavity 1113 of the first device 1103 filled with timing fluid, causing the rupture or collapse of the first device's mechanical structure 1110, and allowing the external fluid 1102 to enter the first portion of the sampling chamber 1104.

FIG. 11C shows the subsequent rupture or collapse of the second device's mechanical structure 1114, the fluid from the pressurized reservoir 1112 entering the second portion of the sampling chamber 1106 and applying its pressure, via the piston 1109, to the sample contained in the first portion of the sampling chamber 1104. The fluid in the first portion of the sampling chamber 1106 is prevented from leaving the chamber by the check valve 1108, and therefore is maintained at a pressure higher than the pressure at which it was acquired.

FIG. 12A shows a device 1201 for performing a sampling operation from a high-pressure external fluid 1202 without significantly lowering the pressure of the external fluid during the sampling process (without "shocking" the fluid), in accordance with an embodiment of the invention. The sampling chamber 1203 may include a leak-proof piston 1204 or flexible membrane that separates it into a first portion 1205 and a second portion 1206. The second portion 1206, which is farther away from the mechanical structure 1210 may be pre-filled with a secondary liquid 1207 and is connected, via a conduit 1208, such as a microfluidic channel and/or fluidic constriction, to another auxiliary chamber 1209. The conduit 1208 may include a check valve 1212 or backpressure regulator that assures that the fluid 1207 does not leak from the second portion 1206 to chamber 1209 prior to sample acquisition. Upon the collapse of the mechanical structure 1210, the sample enters the first portion 1205 of sampling chamber 1203 and applies pressure to the piston 1204, which moves at a slow rate controlled, for example, by the viscosity of the secondary liquid 1207 and the geometry of the conduit 1208.

In another related embodiment, the auxiliary chamber 1209 may be pre-filled with pressurized gas. Upon sample acquisition, the gas is compressed, forming a cushion that will keep the secondary liquid 1207, and consequently the sample, pressurized. The sample in the first portion 1205 of the sampling chamber 1203 is prevented from leaving by the check valve 1211, and therefore is maintained at a pressure that is comparable to the pressure at which it was acquired.

In another related embodiment, the sampling chamber may include a compressed spring and a piston, one side of the piston in contact with the sampling chamber and the other side in contact with the external fluid, such that prior to sampling being initiated the spring is compressed by the piston due to external fluid pressure being applied to the piston. Upon sampling being initiated, the hydrostatic pressure on both sides of the piston equalizes and the elastic force of the spring displaces the piston, thus acquiring a sample at controlled speed and with minimal change to the overall submerged weight and buoyancy of the device. The travel of the piston may be restricted due to the presence of a mechanical fixture such as a stop or a ridge.

FIG. 12B displays another embodiment of FIG. 12A that in addition to allowing a sampling operation to be performed from a high-pressure fluid without dropping the pressure of the fluid or otherwise "shocking" it during the sampling, also allows the sample to be maintained at a high pressure after sampling, possibly higher than the initial external fluid pressure, thus preventing phase separation. In addition to the details provided above with regard to FIG. 12A (the numbering of which will be maintained), in the system 1213 the second portion 1206 of the sampling chamber 1203 that is farther away from the mechanical structure 1210 is also connected via a conduit 1215 to an isolated cavity 1216 of a second device, which is scheduled to open at a later time. The conduit 1215 may include a check valve 1214 allowing flow from the isolated cavity 1216 to the second portion 1206 of the sampling chamber 1203, but preventing flow in the opposite direction. Positioned between the first portion 1205 and the second portion 1206 of the sampling chamber 1203 may be a piston or a flexible membrane allowing for the pressures to be equalized without requiring physical contact of the fluids in the two portions 1205 and 1206. The mechanical structure 1210 of the first device is connected to the fluid to be sampled 1202, whereas the mechanical structure 1217 of the second device is connected to a pressurized fluid reservoir 1218 at a pressure that is higher than the external pressure. The pressurized fluid reservoir 1218 may incorporate, without limitation, an accumulator, a pressurized gas container, and/or a mechanical spring. Upon the rupture or collapse of the first device's mechanical structure 1210, external fluid 1202 is allowed to enter the first portion 1205 of the sampling chamber 1203, at a slow rate that is controlled, at least in part, by the viscosity of the secondary liquid 1207 and/or the geometry of the conduit 1208. Upon the subsequent rupture or collapse of the second device's mechanical structure 1217, the fluid from the pressurized reservoir 1218 enters the second portion 1206 of the sampling chamber, and applies its pressure to the piston 1204, and consequently to the sample contained in the first portion 1205 of the sampling chamber 1203. The fluid in the first portion 1205 of the sampling chamber 1203 is prevented from leaving the check valve 1211, and therefore is maintained at a pressure higher than the pressure at which it was acquired.

Complex Sample Manipulations, Filter Backflushing, and Transfer Between Vials

FIGS. 13A-D show, in chronological order, operations performed by a system that, in addition to sampling at a time controlled by a passive timing mechanism, integrates a mechanism allowing the subsequent transfer of the sample from an initial sampling chamber to another sampling chamber after a given amount of time, in accordance with an embodiment of the invention. This operation can be further repeated as desired. The system described in FIGS. 13A-D may also integrate different chemical or biochemical reagents in each of the sampling chambers, and/or may integrate a filtration medium that can be back-flushed as part of the sample transfer to another sampling chamber, thus concentrating certain components of the sample.

FIG. 13A shows a system 1306 that includes multiple sampling devices 1301, 1302, 1303, such that a sample from external fluid 1304 may be acquired by a first device 1301 and provided to a first portion of a sampling chamber 1305. The first portion of sampling chamber 1305 may optionally include a filter 1307. The first portion of the sampling chamber 1305 may also integrate an optional first group of chemical or biochemical reagents. The first portion of the sampling chamber 1305 may be separated from a second portion of the sampling chamber 1305 by a piston, or a flexible member membrane. The second portion of the sampling chamber 1305 is in fluidic communication with an isolated cavity 1308 of a second device 1302 that is scheduled to open at a later time. The first portion of the sampling chamber 1305 is also connected, upstream of the optional filter 1307, to the mechanical structure 1312 of a third device 1303 that is scheduled to open after the second device 1302. The mechanical structure 1313 of the second device 1302 is in turn connected to a pressurized fluid reservoir 1314, such as, without limitation, a pressurized gas reservoir, or an accumulator.

FIG. 13B shows the system 1306 after the collapse of the first device's mechanical structure 1309, showing a sample 1310 being acquired into the first portion of the sample chamber 1305, mixing with the optional first reagent of group of reagents, and pushing the piston 1311 into a far position distal the first device's mechanical structure 1309.

FIG. 13C shows the system 1306 after the later collapse of the second device's 1302 mechanical structure 1313. The pressurized fluid from reservoir 1314 enters the second device 1302 and applies its pressure to the backside of the piston 1311. The sample acquired in the first portion of the sampling chamber 1305 cannot backflow into the first device 1301 due to the check valve 1315.

FIG. 13D shows the system 1306 after the later collapse of the third mechanical structure 1312. The sample 1310 contained in the first portion of the sampling chamber 1305 is pushed, by the pressure of the pressurized gas reservoir 1314, into the sampling chamber 1315 of the third device 1303. During this process, the sample is forced to traverse the optional filter 1307 in reverse, thus back-flushing it and transporting the filtered material into the sampling chamber 1315 of the third device 1303. By choosing the volumes of the sample chamber 1315 of the third device 1303 to be lower than the volume of the first portion of sample chamber 1305, a higher concentration of the components filtered from sample 1310 can be obtained in the sampling chamber 1315. The sample chamber 1315 of the third device 1303 may also include an optional second group of chemical or biochemical reagents, such that the sample 1310, after having already reacted with the optional first group of reagents present in the first portion of the sample chamber 1305, now has to react with the optional second group of reagents. The process may be repeated multiple times.

FIG. 13E shows the above-described system 1306 slightly modified, with the sampling chamber 1305 further including a first reservoir 1316 that may be pre-filled with a liquid solution 1317, and a second reservoir 1318 that initially may be empty. The first reservoir 1316 may be separated using a piston 1319 or flexible membrane, or a similar structure, from the second portion of the sampling chamber 1305 that is in fluidic communication with the isolated cavity 1308 of the second sampling device 1302. Optionally, one-way check valves 1320, 1321 may be integrated allowing the fluid to circulate from the filter 1307 into the second reservoir 1318, and, respectively, from the first reservoir 1316 towards the filter 1307. Upon the sample acquisition by the first device 1301, the sample moves through the filter 1307 into the second reservoir 1318. Upon the collapse of the mechanical structure 1313 of the second device 1302, pressure from pressurized reservoir 1314 is applied to the liquid solution 1317 in the first reservoir 1316. As the mechanical structure 1312 of the third device 1303 collapses, the liquid solution 1317 is forced through the filter 1307, and transports the material collected on filter 1307 into the sampling chamber 1315 of the third device 1303. Optionally, a first and a second group of reagents may be incorporated in the first portion of the sampling chamber 1305, and, respectively, in the sampling chamber 1315 of the third device 1303. Additional reagents may be included in the liquid solution 1317 present in the first reservoir 1316.

The operation mode described above allows complex sample preparation, such as, without limitation, mixing with multiple chemical or biochemical reagents, backflushing using a specific liquid solution that is different from the original sample liquid, pre-concentration in a separate vial, and additional chemical and/or biochemical reactions on the preconcentrated sample.

Daisy Chain Configuration of Multiple Sampling Systems

Figure 14:
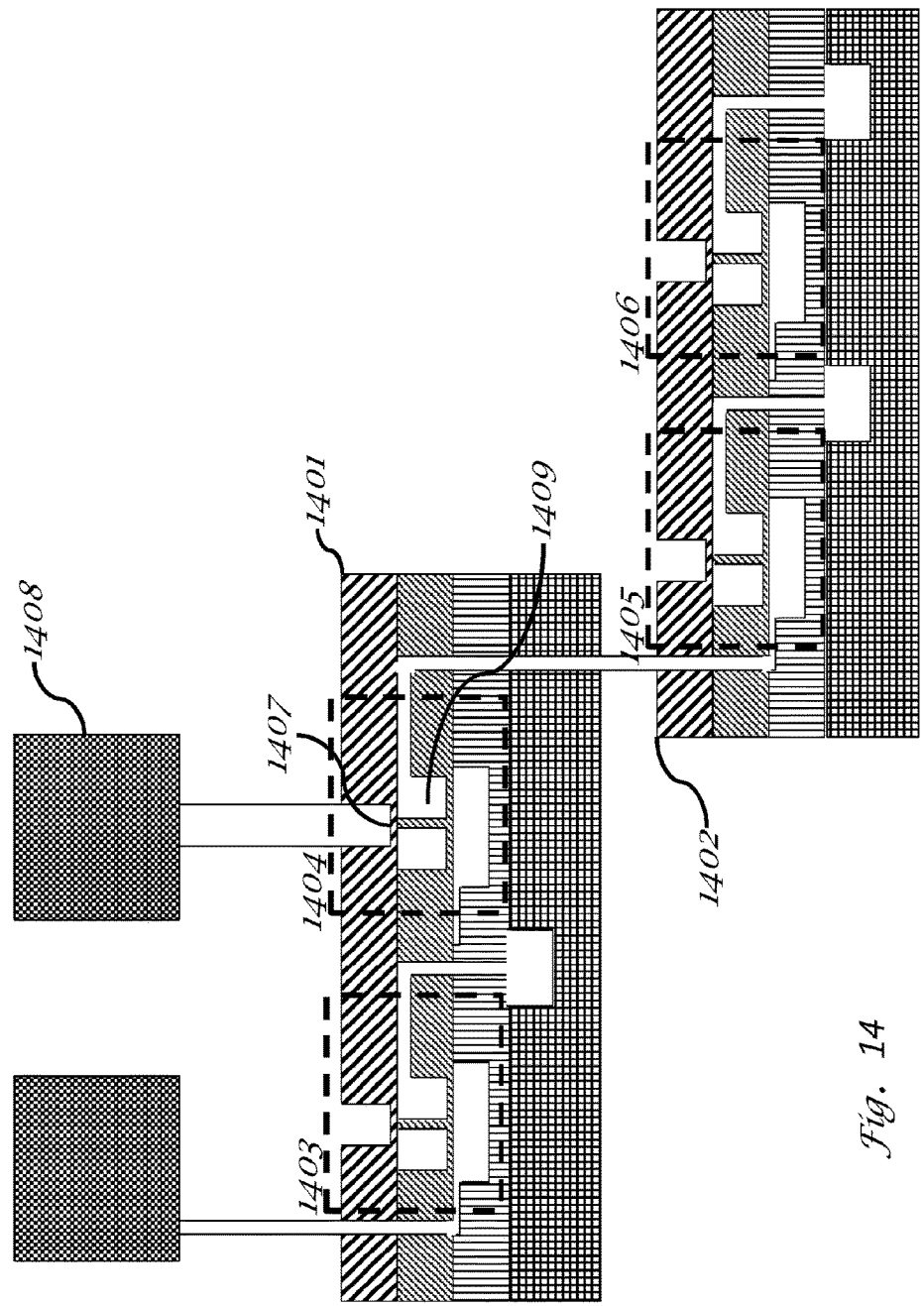
FIG. 14 shows multiple sampling systems connected in a "Daisy-chain" configuration, in accordance with an embodiment of the invention.

FIG. 14 shows multiple systems connected in a "Daisy-chain" configuration, in accordance with an embodiment of the invention. Upon one system acquiring its last sample it automatically triggers the start of sampling using the next system in the daisy chain. This mode of operation can allow an unlimited number of systems to be connected, and thus extends the sample acquisition capacity of the combined system beyond the limits of any single individual system connected in the daisy chain.

Two systems 1401 and 1402, each including a plurality of devices 1403 and 1404, and 1405 and 1406, respectively, are timed to acquire corresponding samples at different times. Illustratively, the mechanical structure 1407 of the last device 1404 of the first system 1401 may be connected to the timing fluid reservoir 1408 of the second system 1402. Additionally, the isolated cavity 1409 of the last device 1404 of the first system 1401 may be connected to the timing mechanism of one or more of the devices 1405, 1406 associated with the second system 1402. In this configuration, the collapse or rupture of the mechanical structure 1407 of the last sampling device 1404 of the first system 1401 triggers the start of the sampling using the second system 1402, thus allowing the systems to be connected in a daisy-chain configuration.

External Control of the Sampling Time

Figure 15:
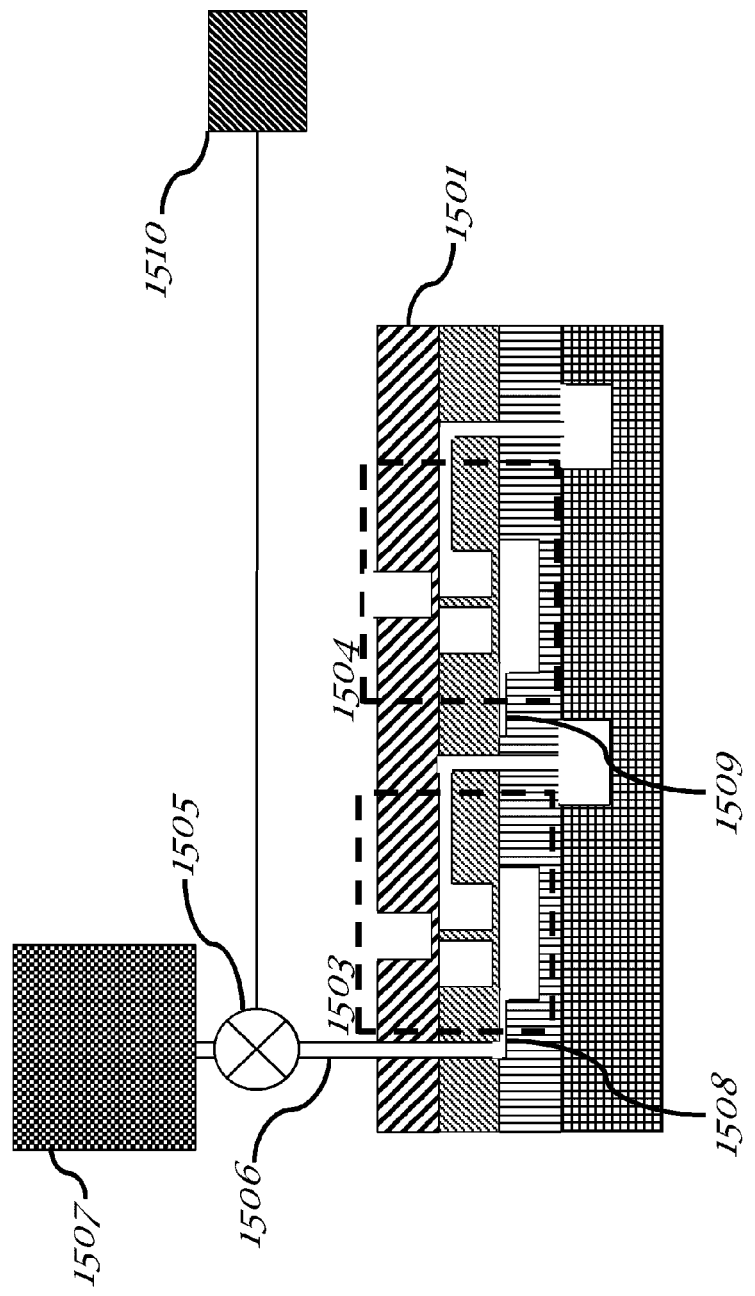
FIG. 15 shows a system capable of controlling the sampling times of a plurality of sampling devices using a trigger device, in accordance with an embodiment of the invention.

FIG. 15 shows a system 1501 capable of controlling the sampling times of a plurality of sampling devices 1503 and 1504 using a trigger device 1505 that may be in the form of a fluid control device. The trigger device 1505 may be placed, without limitation, on a timing fluid line 1506, between an optional pressurized timing fluid reservoir 1507 and the timing channels 1508, 1509 of any number of the multiple timing devices 1503, 1504 associated with the system 1501. The trigger device may be controlled by a control unit 1510 that may either be a subsystem of system 1501, or an external, possibly remote, system.

The pressurized timing fluid reservoir 1507 may be absent, instead the timing fluid may be maintained at a pressure equal to the external fluid being sampled. The trigger device 1505 can be any type of device that can enable or disable the passage of timing fluid as desired. The trigger device 1505 may be one of a check valve, an electrically-controlled solenoid valve, a fluidic switch, or any other type of active valve known in the art. The trigger device 1505 may also include a one-shot valve, that initially blocks the passage of timing fluid, and upon receipt of an external signal from the control unit 1510 permanently opens the passage of timing fluid without requiring further power.

In accordance with further embodiments, the system 1501 may incorporate a recording mechanism that records that a sample has been acquired, and/or of transmitting this information to either an external system, to the control unit 1510, or both. The collapse or rupture of the mechanical structure and the subsequent sample acquisition may be detected acoustically (by detecting the acoustic signature emitted during the collapse), electrically (by recording a disruption to an electrical circuit caused by the collapse), optically (by observing the collapse using a camera, or another type of optical system, or by observing an optical change to a vial being filled with fluid), or by any other means known in the art.

Passive Timing and Sample Acquisition Implemented Using a Piston Assembly

In certain applications, using a timing diaphragm inside a sampling mechanism may not be convenient or ideal. Instead it may be advantageous to use a different type of moving part that is capable of achieving a good fluidic seal.

FIGS. 16A and 16B show a sampling device 1600 that is configured to acquire a sample from an external fluid 1601, in accordance with an embodiment of the invention. The sampling device 1600 includes a mechanical structure 1602 that is in contact with the external fluid 1601. The sampling device 1600 further includes an isolated cavity 1611. A piston 1604 is positioned, without limitation, within the isolated cavity 1611, and is configured to move within said cavity 1611. In various embodiments, the piston 1604 separates said cavity 1611 into two portions that are not in fluid communications because of a sliding seal 1605. The sliding seal 1605 may be, for example, an o-ring or any other type of seal known in the art that performs a sealing function while allowing the piston 1604 to slide. The sampling device 1600 may further include a timing cavity 1616 in fluid communication with one side of the piston.

The sampling mechanism may further include a conduit 1615 that may be, without limitation, a microfluidic channel or a capillary tube, and that may have a predefined geometry. Upon applying pressure to the timing fluid 1609 (which may be a liquid or a gas), said timing fluid 1609 flows within the conduit 1615 at a rate, for example, that may be dictated by the applied pressure, the predefined channel geometry and known timing fluid properties. Upon reaching the timing cavity 1611 and filling it after a timing interval, the timing fluid 1609 applies pressure to one side of the piston 1604, which advances within the isolated cavity 1611 (alternatively called a piston cavity).

The piston 1604 may also include a piercing structure, such as a protrusion 1603, which may be, without limitation, in the form of a needle, a pin, a raised boss, or any other type of structure known in the art. The protrusion 1603 may be separate from the piston 1604 or an integral part of it. Upon the piston 1604 sliding far enough into the isolated cavity 1611, the protrusion 1603 contacts the mechanical structure 1602 and transmits and/or concentrates mechanical stress onto the mechanical structure 1602.

Under the effect of said stress, the mechanical structure 1602 is pierced and the mechanical structure 1602 is destroyed, such as by, without limitation, rupturing or by collapsing, allowing the external fluid 1601 to enter the isolated cavity 1611, which may then further lead to a sampling chamber 1607. The isolated cavity 1611 and the sampling chamber 1607 may be part of the same assembly as the sampling mechanisms, or they may be separate parts that are connected using some form of fluidic or mechanical fixture known to the person skilled in the art, such as a tube, a channel, or a pipe 1608. Prior to entering the sampling chamber 1607, the external fluid 1601 may pass through a check valve 1606 that allows fluid to flow into the sampling chamber 1607 but prevents the fluid 1601 from flowing in the opposite direction.

The timing fluid 1609 may further be in fluidic communication via, without limitation, a tube 1610, a channel, or a pipe, or any other type of fixture or device, that allows fluidic communication with a pressurized timing fluid reservoir 1613. In some embodiments, the timing fluid reservoir 1613 may be at a pressure that is equalized with the pressure of the external fluid 1601. In other embodiments, the timing fluid 1609 may be the same fluid as the external fluid 1601. The tube 1610 may be optionally connected to an on/off valve 1612, which may be manually operated or controlled by an optional control device 1614.

The control device 1614 and the valve 1612 may be electrically active. The control device 1614 may be triggered remotely. The triggering action in itself may be transmitted to said control device 1614 via a mechanical, acoustical, electrical or electromagnetic wired or wireless link. For example, the triggering action may be transmitted to the control device 1614 using, without limitation, a mechanical cable or lever, a serial communication cable, a parallel communication cable, an electrical triggering cable, an electromagnetic wave using a mobile telephony network or a radio frequency or satellite connection, a pressure wave such as an acoustic or sound wave using an acoustic module (such as sonar and/or a hydrophone, a speaker and a microphone, or similar), or any other form of acoustic, electrical, electromagnetic, acoustic or mechanical communication and/or triggers known in the art.

FIG. 16B shows the sampling device 1600, after the piston 1604 has moved under the effect of pressure from the timing fluid 1609, and the protrusion 1603 of the piston 1604 has pierced the mechanical structure 1602. Sample chamber 1607 is shown filled with external fluid 1601.

Triggered Sampling Implementation With Different Passive Timing Durations

Figure 17:
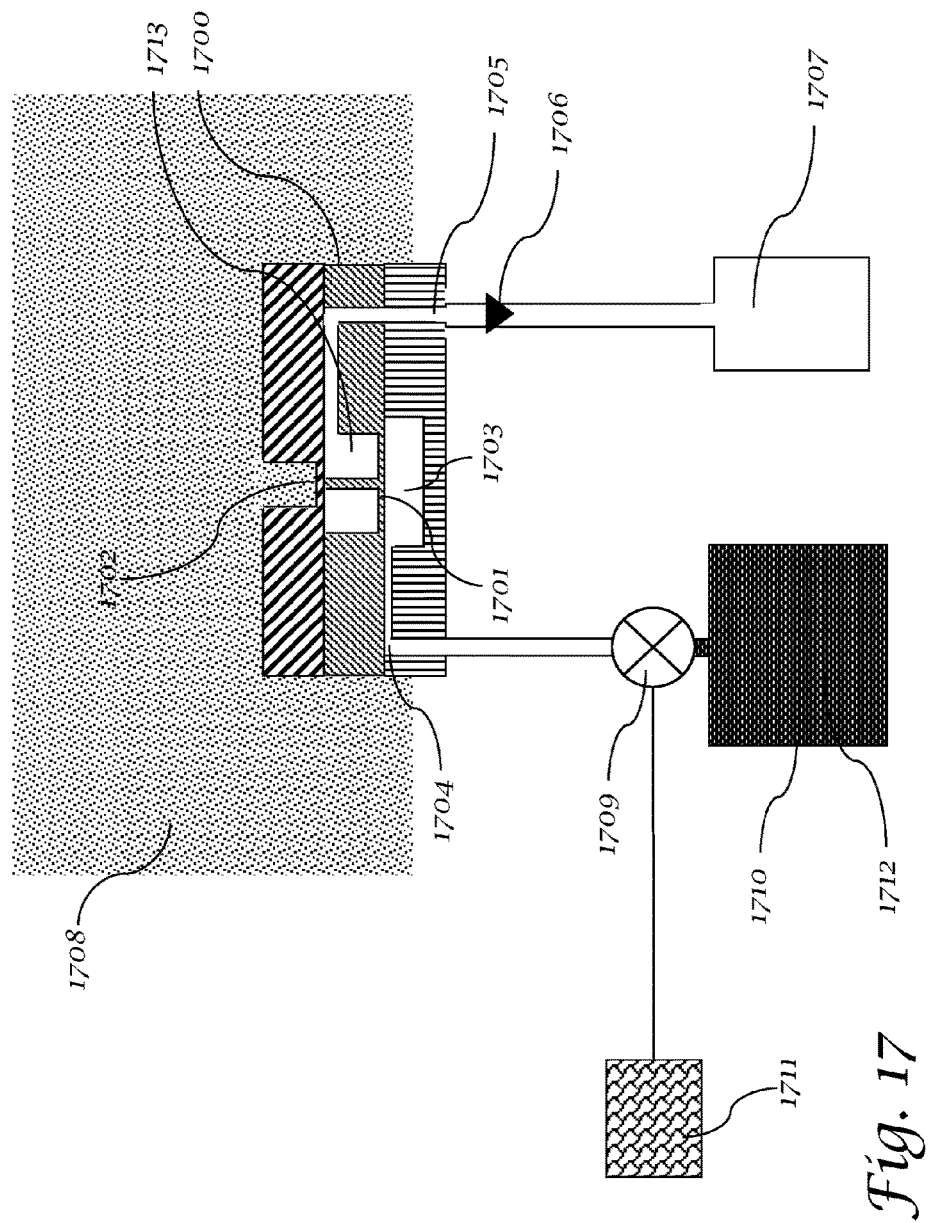
FIG. 17 shows a sampling device that includes an optional triggering system, which performs a sample acquisition within a given time interval, in accordance with an embodiment of the invention.

FIG. 17 shows a configuration of a sampling device 1700 that allows said sampling device 1700 to be in a stand-by mode for an extended period of time, and then, upon receiving an external trigger, to initiate an electrically passive timing operation and to acquire a sample from external fluid 1708 after said electrically passive timing operation is performed, in accordance with an embodiment of the invention. The device 1700 includes a timing diaphragm 1701, and a mechanical structure 1702 initially in contact with the external fluid 1708 and separating it from an isolated cavity 1713. The mechanical structure 1702 may be pierced and consequently destroyed (such as by collapsing or rupturing) by the action of the timing diaphragm 1701. The device may further include a conduit 1704, such as, without limitation, a channel, a tube, a microfluidic channel, or a pipe, and a timing cavity 1703.

The conduit 1704 is in fluidic communication with a pressurized timing fluid reservoir 1710, and may optionally include an on/off valve 1709. The valve 1709 may be actuated manually, or remotely by an optional control device 1711. An external trigger may act on the control device 1711, which in turn activates (turns on) the valve 1709. Once the valve 1709 is turned on, the timing fluid 1712 starts advancing within the conduit 1704 and, after a time interval, fills the timing cavity 1703. The pressure of the timing fluid 1704 is applied to the timing diaphragm 1701, which acts on the mechanical structure 1702 and destroys it, thus allowing a sample of the external fluid 1708 to fill the isolated cavity 1713.

The isolated cavity 1713 may optionally be connected to a sampling chamber 1707 via, without limitation, a tube 1706, channel, or pipe or any other type of fixture or device known in the art that allows fluidic communication. The tube 1706 may optionally include a check valve 1705, that allows fluid to flow into the sampling chamber 1707 but prevents it from flowing in the opposite direction.

The control device 1711 and the valve 1709 may be electrically active. The control device 1711 may be triggered remotely. The triggering action in itself may be transmitted to said control device 1711 via, without limitation, a mechanical, acoustical, electrical or electromagnetic wired or wireless link. For example, the triggering action may be transmitted to said control device 1711 via a mechanical cable or lever, a serial communication cable, a parallel communication cable, an electrical triggering cable, an electromagnetic wave using a mobile telephony network or a radio frequency or satellite connection, a pressure wave such as an acoustic or sound wave using an acoustic module (such as sonar and/or a hydrophone, a speaker and a microphone, or similar), or any other form of acoustic, electrical, electromagnetic, acoustic or mechanical communication and/or triggers known to the person skilled in the art.

This embodiment allows the sampling device 1700 to acquire a sample after a time interval following an external trigger, said time interval being measured, starting from the external trigger, using an electrically-passive timing mechanism. The sample acquisition operation, including in this case by the piercing and destruction of the said mechanical structure by the timing diaphragm 1701, is also based on purely hydraulic and mechanical action, and therefore is electrically passive.

Figure 18:
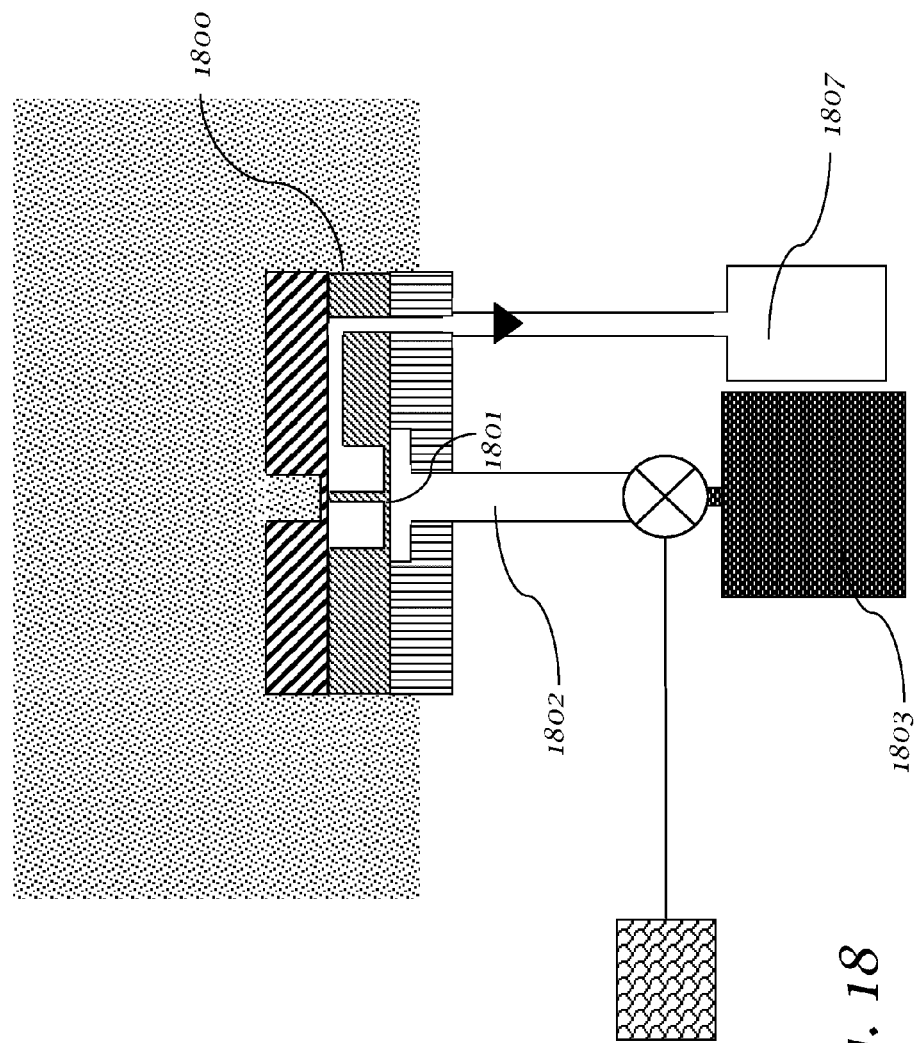
FIG. 18 shows a sampling device similar to that embodiment shown in in FIG. 17, but with the timing mechanism modified in such a way that the sample acquisition is performed in a much shorter time interval, in accordance with an embodiment of the invention.

FIG. 18 shows a sampling device 1800 that includes a sampling chamber 1807, in accordance with an embodiment of the invention, that is similar to the above-described device 1700, as shown in FIG. 17, but having a modified conduit 1802 for the timing fluid 1803, and/or a reduced timing cavity volume 1801, thus leading to a decrease of the said timing interval separating an external trigger from the sampling acquisition operation. The timing interval may be further reduced by using a timing fluid 1803 having lower viscosity than timing fluid 1712. Timing fluid 1803 may be a gas. The timing interval may thus be reduced substantially, in the range of, without limitation, 0.1 ms to 10 ms for certain applications where rapid response to an external trigger is required. In other applications, the time interval may be, illustratively, less than 100 ms, or range from 10 ms to 1 s. In other applications, the time interval may range from is to 100 s. In other time applications the required timing may be significantly longer.

Modifying Sampling Timing by Changing the Timing Cavity Volume

Figure 19:
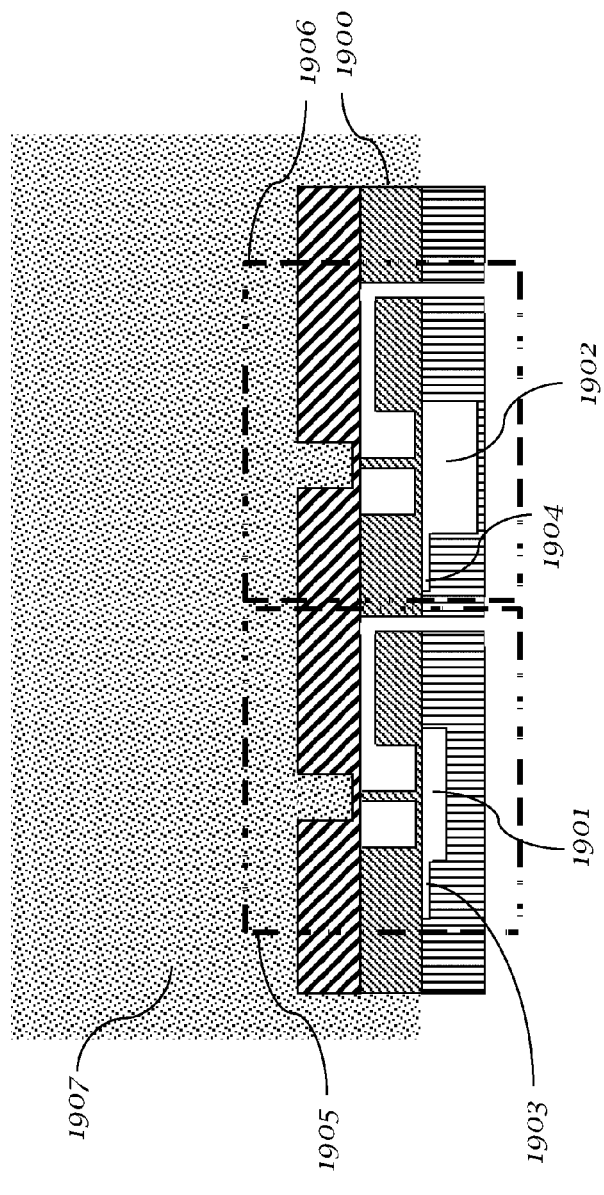
FIG. 19 shows a sampling device consisting of two sampling mechanisms whereas the timing of the two sampling mechanisms is different due to their different timing cavity volume, in accordance with an embodiment of the invention.

FIG. 19 shows another sampling device configuration, in accordance with an embodiment of the invention. The sampling device 1900, configured to acquire one or several samples from an external fluid 1907, includes at least two electrically passive sampling mechanisms 1905 and 1906. The two or more sampling mechanisms 1905 and 1906 are designed to acquire their respective samples at different times, and differ at least in the fact that the volume of the timing cavity 1902 of one of the sampling mechanisms 1906 is larger than the volume of the timing cavity 1901 of another sampling mechanism 1905. The corresponding timing fluid conduits 1904 and 1903 may be identical, or they may differ in geometry. The two or more sampling mechanisms 1905 and 1906 may be within a single sampling device as shown, or various system embodiments may include multiple sampling devices having different timing cavity volumes.

Ocean Pollution Monitoring System Deployment

In illustrative embodiment of the invention, a system is provided that may be put in place around, without limitation, an industrial facility as a precautionary measure at an early stage in the project. The systems may then be activated remotely for deployment of the sampling arrays, for example, in the event of a serious failure situation, even if control at the facility has been completely lost. The sampling arrays may be used, without limitation, to detect the scope of leaks or other pollution resulting from the failure situation. Additional fail safes may be implemented which allow for the activation of the devices in several modes on remote command from surface via an acoustic or other type of transmission. Such a system may be deployed as a fully contained unit that sits on the seafloor or other body of water in standby mode, and allows for normal operations at the facility to continue unimpeded in absence of any alert or accident.

Figure 20:
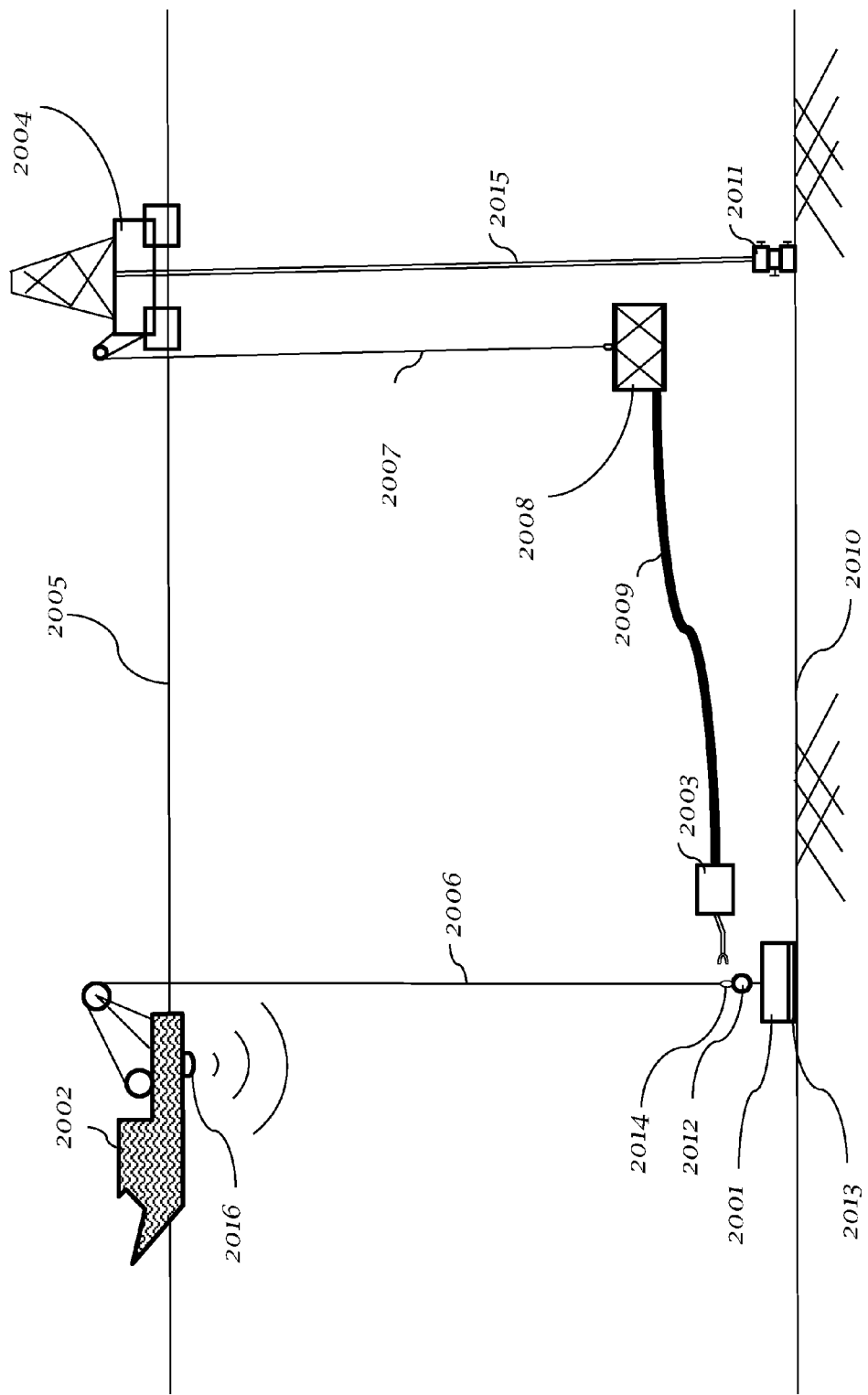
FIG. 20 shows the installation of a sampling system by a deployment vessel, in accordance with an embodiment of the invention. The installation requires accurate positioning of the system on the sea floor and may optionally be aided by an ROV for disconnection from the surface tether and/or accurate placement relative to the wellhead.

More particularly, FIG. 20 shows an installation of passive sampling systems 2001 around, without limitation, oil rigs, offshore platforms or other industrial facility 2004 that may be, for example, located in a large body of water such as the ocean, in accordance with an embodiment of the invention. The sampling systems 2001 may be located, without limitation, in a fully self contained unit, which may be installed by a surface vessel or ship 2002 that may or may not have the assistance of an ROV (Remotely Operated Vehicle) 2003. The sampling systems 2001 may be placed in an accurately known geographical location on the sea floor 2010 relative to the wellhead 2011 or as determined by GPS (Global Positioning System) coordinates, or both. The sampling system 2001 may be installed via an installation/retrieval tether 2006 by the surface vessel. This tether 2006 serves to lower the sampling system 2001 in a controlled manner from sea level 2005 to the sea floor. The self contained unit may have sufficient weight to keep the entire system negatively buoyant. In various embodiments, an anchor element 2013 may be integrated into the self contained element, or otherwise attached to the self contained unit. The sampling system 2001 may include a buoyancy device 2012 which serves as a deployment vehicle for a sampling array (described in more detail below) once activated. The system 2001 also may include a latch/release mechanism 2014, which allows for the disengagement of the installation tether 2006 either remotely by the surface vessel 2002, or physically by the ROV 2003. The latch/release mechanism 2014 may also act as a latch point for future retrieval. The installation/retrieval tether 2006 may also act as a way to keep the system 2001 suspended at neutral weight during installation such that the ROV 2003 would be able to move it in the horizontal direction, and accurately position the sampling system on the sea floor. The final position of the sampling system 2001 on the sea floor may be determined by the ROV sonar with relative position to the wellhead, and riser 2015. In addition, surface sensors located on the surface vessel 2002 such as downward facing sonar 2016, or similar technology used to locate objects below the ocean surface may be used to determine the final position of the sampling system 2001. Additionally emitters, reflectors or other devices may be positioned on the sampling system 2001 or installation tether 2006 to aid in the surface detection of the subsea position of the system 2001 during the system installation. The ROV 2003 may or may not be needed for the assistance, guidance or monitoring of the system installation, location and/or detachment of the installation tether 2006. The ROV 2003 can be deployed from either the surface facility 2004 or the surface vessel 2002 and may be deployed directly from surface or via an ROV cage tether 2007, ROV cage 2008 and ROV tether 2009.

Figure 21:
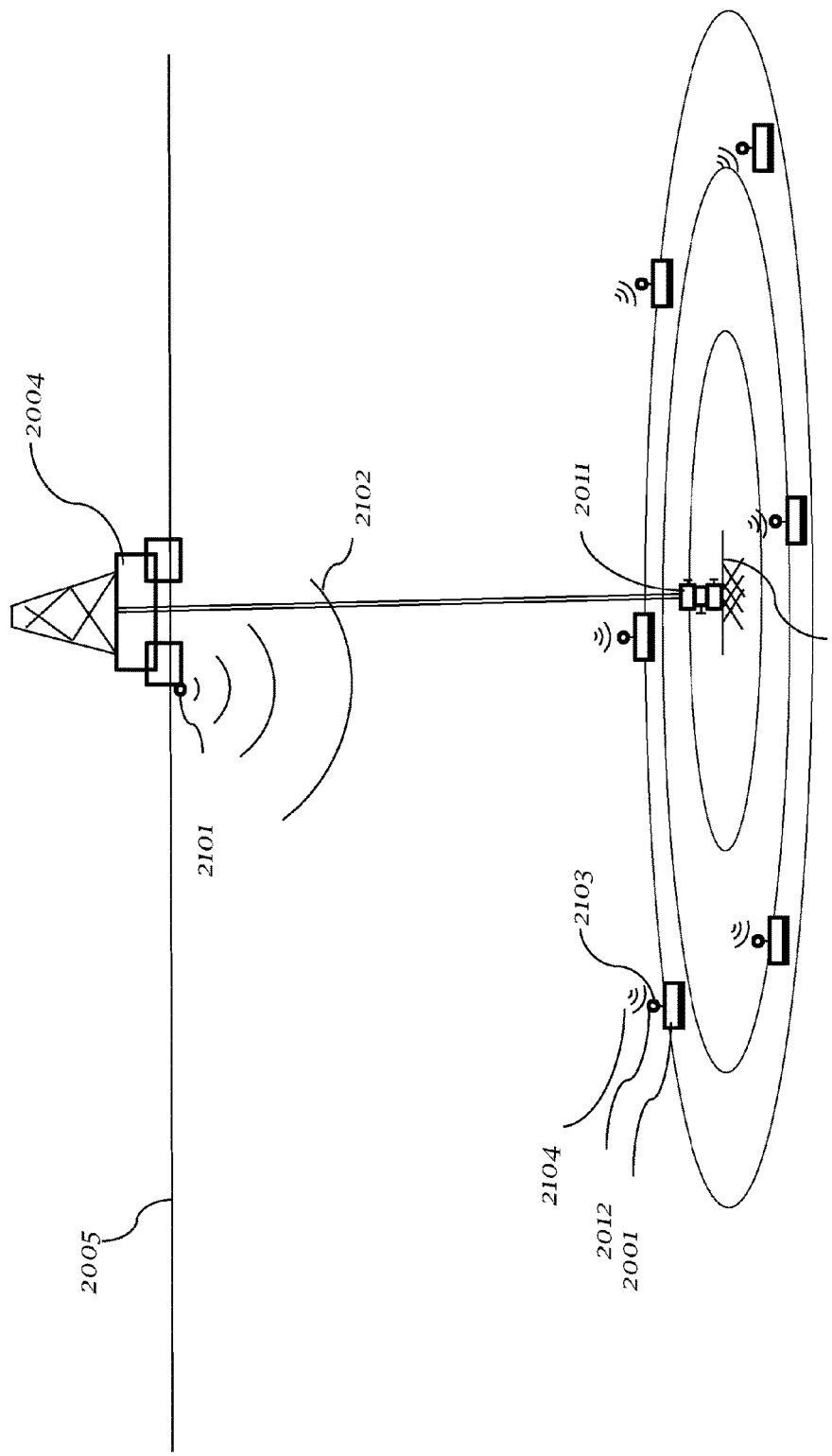
FIG. 21 shows an array of sampling systems that are installed in standby mode around an oil rig or offshore platform, in accordance with an embodiment of the invention. At the surface facility, an acoustic transmitter/receiver continuously or at pre-defined time intervals transmits an acoustic signal. This signal can be detected by the sampling systems, which indicates normal operation on surface, thus the systems will not deploy and will remain in standby mode.

FIG. 21 shows multiple sampling systems 2001 installed in an array on the sea floor around an offshore surface facility 2004, in accordance with an embodiment of the invention. The sampling systems 2001 may be arranged in any manner, layout or number without limitation. Located, without limitation, on the surface facility 2004 may be a surface transmitter/receiver 2101 which is able to transmit a control signal 2102 through the water column. The signal 2102 may be, without limitation, an acoustic or optical signal, or any other type of signal known to one of ordinary skill in the art. The transmitted acoustic signal may be projected in all directions and is not limited to only vertical or line-of-sight transmission. Each sampling system 2001 may include a subsea receiver/transmitter 2103 which has the ability to receive the signal 2104. On receipt of the signal 2104 from the surface facility 2004, the subsea receiver 2103 may either remain in standby mode, or move to sleep mode, or act as a trigger for further action within the system, depending on the signal received.

In various embodiments, each system 2001 may have the ability to transmit an acknowledgement signal, or small packet of data back to the surface facility 2004. The sampling systems 2001 may remain in standby mode as long as a transmission command is received to do so from the surface facility 2004. The system 2001 may be programmed to wake up at predefined timed intervals and listen for a control signal, such as, without limitation, an acoustic signal or an optical signal, from the surface facility 2004. If the system 2001 receives the transmission from the surface facility 2004, it is an indication of regular operation from the surface facility 2004, and the system 2001 can go into sleep mode for a specified period of time in order to conserve power. After the specified period of time, the system 2001 will again wake up and check for the transmission from the surface facility 2004. This may continue indefinitely and keep the systems 2001 in standby mode for the period of installation which may be days, weeks or many months in duration, as long as normal operations continue. In addition, an extra surface transmitter may be installed as a backup system to avoid unintended activation and deployment.

Figure 22:
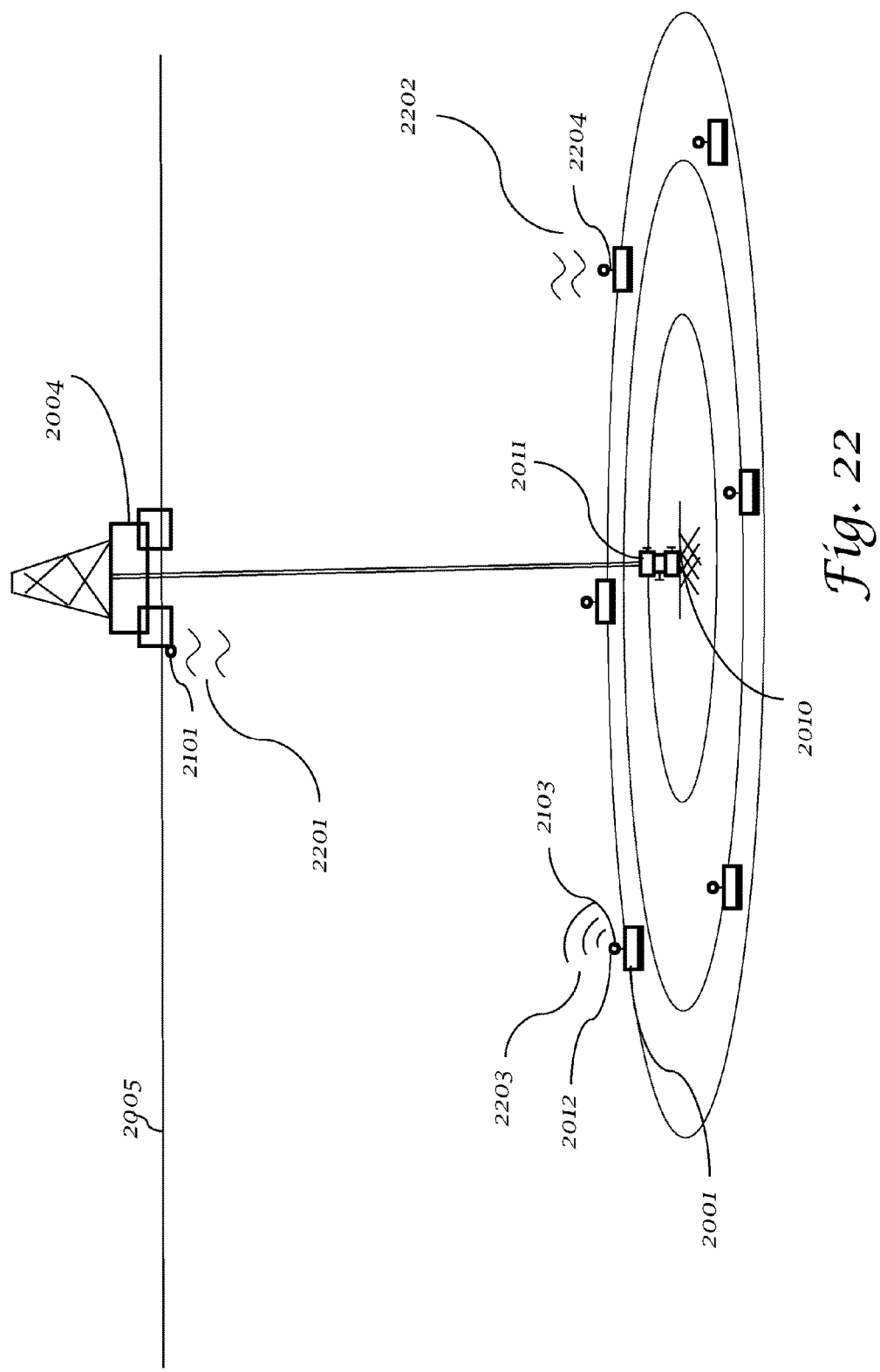
FIG. 22 shows the embodiment of FIG. 21 where there is a loss of transmitted signal from the surface facility, in accordance with an embodiment of the invention. This may be indicative of an abnormal situation at surface. The systems may continue to attempt detection of the acoustic source from surface for a period of time. If there is a continued period of loss of transmitted signal, the sampling systems will be triggered to deploy and commence monitoring.

FIG. 22 shows an event occurring at the surface facility 2004 and either power is cut to the surface transmitter 2101 (illustratively shown as an acoustic transmitter), or the transmission has been intentionally stopped by someone on the surface facility (i.e. control room personnel), in accordance with an embodiment of the invention. In this case, there is a loss of transmitted signal 2201 and thus a loss of received acoustic signal 2202 at the subsea acoustic receiver 2103. The protocol within the sampling system 2001 may change at this point, and remain awake, continuing to listen for the acoustic transmission from the surface facility 2004. At this point the subsea acoustic transmitter 2103 may emit a transmission signal or alert 2203 to the surface acoustic or optical receiver 2101 as warning to the surface facility 2004 that no surface transmission has been received. The sampling systems 2001 will remain awake in delay activation mode for a period of time which may be on the order of minutes or hours. If after this period of time, still no acoustic signal is received from the subsea acoustic transmitter 2103, a release latch mechanism 2204 may be activated by a trigger mechanism for release of the sample array (described in more detail below).

Figure 23:
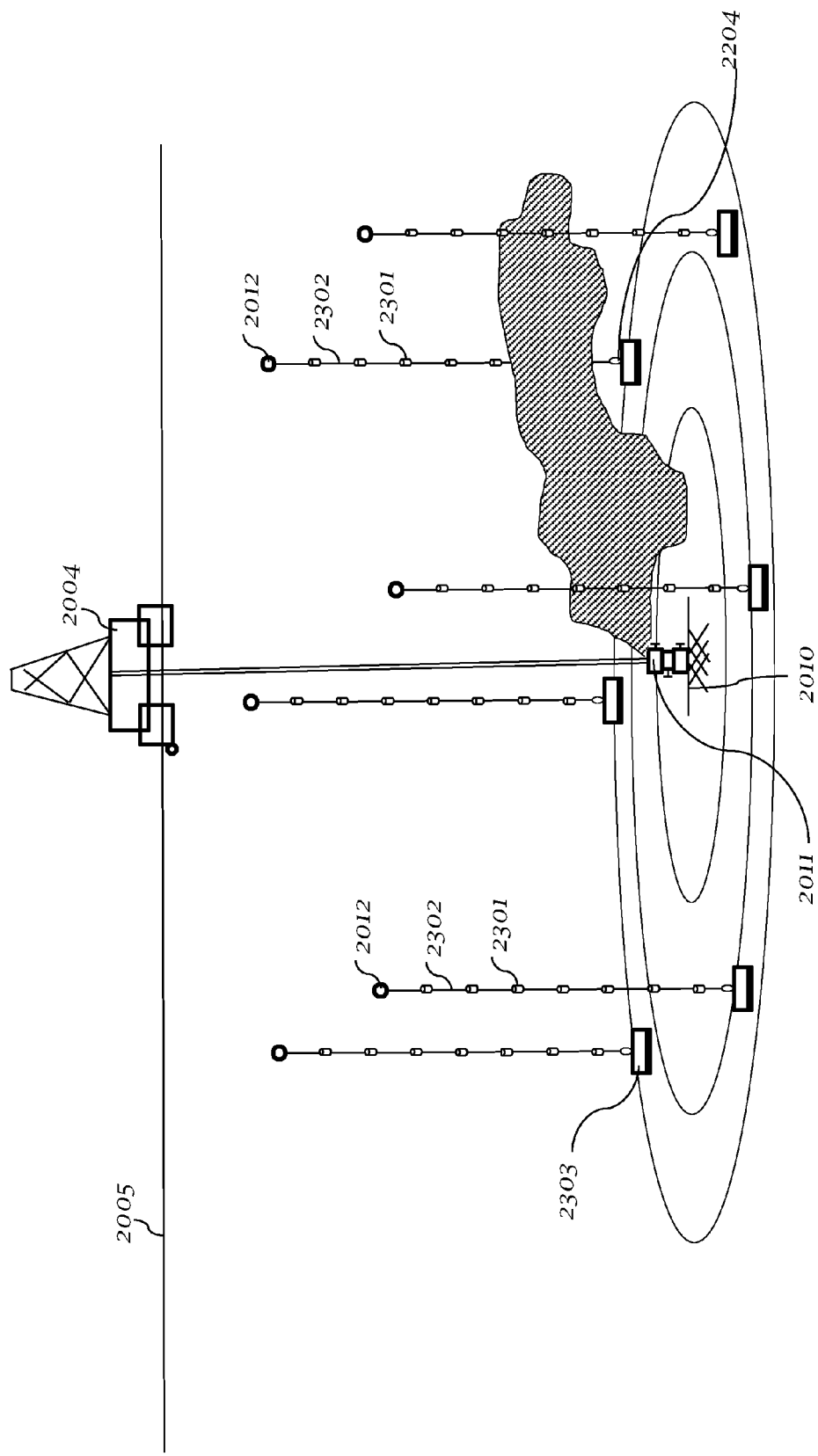
FIG. 23 shows sampling arrays after deployment due to loss of transmitted signal from the surface facility, in accordance with an embodiment of the invention. Upon deployment of the sampling arrays, each sample device may automatically start sample acquisition at predefined timing intervals.

FIG. 23 shows the result of deployment of a sampling array 2302 by release of the release latch mechanism 2204. Each sampling array 2302 may include any number of sampling devices 2301 attached to, without limitation, a rope or cable, in any spacing configuration, and may extend from sea floor to sea level, or any point in between. Upon activation of the buoyancy device 2012 to disconnect at the release latch 2204, the buoyancy device 2012 will ascend through the water column. The buoyancy device 2012 may be attached by a sampling cable to each of the sampling devices 2301 in series, such that during the ascent, each sampling device 2301 is pulled out of the containment unit 2303 and into sampling position. Alternatively, each sampling device 2301 may itself be buoyant in which case an additional buoyancy device 2012 may or may not be used. The vertical spacing of each sampling device 2301 may be determined by the length of cable that is installed between each sampling device 2301. The entire sampling string may be tethered at one end to the containment unit 2303 and anchor element 2013 to keep the entire sampling array in position. Each sampling device 2301 may be automatically triggered mechanically or electrically as it is pulled from its initial position relative to the containment unit 2303, so as to start the timing fluid for time interval sampling. This trigger may be by Hall Effect sensor, or mechanical switch, or other device with similar functionality to allow for activation of the timing fluid. In various embodiments, each sampling device 2301 may be triggered by simply deploying/entering the body of fluid (for example, the body of fluid may be used as the timing fluid). Once activated, each sampling device 2301 may acquire separate individual samples at specified timed intervals that are preprogrammed prior to installation of the sampling systems 2001.

The trigger mechanism may control the latching mechanism 2204 by providing to the latching mechanism 2204 an acoustic signal, an electric signal, an optical signal, an electromagnetic signal, or a mechanical signal, or a combination thereof. As described above, the containment unit may include a receiver for receiving a control signal that may be an acoustic signal or an optical signal, the trigger mechanism controlling the latching mechanism as a function of the control signal. The trigger mechanism may include an acoustic release, a device commonly used in fields such as oceanography. The latching mechanism 2204 may include a fusible wire and means of sending an electrical current through the fusible wire, leading to the melting of the fusible wire and the release of the sampling array. The latching mechanism 2204 may further include means to providing mechanical advantage to the strength of the fusible wire.

Figure 24:
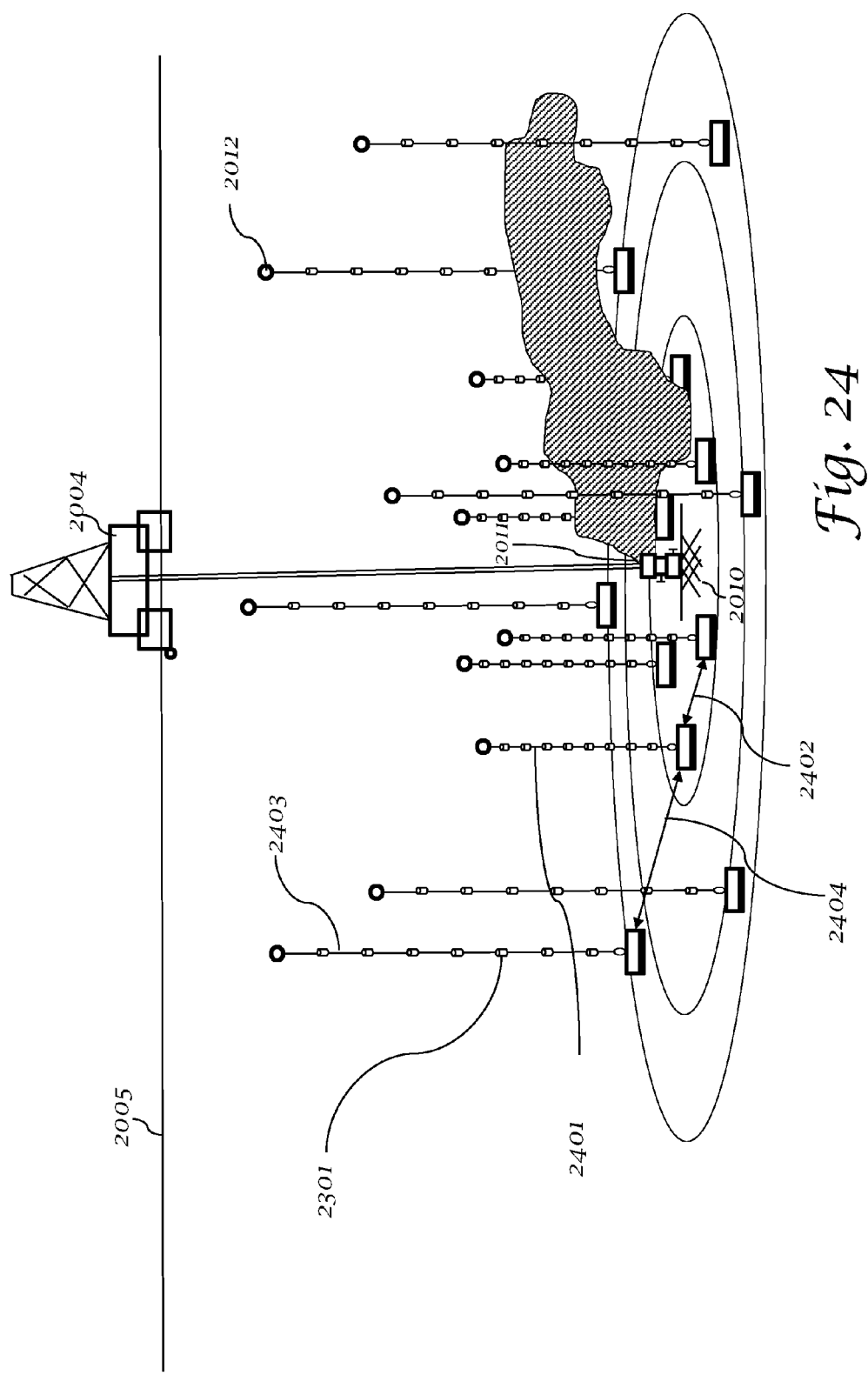
FIG. 24 shows how a specific configuration of the sampling arrays may be varied according to the location relative to the wellhead, in accordance with an embodiment of the invention. This may serve to effectively increase sampling resolution.

FIG. 24 shows deployment of monitoring systems that include near-well systems having a closer spacing both vertically 2401 as well as horizontally 2402. This provides a greater resolution of the pollution profile in 3 dimensions at the critical areas near to the wellhead 2011 over time to give a more accurate map of the pollution progression. At a greater perimeter from the wellhead 2011, the systems may have a larger spacing horizontally 2404, extend further vertically in the water column and may have a greater spacing 2403 between each individual sampling device 2301 in the sampling array. These sampling arrays may include any number of sampling devices in each array depending upon various parameters such as ocean depth or distance from the wellhead 2011 or both. The sampling arrays may also be biased or clustered in a particular direction relative to the wellhead 2011 based on known variables such as ocean current direction or ocean depth profile or shore line direction or other such factors.

Figure 25:
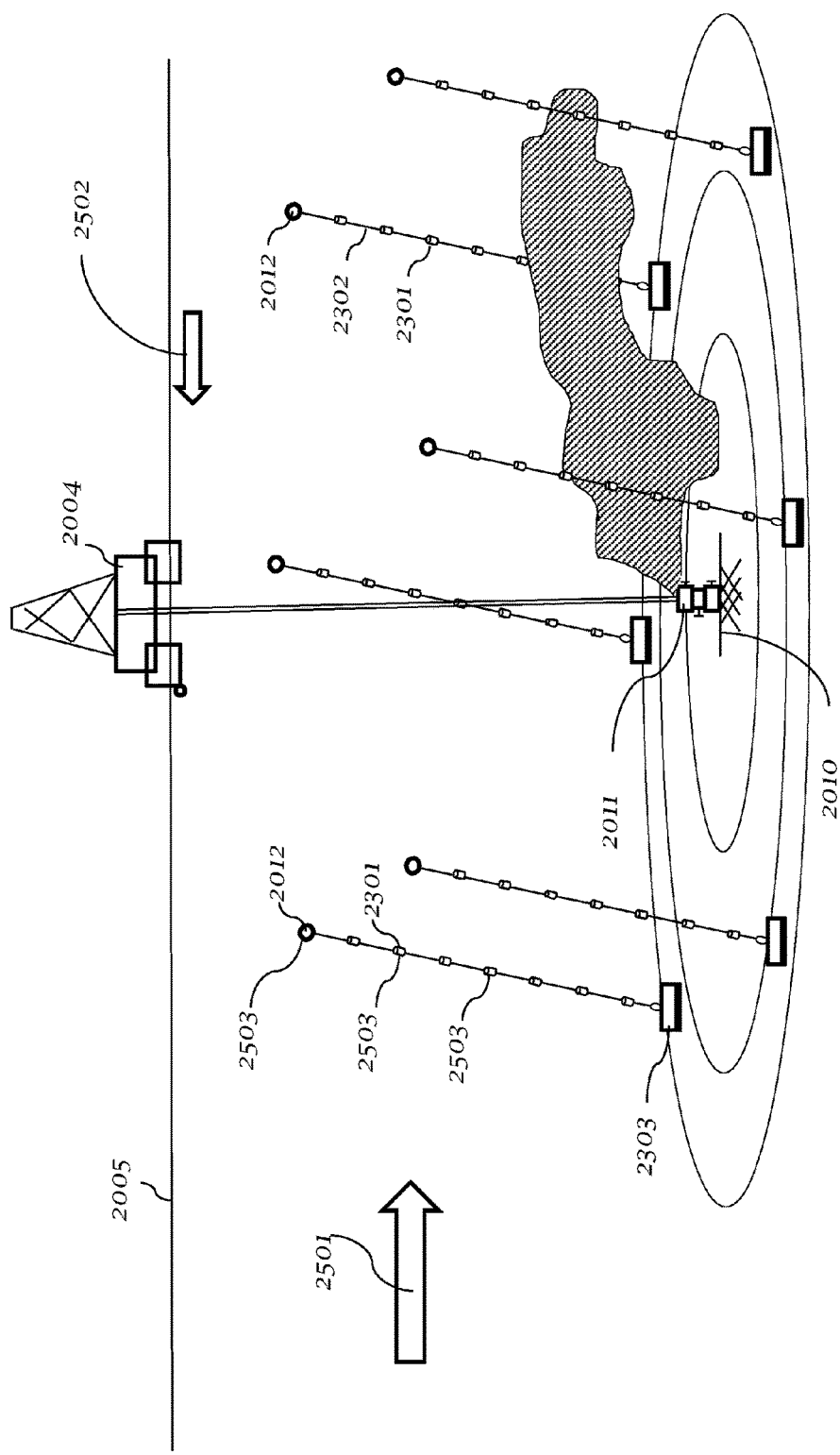
FIG. 25 shows the effect that ocean currents or other movement in the water column may have on the positioning of the sampling arrays, and how compensation using accelerometers, relative bearing meters or similar devices may be used to accurately determine the position of each point in the sampling array over time, in accordance with an embodiment of the invention.

FIG. 25 shows sampling arrays 2302 deployed in a non-static environment, in accordance with an embodiment of the invention, such as the case when there is natural ocean current 2501 or wave motion 2502 due to winds, or other movement within the ocean column. This movement may or may not be in the same direction and may cause one or more sampling arrays 2302 to be in a position that is not vertically above the original known anchoring point. In illustrative embodiments, one or multiple devices or sensors may be installed into the sampling array that are capable of measuring the array's actual position. Using such devices, the position of each sampling device in a sampling array may be accurately determined over time relative to the known anchor point.

More particularly, a device 2503 may be installed in the sampling array that includes a 3-axis accelerometer or tilt meter or inclinometer or compass or relative bearing device or flow meter or any combination of such devices or similar, such that the position of each sampling device 2301 in the string may be accurately determined over time relative to the known anchor point of the self contained unit. The device 2503 may be contained in the buoyancy device 2012 at the top of the sampling array 2302, or at a point near the top of the sampling array 2302. Additionally, any multitude of such devices 2503 may be included at multiple points along the sampling array 2302 or within the sample devices 2301. This configuration would allow for the prediction of each sampling device 2301 position in the case that forces within the ocean column are not uniform, such as variable ocean currents, resulting in a sampling array 2302 that may or may not be vertically linear. Additionally, the associated sampling devices 2301 and cable of the sampling array 2302 may be designed to be either neutrally buoyant or positively buoyant as to allow for greater confidence in the predicted position of each sampling device 2301. The device(s) 2503 would record their continuous positioning data throughout the sample acquisition in order to provide positional data of each sample device 2301 at each sample acquisition time for input into prediction models. In addition, this continuous positioning, directionality and or ocean current and flow data may be used in itself for input into prediction models beyond the point by point positional data provided only at the time of each of the acquired samples.

Figure 26:
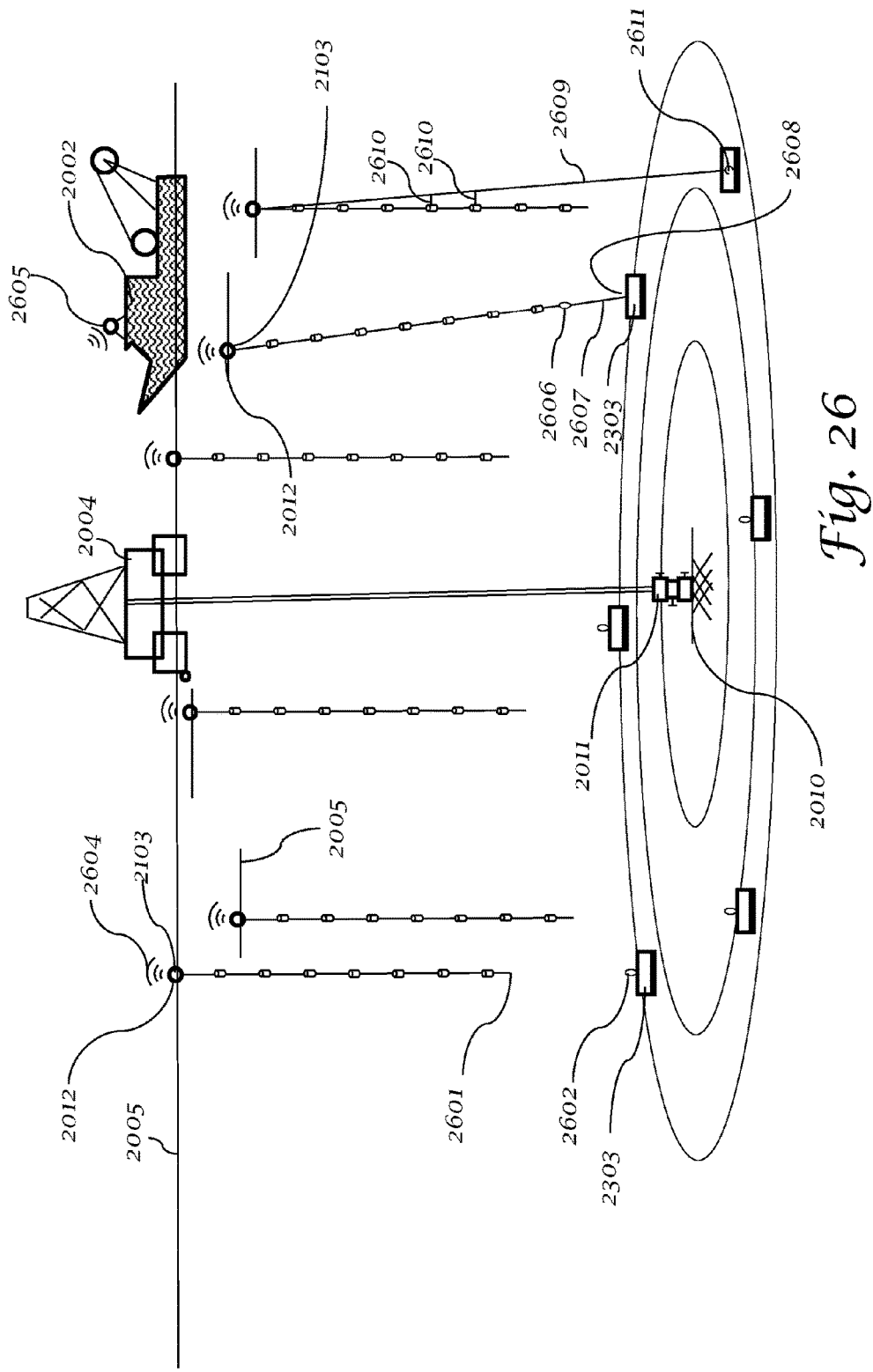
FIG. 26 shows the sampling systems after sampling has been completed and several options for retrieval of the sampling string and/or sampling system on the surface, in accordance with an embodiment of the invention.

FIG. 26 shows several options for retrieval of the sampling arrays and/or sampling systems after the samples have been acquired, in accordance with an embodiment of the invention. In various embodiments, a sample array release 2601 may be activated and separated from a latch element 2602 at the completion of all sampling. The sampling array 2302 remains attached to the buoyancy device 2012 which then ascends to sea level 2005 at the ocean surface. Latch element 2602 may also act as a connector for future retrieval of the containment unit 2303. At the same time, the retrieval transmitter 2103 located on or inside the buoyancy device 2012 may transmit a locator signal 2604, which may be in the radio frequency range for detection and location by the retrieval vessel 2002, which may carry a locator device 2605 to detect the location of these sampling arrays 2302. In addition, the buoyancy device 2012 may be a color that is highly marine visible for easy visual detection on the ocean surface. The retrieval transmitter 2103 may also contain lights that will additionally aid in the visual detection and retrieval of the sampling strings, especially during but not limited to night operations. The retrieval vessel 2002 with the locator device 2605 may determine the location of the sampling arrays 2302 by radio signal strength or by signal directionality or by visual observation or any combination of these methods. In another case, at the completion of all sampling, a sampling array release 2606 is activated which separates the sampling array 2302 from the latching element 2602 located on the containment unit 2303, however, the array 2302 is still attached to a retrieval tether 2607. This retrieval tether 2607 allows the sampling array 2302 to travel to the ocean surface, but still maintains connection to the containment unit 2303 by a connection element 2608. This connection element 2608 may be attached to a wire coil that is located within the containment unit body that is able to expel cable as the buoyance device 2012 ascends to surface. The buoyancy device 2012 may also be of a color that is highly marine visible and may contain a retrieval transmitter 2103 as described previously. The retrieval tether 2607 may be such that the length is enough to allow the buoyancy device 2012 to reach surface, or may be long enough that the tether 2607 itself can extend to surface for retrieval of the containment unit 2303 by a mechanical winch system. In this case the buoyancy device 2012 may act as a locator for the sampling array 2302, and also provide a direct connection to the containment unit 2303 for subsequent retrieval.

In yet another embodiment, the buoyancy device 2012 may include a separate retrieval tether 2609 that is attached to the containment unit 2303, but is able to spool 2611 itself out as the buoyancy device 2012 is released from the containment unit 2303 and ascends through the water column. This tether 2609 may be at a minimum, long enough to reach from sea floor 2010 to ocean surface 2005. The retrieval tether 2609 may also be such that it deploys in multiple stages. One such example would be that the retrieval tether 2609 is programmed prior to installation to release from the containment unit 2303 when commanded to do so, and unspool a certain length of cable. This would effectively set the depth of each sampling device relative to the sea floor 2010 for the duration of the timed sampling. Then after a predetermined period of time, or at a given trigger, or at the end of sampling, the retrieval tether 2609 unspools until the buoyancy device 2012 reaches the ocean surface 2005. In this case the sampling array 2302 or sampling devices 2301 may or may not be attached by an attachment line 2610 to the retrieval tether 2609, but the retrieval tether 2909 remains fixed to the containment unit 2303 on the sea floor 2010. The attachment line 2610 may be of any length, and may be used as an alternative to the cable/string of sampling array 2302 itself. Additionally, the spooling device 2611 may be placed in different points within the sampling system 2001, including mounting on or contained within the buoyancy device 2012 itself FIGS. 27(a) and 27(b) show the activation of a transmitted acoustic signal that acts as an override for sampling system retrieval, in accordance with an embodiment of the invention. The surface acoustic transmitter 2101 is capable of transmitting an override acoustic signal 2701 to the sampling systems that are in standby mode on the ocean floor. When an override acoustic signal 2702 is received at the subsea acoustic receiver 2103, the system acts to deploy a buoyancy device 2703 that pulls a retrieval tether 2709 fully to the surface. This may be performed without activation of the sampling array 2302 or sampling devices 2301. Each unactivated system may be retrieved from the sea floor for subsequent deployment at a later time, or at a different location, or both. In various embodiments, the system may contain a safety protocol, such that activation of the system cannot be triggered while the tether is physically connected to the buoyancy device or other connection point. This may be performed by Hall Effect sensor or mechanical safety lock or other method to achieve similar function. The system may be intended for repeated deployment with routine servicing and maintenance. The buoyancy device 2703 may be the same device as the previously described buoyancy device 2012, or may be a secondary buoyancy device. The buoyancy device 2703 may have an additional function whereby the override acoustic signal 2702 is able to select either to deploy the sampling array 2302, or to deploy the retrieval tether to the surface, or a combination of either, using a single buoyancy device. The buoyancy device 2012 and buoyancy device 2703 may be combined together in series and deployed independently or may be deployed simultaneously to provide an easy method for sampling and immediate retrieval after sampling. The buoyancy device 2703 may also be of a color that is highly marine visible and may contain a retrieval transmitter 2103 as described previously.

FIG. 28 shows a sampling system that is in standby mode having an additional buoyancy device 2851 which always remains at ocean surface level 2005. The buoyancy device 2851 includes a surface transmitter/receiver device 2854 that also always remains at ocean surface level 2005, and is able to transmit and receive a signal 2853, from a transmitter/receiver 2855 that is located, for example, on the surface facility 2004 and that is in the radio frequency range. This buoyancy device 2851 is connected by a cable 2850 that may or may not be electrically connected to the sampling system 2001 and the sampling deployment buoyancy device 2012. When a trigger signal 2852 is received, as described in previous embodiments, the device 2851 is able to send a deployment command signal via the cable 2850 to release the sampling deployment buoyancy device 2012. The buoyancy device 2012 and sampling array 2302 may be physically connected to the cable 2850, or may deploy independently. When deployed, the buoyancy device 2012 may extend from the ocean floor 2010 to the ocean surface 2005, or any point in between. In addition, the cable 2850 may also act as a deployment cable for a surface vessel to accurately position the sampling systems on the ocean floor. The cable 2850 may also act as a retrieval cable such that a surface vessel may retrieve sampling systems 2001 that have not yet been deployed, or also to retrieve the sampling array 2302 that has been deployed, or both.

Figure 29:
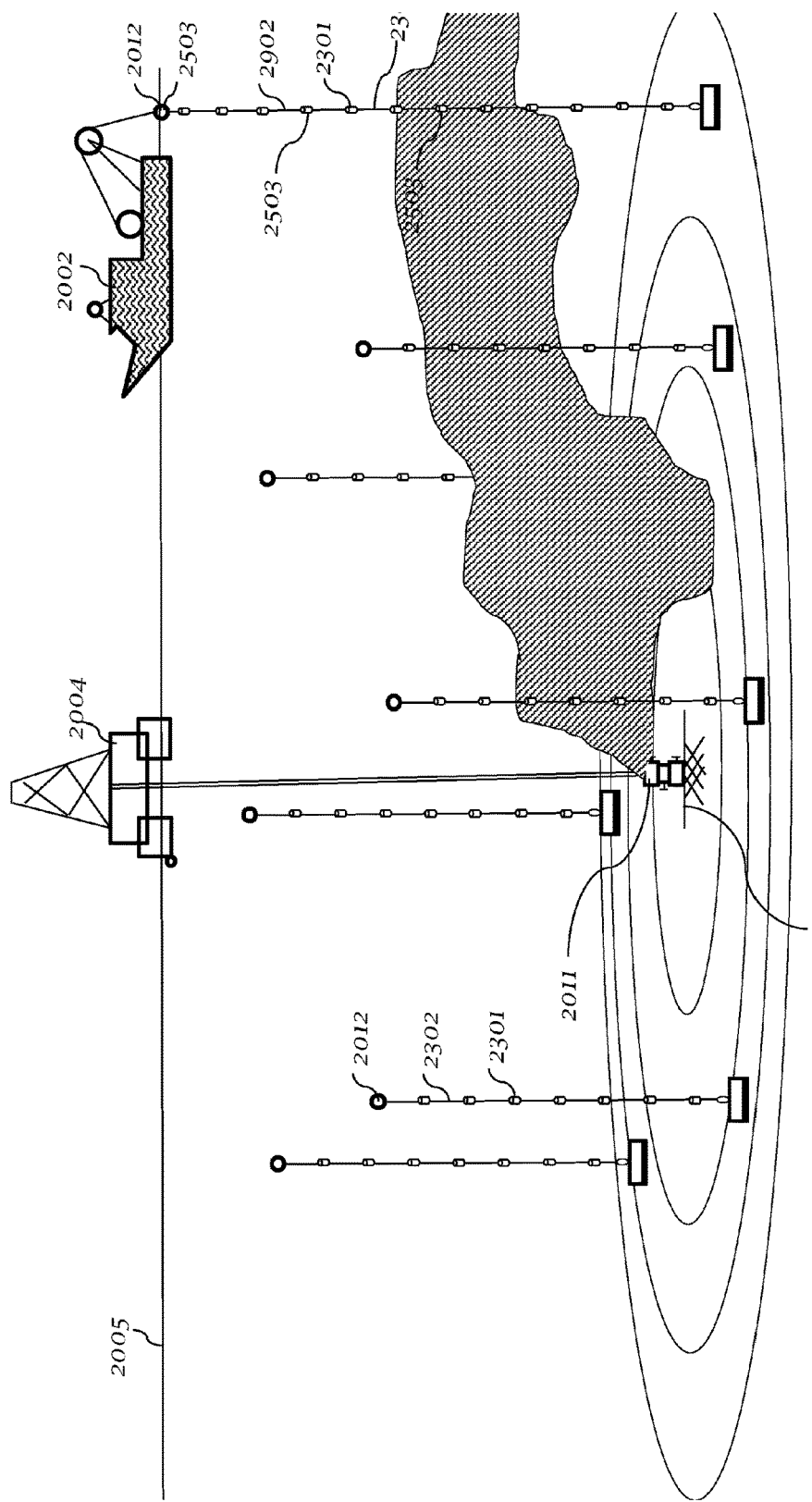
FIG. 29 shows additional sampling systems (or rapid deployment kits) which may be deployed at a greater perimeter from the wellhead after a pollution event has occurred for additional leak monitoring, in accordance with an embodiment of the invention.

FIG. 29 shows a system that may be deployed for continued monitoring of an offshore leak progression at a perimeter that may be outside of the initial deployment around the site, in accordance with an embodiment of the invention. The system utilizes deployment of "after accident deployment kits" that include one or more sampling systems 2001. These kits may be ready in standby on-shore for immediate deployment, and may be designed for larger perimeter surveys that are customizable in vertical sampling spacing 2902 for variable resolution. The deployed sampling systems 2001 may extend from ocean floor to surface, or any interval in between. Deployment and retrieval would be done directly from surface using a surface vessel 2002, with location of the sampling systems 2001 being provided by the surface vessel 2002, as described in previous embodiments. In addition, the buoyancy device 2012 may be located at the ocean surface 2005 and may include a GPS system for accurate location determination. Additionally at any point or a multitude of points within the sampling array 2302 a positioning device 2503, as described previously, may be included for accurate prediction of the position of each of the individual sampling arrays or devices over time. The "after accident deployment kits" may be immediately activated by the surface vessel 2002 as soon as they are placed in position for monitoring, or they may be installed on a time delay trigger to start the interval sampling in the future which may be minutes, hours or days.

Figure 30:
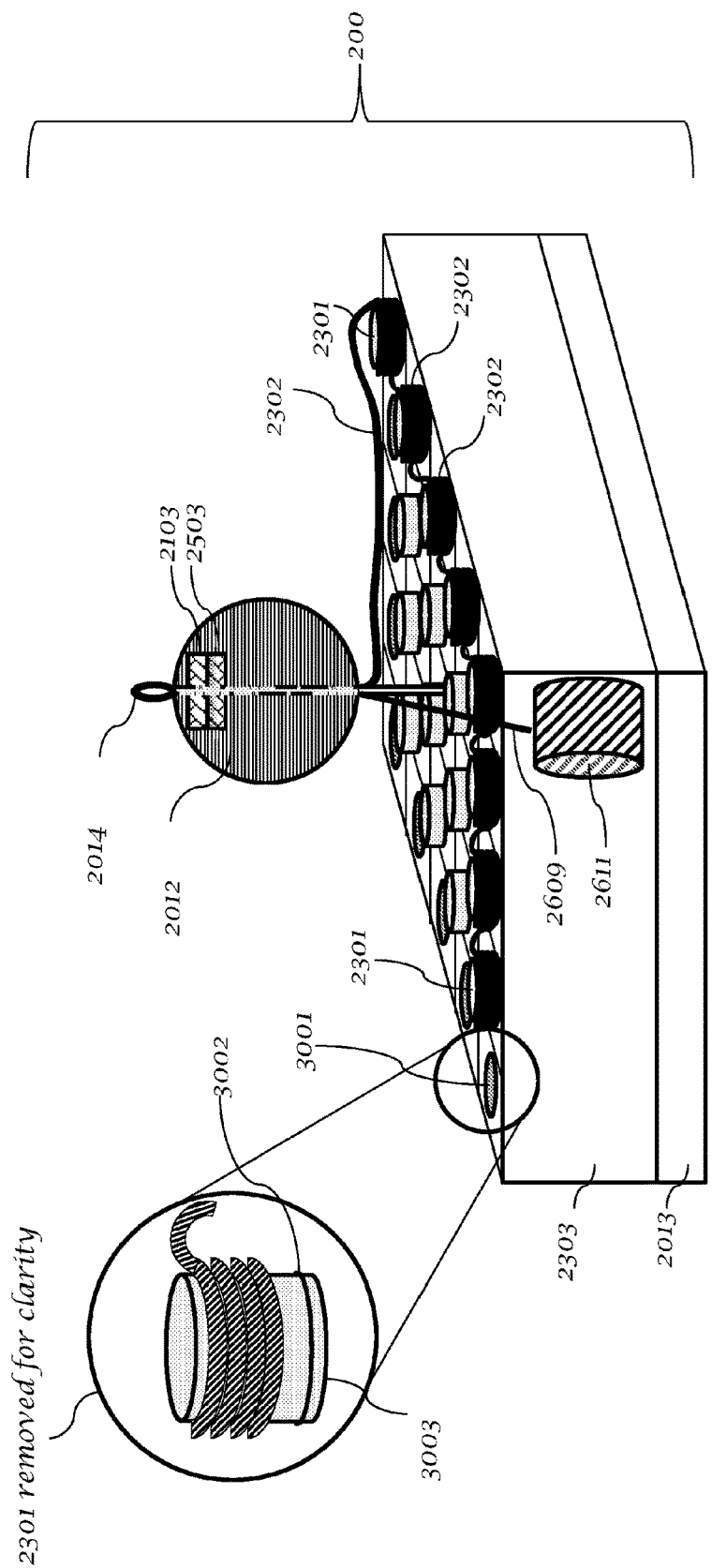
FIG. 30 shows details of a sampling system, in accordance with an embodiment of the invention.

FIG. 30 shows in detail several possible features of the sampling system 2001, in accordance with an embodiment of the invention. Reference numbers utilized have been described previously. In addition, the sampling system may include any number of sample holder ports 3001 that may be used or left empty as desired, and may vary based on parameters in the area where the system will be deployed. Each sampling device 2301 may be installed into a sample holder port 3001 and may include an O-ring seal 3002. This seal 3002 may serve to protect the sample inlet ports 3003 which may be, without limitation, located at the bottom of the sampling device 2301. The sampling device 2301 orientation may be in any direction, but a purpose of the O-ring seal 3002 is to protect the sampling inlet ports from contact with the ocean environment while in standby mode. The purpose of the protection includes avoiding any biofouling or biogrowth occurring at the sample inlet port that may impede sampling or contaminate the acquired sample. The O-ring seal 3002 may be disengaged as each sampling device is pulled out of the containment unit, allowing perfectly clean, unobstructed entry points for the sample fluid to enter the sampling device. The O-ring seal 3002 may provide a full pressure seal to hydrostatic pressure, or may be prefilled with fresh water, or any known fluid that rejects biofouling or biogrowth. This fluid may or may not also be used for hydraulic compensation at the O-ring seal. The system may be configured such that the sample holder ports 3001 automatically fill with seawater at the release of the buoyancy device 2012, such as by opening a fluid inlet at the release of the buoyancy device.

According to related embodiments of the invention, a sampling system may include location devices such as global positioning systems (GPS units). Said sampling system may be equipped with emitters capable to send the GPS coordinates either via a satellite data link, or via the phone network system or by other means of radio communication. Once it has been released from the ocean floor and has reached the ocean surface, a sampling system may emit radio waves, electromagnetic, acoustic or optical beacon signals, so as to alert ships or other ocean vehicles of its presence and to send current position to a data collection system. The GPS units and communication emitters may be built into, or attached to each sampling unit on the sampling system, and/or to a buoyancy device.

Monitoring System (Time Stamping and Sample Acquisition Monitoring)

Figure 31:
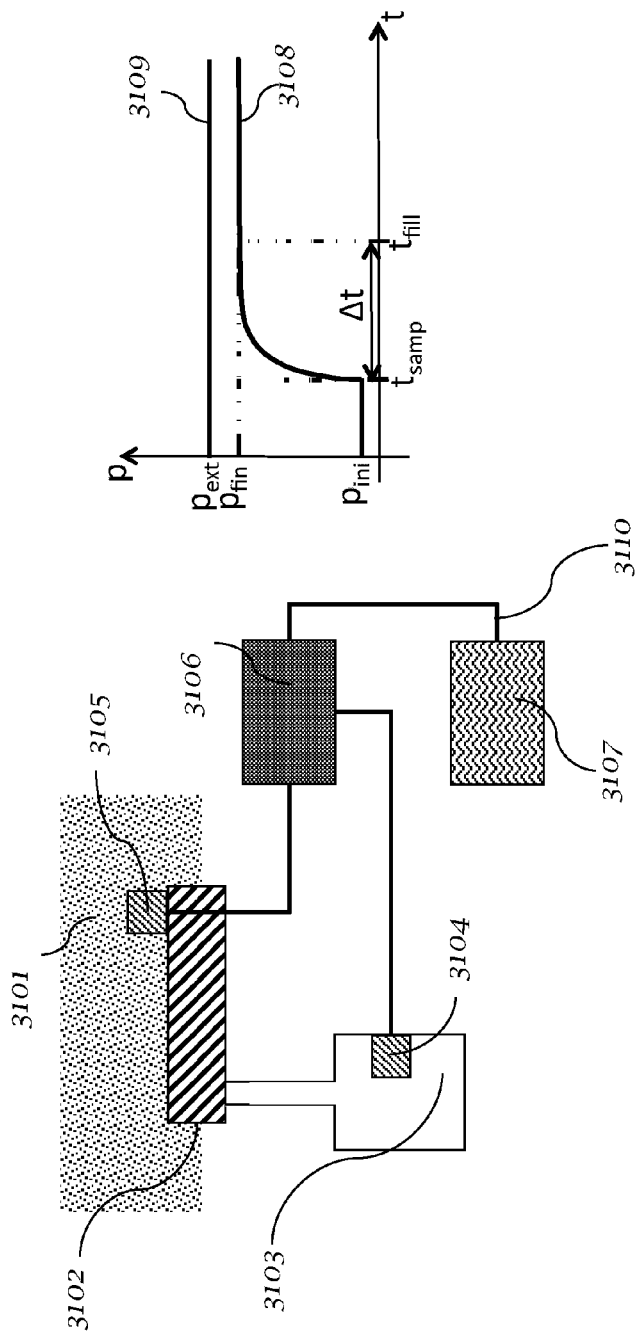
FIG. 31 shows a timestamping and sample acquisition monitoring system that allows the determination of the timestamp of each sample acquisition and of different other parameters related to the sample acquisition process based on measurements of pressure levels within the sample chamber and, optionally, in the external fluid, in accordance with an embodiment of the invention.

FIG. 31 shows a monitoring system for recording sample acquisition time of each sample. More particularly, sample device 3102 includes a pressure active device 3104, in accordance with an embodiment of the invention. The sample device may be, without limitation, as described in above embodiments, configured to acquire a sample from an external fluid 3101. The sampling device 3102 includes a sample chamber 3103 for collecting the sample. Said sample chamber 3103 may incorporate in its interior a pressure-active device 3104 that responds to pressure within the sample chamber 3103. The pressure-active device 3104 may be in communication with a processor 3106 for analyzing and/or recording the signal from said pressure-active device 3104. The processor 3106 may include an amount of electronic memory in the form of random access memory, flash memory, permanent memory, electrically erasable programmable memory or any other form of electronic memory known in the art. The pressure-active device 3104 may be a pressure sensor, a pressure switch, a pressure gauge, a pressure transducer, or any other device known in the art that can transform a pressure variation into a signal.

The processor 3106 may be in communication with a second pressure-active device 3105 that is placed in and responds to the pressure of the external fluid 3101. The processor 3106 may further be in communication with a remote system 3107, to which it may transmit data via a wired or wireless link 3110.

If the pressure-active device 3104 is a pressure sensor, the processor 3106 may record a pressure curve 3108 of the pressure inside the sampling chamber 3103, and by analyzing the data from said pressure curve it may calculate the exact moment timestamp ($t_{samp}$) of the sample acquisition initiation. The timestamp of the sample acquisition $t_{samp}$ can be inferred, for example, by monitoring the sample chamber pressure sensor for a significant deviation from the initial pressure in the sample chamber ($p_{ini}$).

In various embodiments, the processor 3106 may process the pressure data originating from pressure sensor 3104 so as to determine a sample fill-up duration $\Delta t$ by recording the time ($t_{fill}$) when pressure stabilizes within the sample chamber 3103, and subtracting from this value the time corresponding to beginning of the sample acquisition tsamp: $\Delta t = t_{fill} - t_{samp}$ In various embodiments, the processor 3106 may process the pressure data originating from pressure sensor 3104 to determine the total volume ($V_{samp}$) of the sample acquired. This volume can be inferred by knowing the volume $V_0$ of the sample chamber 3103 and the value $p_{ini}$, of the initial pressure in the sample chamber 3103 prior to sample acquisition, the value $p_{fin}$ at which pressure has stabilized in the sample chamber after the sample acquisition, and the pressure $p_{ext}$ measured by the pressure sensor 3105 monitoring the pressure of the external medium 3109.

The processor 3106 may determine $V_{samp}$ by using the following formula, which assumes the sample acquisition process as being isothermal and the gas initially contained in the sample chamber to be an ideal gas, in which case $V_{samp} = V_0(1 - p_{ini}/p_{fin})$.

A difference between $p_{fin}$ and $p_{ext}$ may be interpreted by processor 3106 as evidence of clogging during the sample acquisition process.

If the pressure-active device 3104 is a pressure switch, the moment of the activation of the pressure switch as recorded by the processor 3106 corresponds to the timestamp of the sample, $t_{samp}$.

Integration of Optical Elements Within or Around the Sample Chamber

According to an embodiment of the present invention, a sample chamber of one of the above-described sampling devices may include optical elements for performing a measurement of, without limitation, turbidity, absorbance, color, transmittance, autofluorescence, or fluorescence, or any combination thereof.

The sample chamber may incorporate certain optical components, either inside the sample container or in its proximity, in order to assure that the light travels across or around, or otherwise interacts with the sample in an optimal way.

Said sample chamber may be equipped, without limitation, with: one or several optical windows allowing an optical measurement to be performed on the sample contained within the sample chamber, one or multiple light sources, optical detectors, sensors or recording devices (with no limitation: cameras, individual photodiodes or arrays thereof, other types of optical sensors, phototransistors, avalanche photodiodes, photomultipliers), mechanical positioning assemblies, fibers, diaphragms, mirrors, optically absorbing surfaces, optical filters or any other type of optical component or device known to the person skilled in the art, or any combination or configuration thereof.

Data obtained from the optical elements equipping the sample chamber may be used to measure the exact time of the sample acquisition (its timestamp). As an example, a processor could monitor a change in the optical properties of the sample chamber. Said processor may process data from an absorbance measurement performed on the acquired sample at a wavelength where the sample fluid absorbs light (such that the measured absorbance will be higher after sample acquisition than prior to it). Alternatively, said processor may use the presence of an optical signal (or the lack thereof) to infer a deviation of the light path due to a change in optical refraction index that is indicative of a sample being present within the sample chamber.

Any other type of measurement, optical or not, that is known to the person skilled in the art, may be used to determine whether a sample has been acquired within the sample chamber. This may include a conductivity measurement, a temperature measurement, an electrochemical measurement, an optical measurement, a physical measurement, a force measurement, a deflection measurement, a chemical measurement, a biological or biochemical measurement, or any combination thereof.

Passive Timing Mechanism of Improved Precision

As described above in the background section, assume one sample needs to be acquired every hour for a period of twenty four hours. Twenty four sampling devices are deployed at t=0, device numbered n (1<n<24) having a time constant of n hours prior to triggering the acquisition of its corresponding sample. If there is a ten percent error in the fluidic clock of each sampling device, that means that it is likely that the order of the sampling events will be disturbed. For example, the 10th device may acquire its sample at t=11 h, and the 11th device at t=10 h, thus they will be out of order.

A system is provided that advantageously includes a number n of sampling devices that are being timed by fluidic clocks in such a manner that the timing mechanism of the n+1st device is triggered by the acquisition of the nth sample, in accordance with an embodiment of the invention. Illustratively, in the above-described application, each device could have a time constant of 1 hr (or 60 minutes). A ten percent random error in the timing means that the time interval between one sample n and the subsequent one n+1 will carry an absolute error of 6 minutes, but all the samples will be acquired in sequence.

Figure 32:
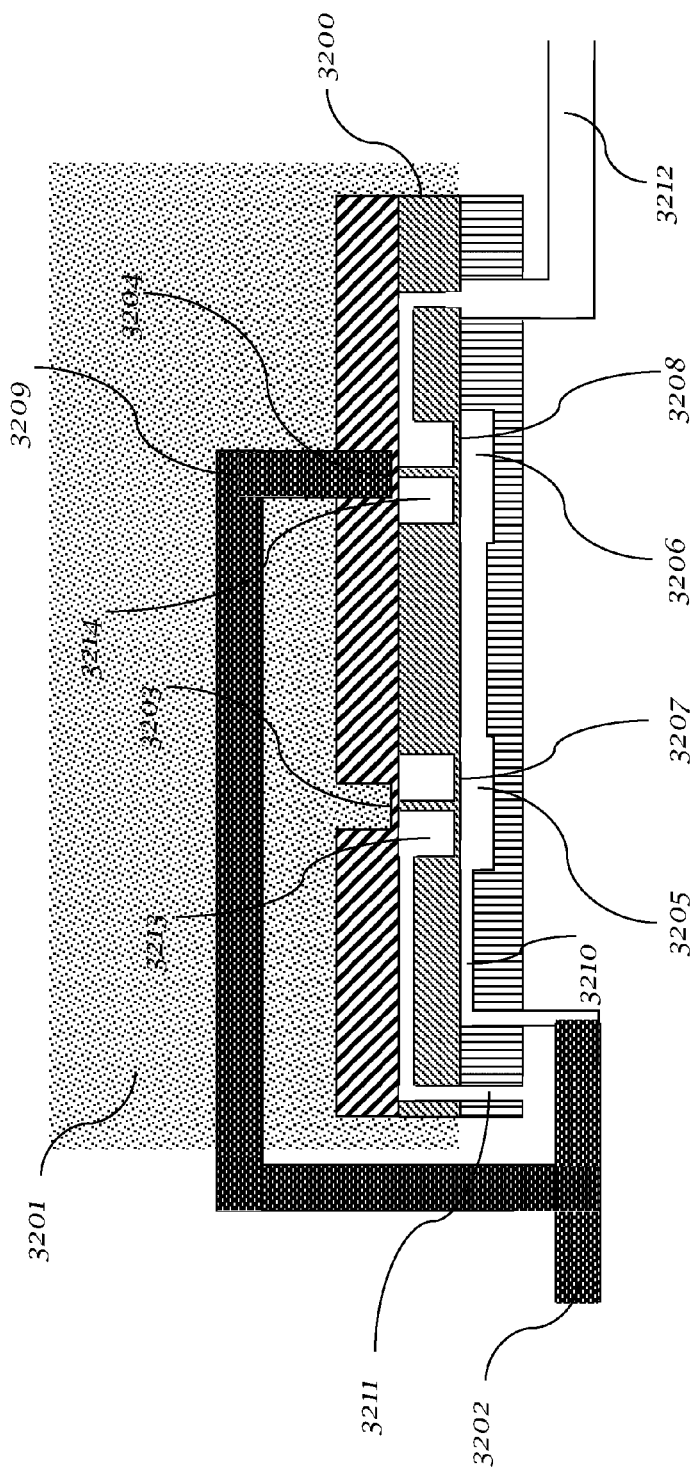
FIG. 32 shows a sampling device implementing a passive timing mechanism allowing the timing of a sample acquisition to be triggered by the acquisition of the previous sample, in accordance with an embodiment of the invention.
Figure 33:
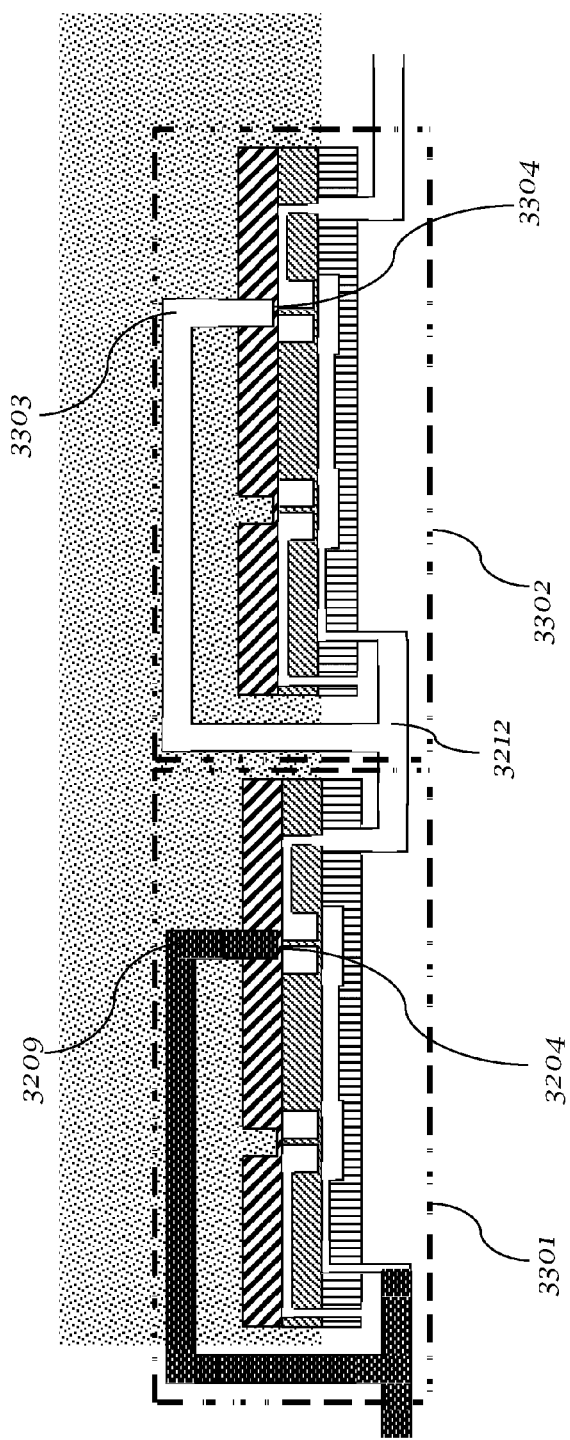
FIG. 33 shows sampling devices described in the embodiment of FIG. 32 connected together so as to trigger each other, in accordance with an embodiment of the invention.
Figure 34:
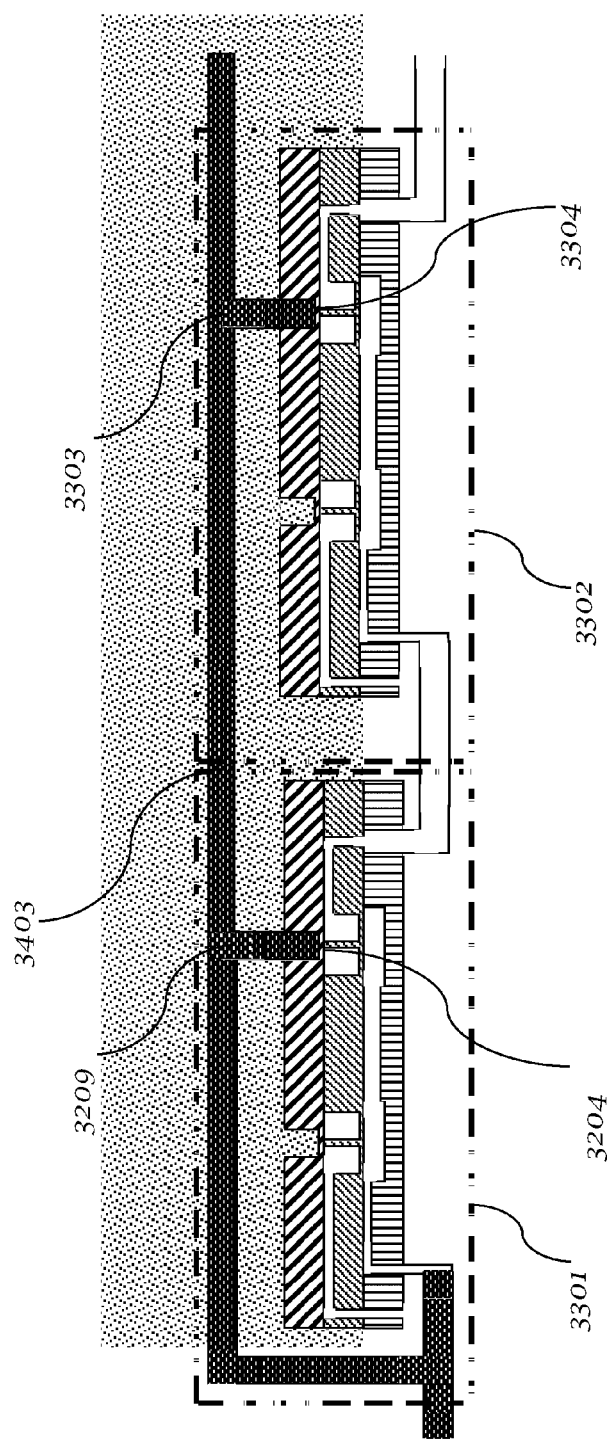
FIG. 34 shows sampling devices described in the embodiment of FIG. 32 connected together so as to trigger each other, further shows a manifold, in accordance with an embodiment of the invention.

More particularly, FIGS. 32-34 show embodiments of the invention that result in passive timing mechanisms of improved precision. A sampling device is provided that includes multiple sampling mechanisms capable of timing and performing the acquisition of multiple (n) samples in an electrically-passive way, where the electrically-passive timing mechanism corresponding to sample i+1 is triggered at a time instant that is related to the time of acquisition of sample i. The sampling device acquires samples from an external fluid.

As shown in FIG. 32, an exemplary sampling device 3200 may include two timing diaphragms 3207 and 3208, two connected timing cavities 3205 and 3206, two mechanical structures 3203 and 3204 and two isolated cavities 3213 and 3214. The first mechanical structure 3203 separates the external fluid 3201 from the first isolated cavity 3213.

The sampling device 3200 further includes a conduit 3210 that may be a microfluidic channel or a capillary tube, and that may have a predefined geometry. Upon applying pressure to a timing fluid 3202 within the conduit, said timing fluid 3202 being a liquid or a gas, said timing fluid 3202 advances within the conduit 3210 at a speed, for example, that may be dictated by the applied pressure, the predefined channel geometry and known timing fluid properties. The timing fluid conduit 3210 is also connected, by a tube or similar fluidic connection 3209, to the second mechanical structure 3204. Upon reaching the connected timing cavities 3205 and 3206 and filling them after a timing interval, the timing fluid 3202 applies pressure to the two timing diaphragms 3207 and 3208 simultaneously, thus destroying their corresponding mechanical structures 3203 and 3204, for example, by piercing and consequently rupturing and/or collapsing them.

The first mechanical structure 3203, once destroyed, allows a sample of the external fluid 3201 to be acquired by enabling the external fluid to enter the isolated cavity 3213, which may then further lead to a sampling chamber via a channel, tube pipe or any other type of fluidic connection 3211. The second mechanical structure 3204, once destroyed, opens a passage for the timing fluid 3202 to enter the timing fluid conduit 3212 of a subsequent sampling mechanism, thus acting as an effective trigger for timing the acquisition of the next sample.

FIG. 33 shows two sampling devices 3301 and 3302, each as described by FIG. 32, such that the timing fluid conduit 3212 of sampling device 3303 is connected to the second mechanical structure 3204 of sampling device 3301. The tubes 3303 and 3209 that allow the fluidic communication between the timing fluid and the second mechanical structures 3204 and 3304 of sampling devices 3301 and 3302 may be distinct.

In the configuration shown in FIG. 33, the acquisition of a sample by device 3301 happens simultaneously with the destruction of the mechanical structure 3204, which allows the timing fluid to enter device 3302 and, following another timing interval, the device 3302 will acquire its own sample. Any number of such sampling devices may be connected in sequence, each sampling device acquiring its sample after being triggered by the previous sampling device.

FIG. 34 shows a related embodiment of FIG. 33, showing the same two sampling devices 3301 and 3302, and further showing the tubes 3303 and 3209 allowing the communication of the timing fluid with the second mechanical structures 3204 and 3304 of the sampling devices 3301 and 3302. It is further shown that the tubes 3303 and 3209 may be connected using a common manifold 3403 or a similar fluidic connection.

It is understood that such operation can be implemented using other embodiments of the sampling mechanism. For example, using pistons instead of timing diaphragms, as described previously, to pierce the mechanical structures.

Microbiological Measurement

It may be advantageous to allow a sample to incubate for a certain period of time, so as to allow a certain type of microorganism to multiply and grow. According to further embodiments of the present invention, a sampling system may be equipped with a sample chamber that is partially pre-filled with a culture medium. Said culture medium may be selective, allowing only select classes of microorganisms to develop and grow. Said sample chamber may be configured so that, upon sample acquisition, the sample comes in contact with the culture medium. The culture medium is selected such that, if the sample is contaminated with a select class of microorganisms, these will multiply, over a period of time called the incubation period. For example, and without any limitation, certain commercial culture media and bioreagents exist (such as, without limitation, the bio-reagents commercialized under the brand names Ready-Cult and Colilert), that allow coliform bacteria to incubate, and over a period of incubation time of several hours the samples change color or fluorescence properties which can lead to the detection and quantification of the said coliform bacteria or of certain classes thereof.

Said sample chamber may include a temperature control mechanism that ensures that the sample temperature is maintained within a range that is optimal for sample incubation.

Said sample chamber may include chemical and/or biological reagents, and/or biocides that react in the presence and/or of the quantity of said microorganisms. Detection of said reaction result may be performed optically, for example (without implying any limitation) by performing an optical absorption measurement, a color measurement, or by monitoring its fluorescence, or its auto-fluorescence.

This embodiment may be combined with other embodiments of the present invention.

Built-In Redundancy

Due to the impracticality of on-line operation monitoring for passive devices such as the above-described devices and systems, it may be advantageous to incorporate various redundancy schemes, to minimize the chance of failure due to unforeseen circumstances. Redundant timing and sensing mechanisms, rendered possible by the extreme miniaturization may be integrated within the device. All critical device components may be built in multiple copies on a single chip, providing parallel fluid and measurement paths in case of failure (e.g., due to channel clogging or sensor malfunction). Single chips may be designed to include multiple sensor chambers for sample analysis, as well as multiple acoustic-emission isolation diaphragms and associated cavities, thus providing multiple assays and hence improved measurement statistics once the devices are recovered at the surface. Multiple timing mechanisms having different time constants may be incorporated onto a single device as well, thus providing a measurement time-series to monitor the evolution of a parameter of interest over a device well injection and retrieval cycle. The resulting device architecture can be extremely robust and should be capable of providing a reliable measurement even in the most adverse environmental conditions.

Harsh Environment Compatibility

Completely passive systems represent an advantageous approach to sensing in the very harsh environments specific to the oilfield (e.g., high temperature and pressure (HPHT), corrosive fluids, severely constrained geometry). The above-described embodiments allow the deployment of smart passive devices that are capable of performing a number of specific, well-defined functions in, without limitation, the subterranean environment surrounding an oil well, without requiring power, monitoring, or telemetry. Such smart passive devices can be deployed downhole by pumping along with frac- or other injected fluids, or they can be integrated within existing oilfield measurement tools such as the MDT tool, the FMT tool or the SFT tool. The smart devices may acquire, react with, and isolate a sample of downhole fluid, and, once retrieved from the reservoir, they can be interrogated by optical, electrical or other means to provide information about the environment they have been exposed to (e.g. chemical or physical properties of the fluids encountered) as well as about the times when the measurements were performed. Additionally, as described above, the device can emit bursts of acoustic signals at pre-defined times which can allow device localization by, without limitation, triangulation using multiple microphones.

All the device functionalities recited above may be implemented in multiple applications, and are not limited in any way to oilfield measurements. Examples of different applications include, but are in no way limited to: submarine deployment of such systems as in a body of water, river, lake, sea, ocean; measurements within water wells and aquifers; waste water storage tanks and reservoirs, and the monitoring thereof; and injection wells for carbone dioxide sequestration.

The above-described embodiments are not constrained to a specific sensing technology—several technologies are compatible with and can be integrated within such a smart passive device, such as, without limitation: purely chemical sensors (e.g. titration reactions), corrosion sensors, MEMS sensors, electrochemical sensors, and functionalized nanoparticles. The purely passive devices may be mission-specific so as to integrate only those functions that are absolutely paramount to performing and later interpreting the specific measurement (or chemical reaction) of interest; all additional functionality will be provided externally after recovery. This purely passive approach therefore minimizes the risk of system failure due to environmental issues.

Ultimate Size Miniaturization

Besides the capability to survive a harsh environment, a fully passive system provides ultimate miniaturization capabilities. Typically, physical transducers occupy only a very small percentage of the total package size in miniaturized sensors (such as those using MEMS technology), the rest being occupied by electronics and connections. A passive approach eliminates the need to operate electronics downhole, and thus can lead to impressive size reduction. The use of small, passive devices, that may be fabricated using, without limitation, MEMS technology, permits deployment within pores and/or fractures of the rock. Such deployment may be performed, for example, as part of a proppant formulation during hydraulic fracturing operations.

Manufacturing Techniques

The above-described devices may be employed in harsh environments and require resistance to high external mechanical stresses. Furthermore, in various implementations, a large-volume manufacturing technology that allows cost-effective miniaturization of the complex device geometries is often desirable. Pure microelectromechanical (MEMS) technology, allowing extreme miniaturization with ultimate dimensional control, may be an excellent choice for laboratory scale experiments and field testing, but may be less ideal for real, large-scale field deployment: it is expensive; MEMS materials are extremely brittle leading to limited device survivability; and the fabrication technology, based on planar lithographic mask-based processes, often imposes important device geometry constraints. Fabrication using a hybrid MEMS-AMM (additive micro-manufacturing) approach may preserve the advantages but overcome the limitations of pure MEMS technology, allowing the industrialization and large-scale production of the devices at a competitive cost.

Figure 35:
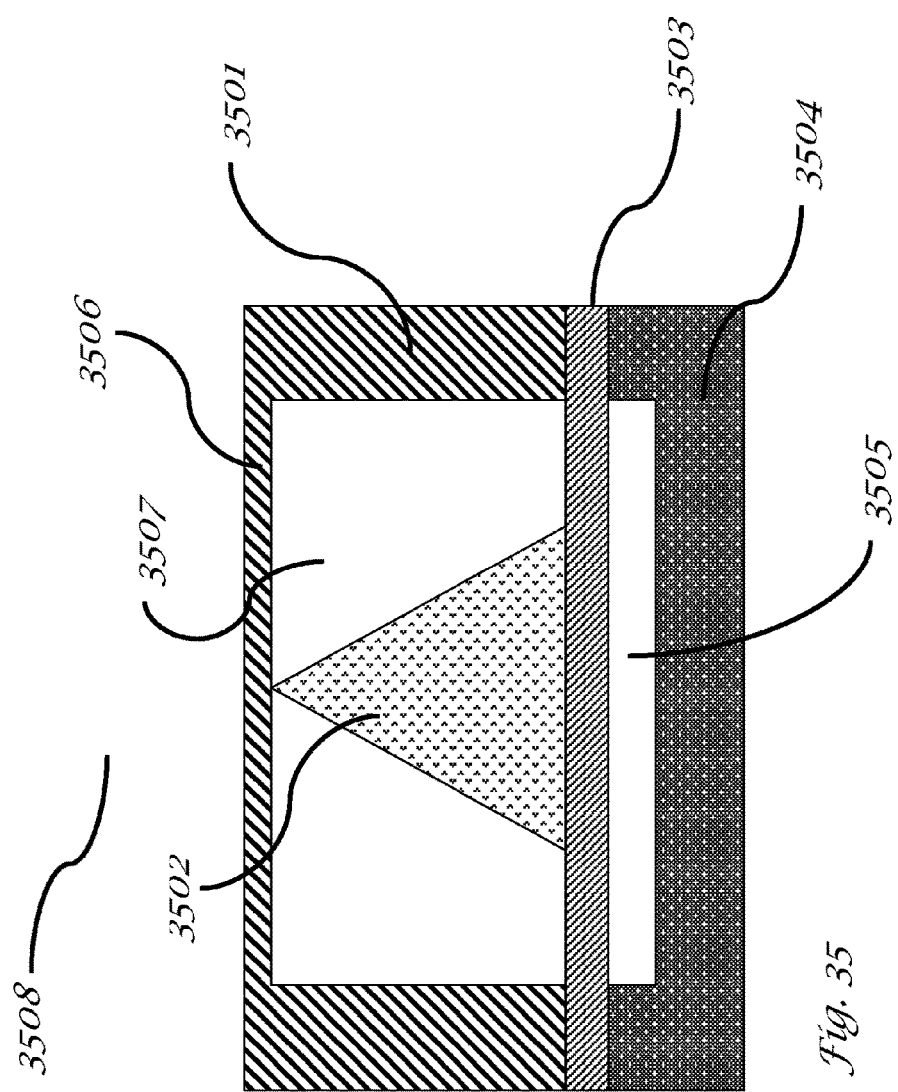
FIG. 35 shows a device wherein the structural elements of the device body and the mechanical structure are monolithic, in accordance with an embodiment of the invention.

In the embodiment shown in FIG. 35, the structural part/elements of the device body 3501 and the mechanical structure 3506, which separate the isolated cavity 3507 from the exterior environment 3508, may be built as a monolithic part. Illustratively, both the mechanical structure 3506 and the structural elements 3501, which are coupled to and support the mechanical structure 3506, may be fabricated using a manufacturing technology such as, for example and without limitation: MEMS fabrication, additive manufacturing (e.g., stereolithography, polyjet, inkjet printing, plastic laser sintering, direct metal laser sintering, fused deposition modeling, 3D printing in ceramic technology, etc.), micro injection molding, ceramic forming, high-speed micromachining, and electrical discharge machining. The material for manufacturing the mechanical structure 3506 and the device body 3501 is preferable of a brittle nature, allowing rapid collapse, rupture or fracturing once its mechanical integrity is compromised. Such rapid collapse would allow the device to emit a strong acoustic signal. Materials that could be suitable for manufacturing the mechanical structure and the device body include, without limitation: glass, silicon, ceramic and/or sapphire. The monolithic nature of the mechanical structure and structural elements may cause both to collapse simultaneously, further enhancing the acoustic emission.

The device also includes a passive timing mechanism 3504, which allows a timing cavity 3505 to fill with fluid over time, the pressure of said fluid eventually acting on the timing diaphragm 3503 so as to push the piercing structure 3502 into the mechanical structure 3506, causing its collapse. The passive timing mechanism 3504 may be a porous structure allowing slow seepage of fluid from the external environment 3508 into the timing cavity 3505, or it may be a fluidic circuit integrating a fluidic conduit that limits the rate at which the timing cavity fills with fluid. The timing mechanism 3504 may be bonded to the timing diaphragm 3503, the structural part/elements 3501 of the device body, or both, using, for example, an adhesive, ultrasonic welding, e-beam welding, soldering, or combination thereof.

The timing diaphragm 3503 may be manufactured out of any material allowing sufficient flexibility, preferably as a thin layer. This could be a metal layer that is bonded to the structural elements 3501 of the device body using, for example and implying no limitation, an adhesive, ultrasonic welding, e-beam welding, soldering, or combination thereof. The timing diaphragm 3503 may be an elastomeric membrane, or a plastic film, that is adhesively attached to the structural elements/part 3501. In various embodiments, a double-sided adhesive tape may be utilized. As shown in FIG. 35, the structural element(s) 3501, which are coupled to and support the mechanical structure 3506, along with the timing diaphragm 3503 (and in some embodiments other portions of the passive timing mechanism 3504) combine to form the isolated cavity 3507.

The piercing structure 3502 may be manufactured separately, using, without limitation, MEMS, ceramic or 3D-printing technology. Since the piercing structure 3502 is meant to apply local force to the mechanical structure 3506 in order to pierce it, rupture it or collapse it, it needs to be manufactured out of hard material capable to withstand significant compressive stress. Preferred materials would be silicon, ceramic, metal or hard plastics.

Figure 36:
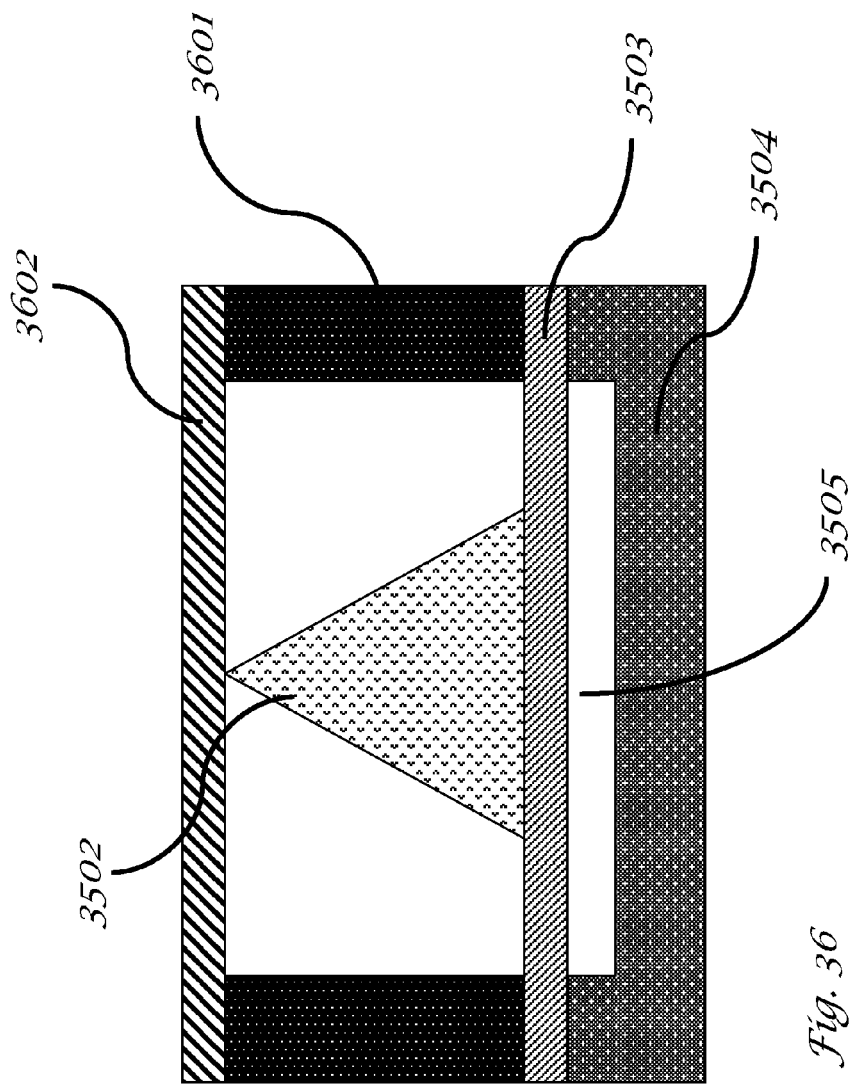
FIG. 36 shows a device wherein the structural elements of the device body and the mechanical structure are manufactured separately, in accordance with an embodiment of the invention.

FIG. 36 shows another embodiment of the device, where the structural elements of the device body 3601, and the mechanical structure 3602, are manufactured separately and then bonded using an appropriate bonding method, such as one of the technologies described above. The structural device body elements 3601 may be manufactured using traditional machining, or additive manufacturing (e.g., stereolithography, polyjet, inkjet printing, plastic laser sintering, direct metal laser sintering, fused deposition modeling, 3D printing in ceramic technology, etc.). Ideally, the materials used for the structural device body elements 3601 are selected to be able to withstand the stresses that are to be encountered during field deployment, e.g. injection in a well during hydraulic fracking operations. Such stresses can be either dynamic or static. Dynamic stresses are generated when devices pass through the pumps, or when they are flowing along with proppant before reaching the fractures. Static stresses are of isotropic (hydrostatic) nature (due, for example, to the pressure of the surrounding environment), or of non-isotropic nature (due, for example, to the fracture closure force). Some ductility may advantageously help in withstanding dynamic stresses without collapsing. Preferred materials for the structural body elements 3601 include metals, strong plastics, and resins. Other materials may include ceramics, glass or silicon, which can be sufficiently strong but are more brittle.

The mechanical structure 3602, on the other hand, may be manufactured in a strong brittle material that will rapidly rupture or collapse when the piercing structure 3502 starts applying stress. Such rapid collapse is important for the device to emit a strong acoustic signal. Materials that could be suitable for manufacturing the mechanical structure 3602 include, without limitation: glass, sapphire, silicon and ceramic. Illustratively, MEMS technology, using silicon or glass substrates is well adapted to manufacturing the mechanical structure 3602. MEMS etching techniques that may be used include deep reactive ion etching, inductively coupled plasma reactive ion etching, isotropic wet etching, and anisotropic wet etching.

Compared to the device shown in FIG. 35, the device of FIG. 36 may therefore better withstand real-world applications, and particularly resist external mechanical stresses. This is due to the choice of the appropriate materials and manufacturing techniques for each part of the device, according to its function.

Figure 37:
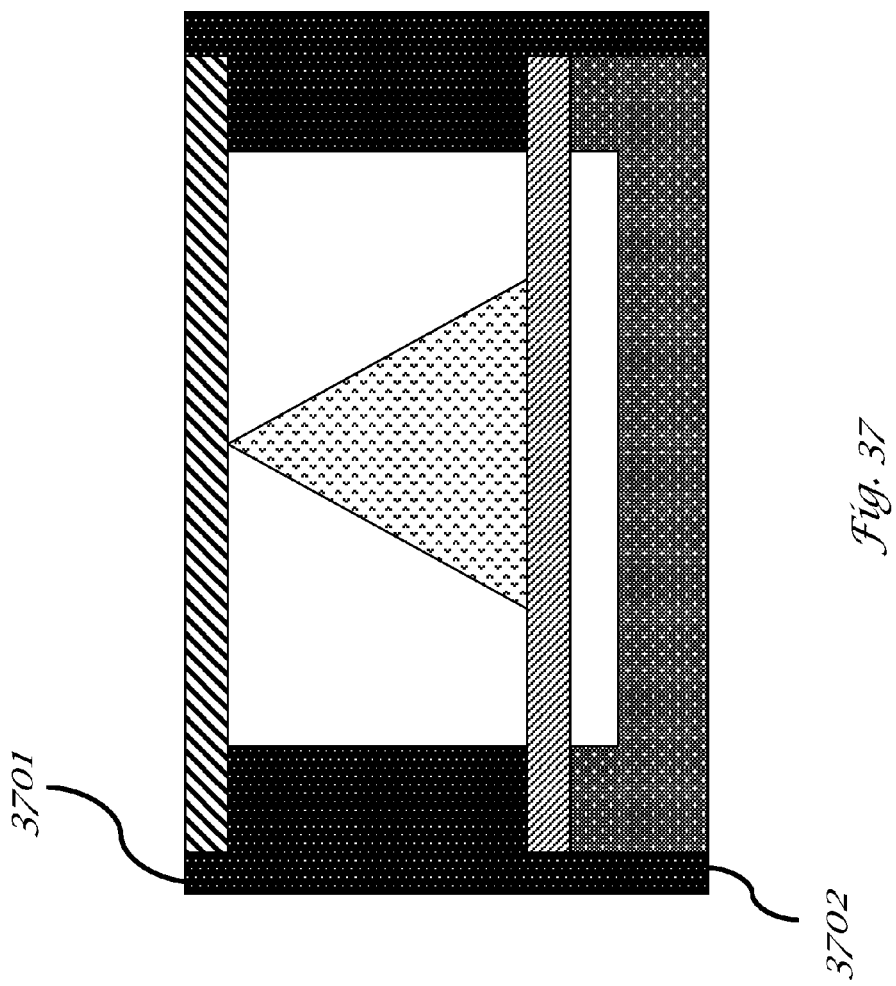
FIG. 37 shows the structural elements of the device body of FIG. 36 incorporating additional protection features, in accordance with an embodiment of the invention.

Furthermore, in FIG. 37, the structural elements/part of the device body of FIG. 36 is shown incorporating additional protection features 3701 and 3702, such as, without limitation, various types of lap joints, for the mechanical structure and for the timing mechanism, respectively. This may provide yet better resistance to mechanical stresses, by isolating and cushioning the brittle elements of the device. Such protective features could be incorporated in all the designs presented, and will not be systematically described.

Figure 38:
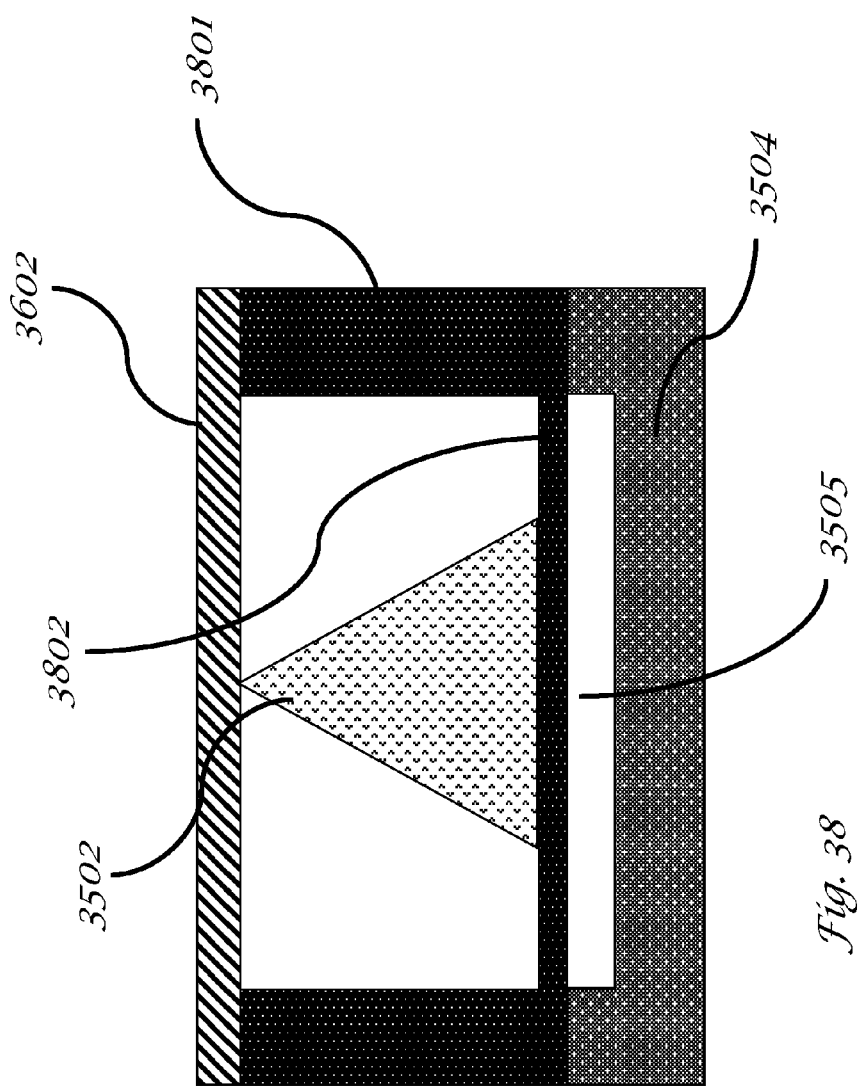
FIG. 38 shows a device wherein the structural elements of the device body and the timing diaphragm 3802 are monolithic, in accordance with an embodiment of the invention.

FIG. 38 shows another embodiment of the invention, in which the device body structural elements/parts 3801 and the timing diaphragm 3802 are manufactured as a monolithic structure, and bonded to the other device elements such as the mechanical structure 3602, and the timing mechanism 3504. Different methods can be applied for manufacturing the monolithic structure mentioned above, but additive manufacturing has important potential advantages such as the ability to create intricate geometries at small scale. Possible additive technologies that may be applied include: stereolithography, polyjet, inkjet printing, plastic laser sintering, direct metal laser sintering, fused deposition modeling, 3D printing in ceramic technology, and other similar technologies known in the art that are commercialized under different names.

Figure 39:
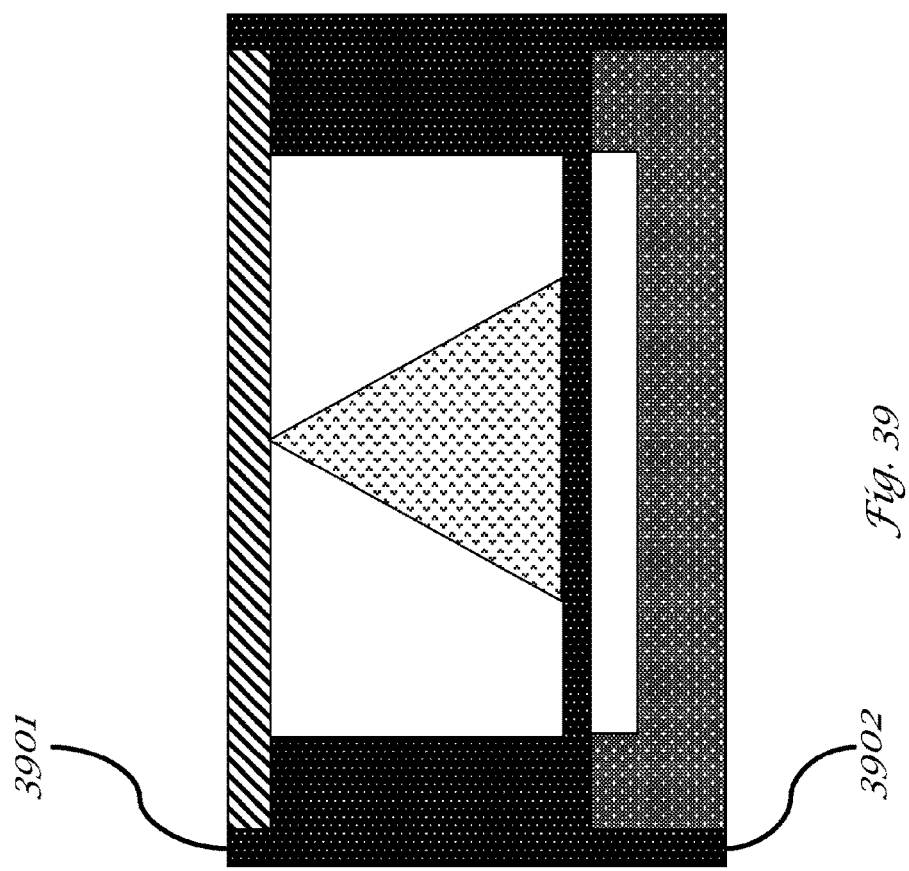
FIG. 39 shows a device wherein the structural elements of the device body of FIG. 38 incorporate additional protection features for the mechanical structure and for the timing mechanism, in accordance with various embodiments of the invention.

Similarly to FIG. 37, FIG. 39 shows the structural elements/part of the device body of FIG. 38 incorporating additional protection features 3901 and 3902 for the mechanical structure and timing mechanism, respectively, in accordance with various embodiments of the invention. The additional protection features 3901 and 3902 may include, without limitation, various types of lap joints. This may provide yet better resistance to mechanical stresses, by isolating and cushioning the brittle elements of the device. Such protective features could be incorporated in all the designs presented, and will not be systematically described.

Figure 40:
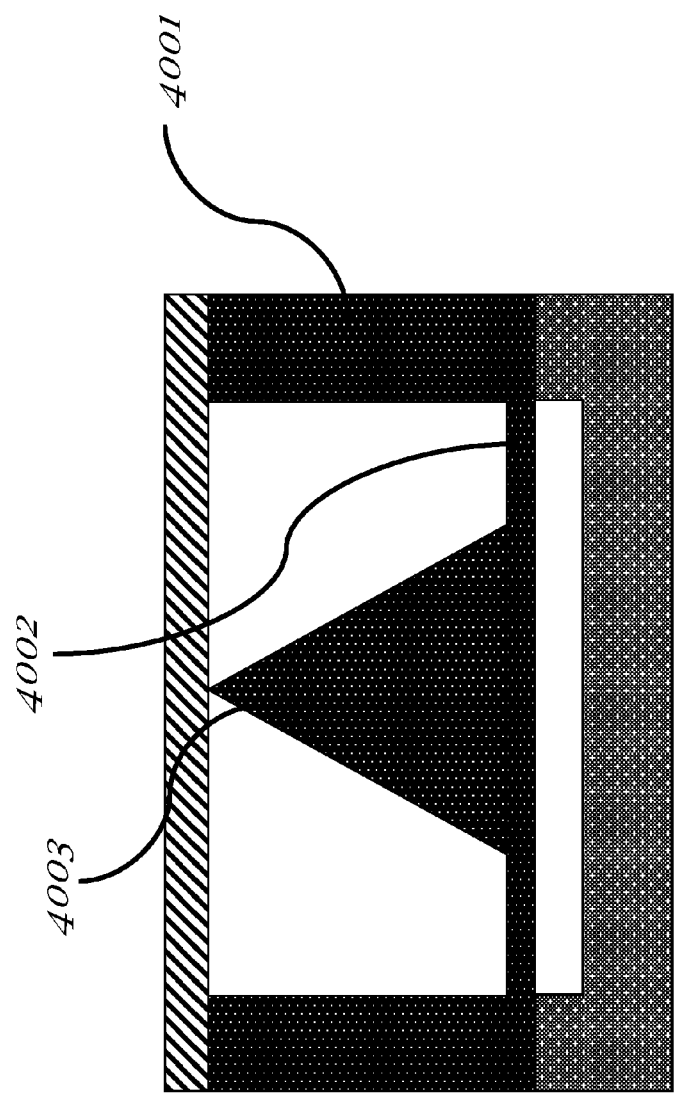
FIG. 40 shows a device in which the structural elements, timing diaphragm, and piercing structure are manufactured monolithically, in accordance with an embodiment of the invention.

FIG. 40 shows a device in which the structural elements/body parts 4001, timing diaphragm 4002, and piercing structure 4003 are manufactured monolithically, in accordance with an embodiment of the invention. Different methods can be applied for manufacturing the monolithic structure mentioned above, but additive manufacturing has important potential advantages such as the ability to create intricate geometries at small scale. Possible additive technologies that may be applied include: stereolithography, polyjet, inkjet printing, plastic laser sintering, direct metal laser sintering, fused deposition modeling, 3D printing in ceramic technology, and other similar technologies that are commercialized under different trade names. Such devices may also be manufactured using precision plastic injection molding.

Figure 41:
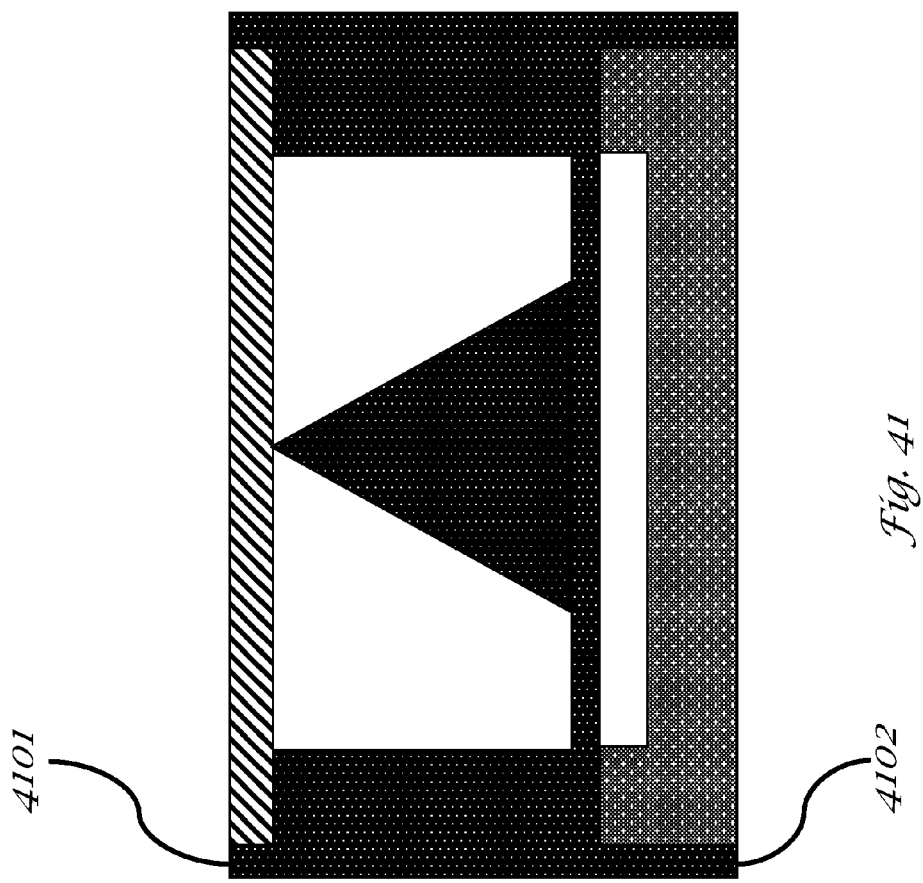
FIG. 41 shows structural elements of the device body of FIG. 40 incorporating additional protection features for the mechanical structure and timing mechanism.

Similarly to FIGS. 37 and 39, FIG. 41 shows the structural part of the device body of FIG. 40 also incorporating additional protection features 4101 and 4102 for the mechanical structure and timing mechanism, respectively. The additional protection features 4101 and 4102 may include, without limitation, various types of lap joints. This may provide yet better resistance to mechanical stresses, by isolating and cushioning the brittle elements of the device. Such protective features could be incorporated in all the designs presented, and will not be systematically described.

Figure 42:
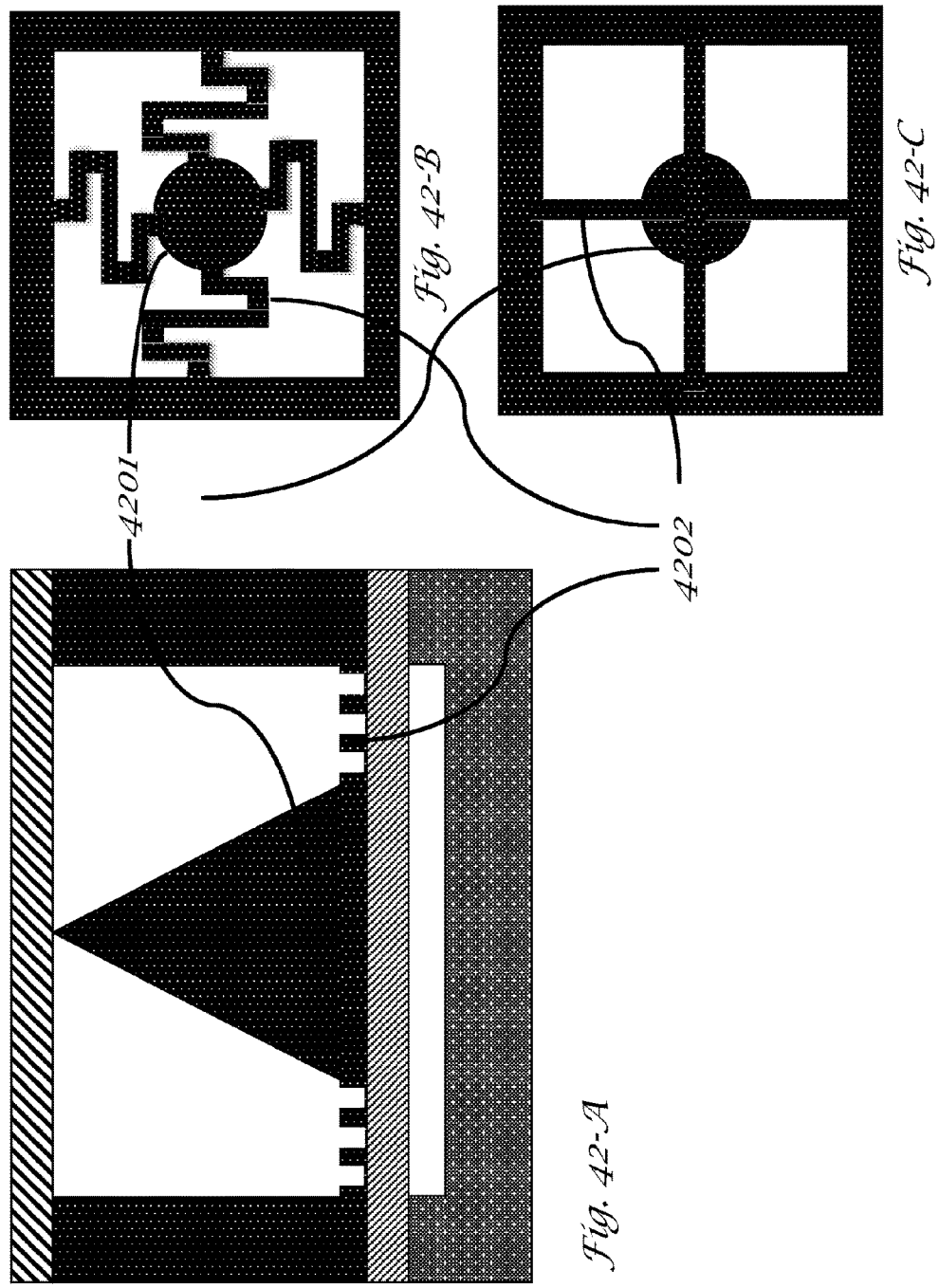
FIG. 42A shows a lateral cross-section of a device where the structural device body parts and the piercing structure are manufactured monolithically, in accordance with an embodiment of the invention.
FIGS. 42B and 42C show top views of the device presented in FIG. 42A, exemplifying possible hinge geometries, in accordance with various embodiments of the invention.

FIG. 42A shows a lateral cross-section of a device where the structural device body parts and the piercing structure 4201 are manufactured monolithically, including hinges/linkages 4202 that allow attaching and centering the piercing structure 4201 within the device, while providing the piercing structure 4201 the ability to move in a direction perpendicular to the plane of the linkages, in accordance with an embodiment of the invention. FIGS. 42B and 42C show top views of the device presented in FIG. 42A, exemplifying possible hinge geometries.

The structural device body parts may be bonded to the timing diaphragm using different techniques listed above. Different methods can be applied for manufacturing the monolithic structure mentioned above, but additive manufacturing has important potential advantages such as the ability to create intricate geometries at small scale. Possible additive technologies that may be applied: stereolithography, polyjet, inkjet printing, plastic laser sintering, direct metal laser sintering, fused deposition modeling, 3D printing in ceramic technology and other similar technologies that are commercialized under different trade names.

Figure 43:
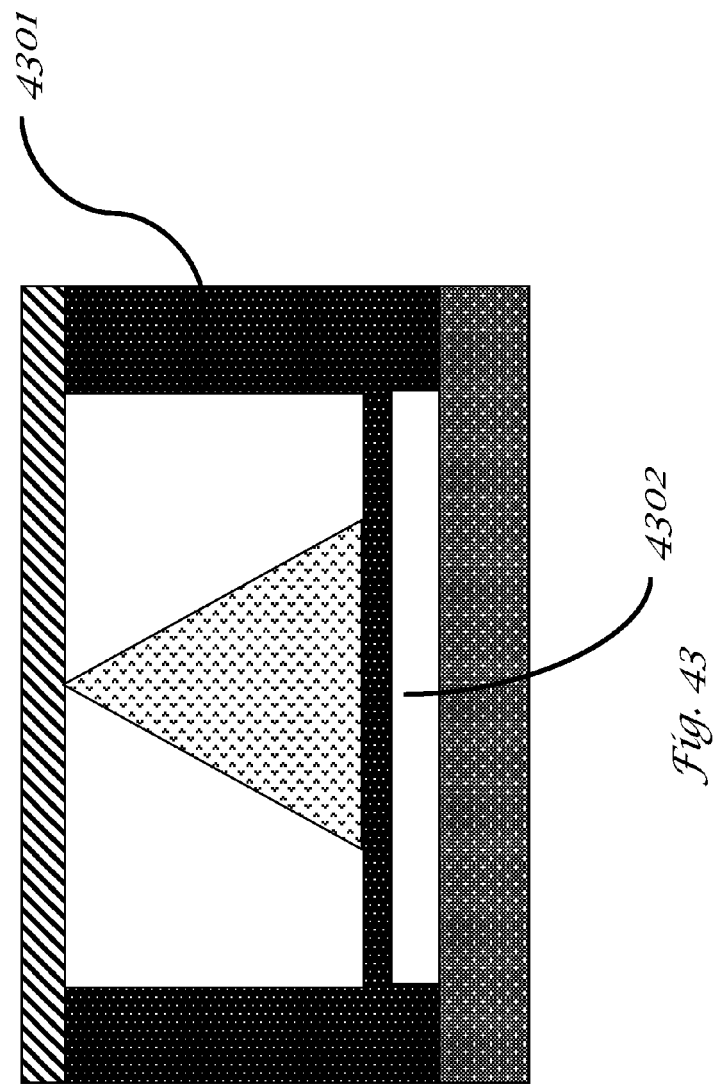
FIG. 43 shows a device where the structural elements/body parts and timing diaphragm are built monolithically, but integrating also the timing cavity 4302, in accordance with an embodiment of the invention.
Figure 44:
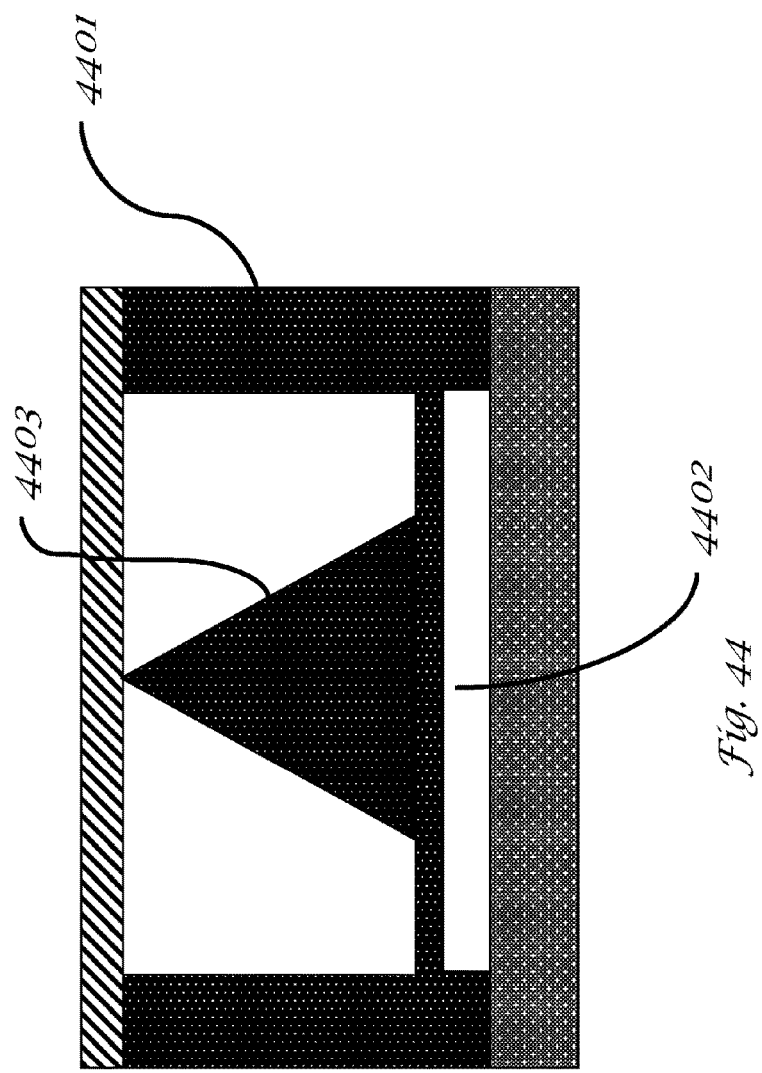
FIG. 44 shows a device similar to FIG. 43, where the monolithic part of the device further incorporates the piercing structure, in accordance with an embodiment of the invention.

FIG. 43 shows a device where the structural elements/body parts 4301 and timing diaphragm are built monolithically, but integrating also the timing cavity 4302, in accordance with an embodiment of the invention. FIG. 44 shows a similar device, where the monolithic part of the device further incorporates the piercing structure 4403. Different methods can be applied for manufacturing the monolithic structures mentioned above and shown in FIGS. 43 and 44, but additive manufacturing has important potential advantages such as the ability to create intricate geometries at a small scale, and in strong materials. Possible additive technologies that could be applied include : stereolithography, polyjet, inkjet printing, plastic laser sintering, direct metal laser sintering, fused deposition modeling, 3D printing in ceramic technology and other similar technologies that are commercialized under different trade names. Such devices may also be manufactured using precision plastic injection molding.

In general, the above-described devices may be monolithic or hybrid devices. In various embodiments, the structural elements, the mechanical structure, the timing mechanism and/or the piercing structure may be manufactured using additive manufacturing technologies selected from the group consisting of stereolithography, polyjet, inkjet printing, plastic laser sintering, direct metal laser sintering, fused deposition modeling, 3D printing in ceramic technology, and combinations thereof. In various embodiments, the structural elements, mechanical structure, timing mechanism, and/or piercing structure are manufactured using MEMS etching techniques selected from the group consisting of deep reactive ion etching, inductively coupled plasma reactive ion etching, isotropic wet etching, anisotropic wet etching and combinations thereof.

Figure 45:
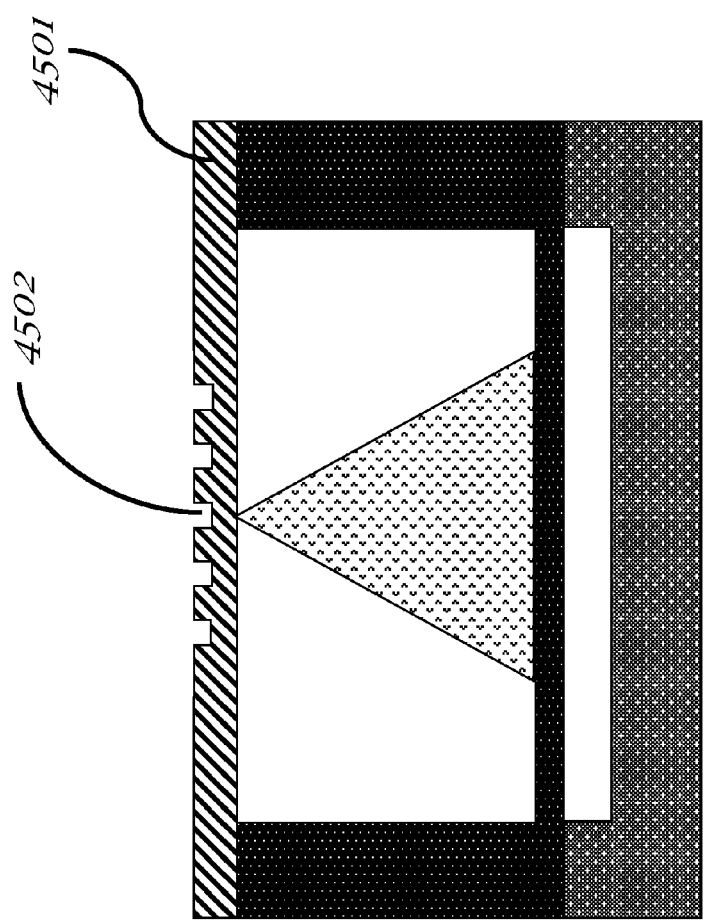
FIG. 45 shows a device where the mechanical structure further includes an etched geometry on the top surface, near the center, in accordance with an embodiment of the invention.

FIG. 45 shows a device where the mechanical structure 4501 further includes an etched geometry 4502 on the top surface, near the center, in accordance with an embodiment of the invention. Such etched geometry may help amplify stresses when the piercing structure starts applying force.

Ideally, such etched geometry may be placed, without limitation, in regions of the mechanical structure that are normally under compressive stress, but that develop tensile stress under the action of the piercing structure. In the case of geometry etched on the top side of the mechanical structure, this may correspond to its center area, close to where the piercing structure applies its force. Regions other than the center area of the top surface of the mechanical structure 4501 may also be etched.

Figure 46:
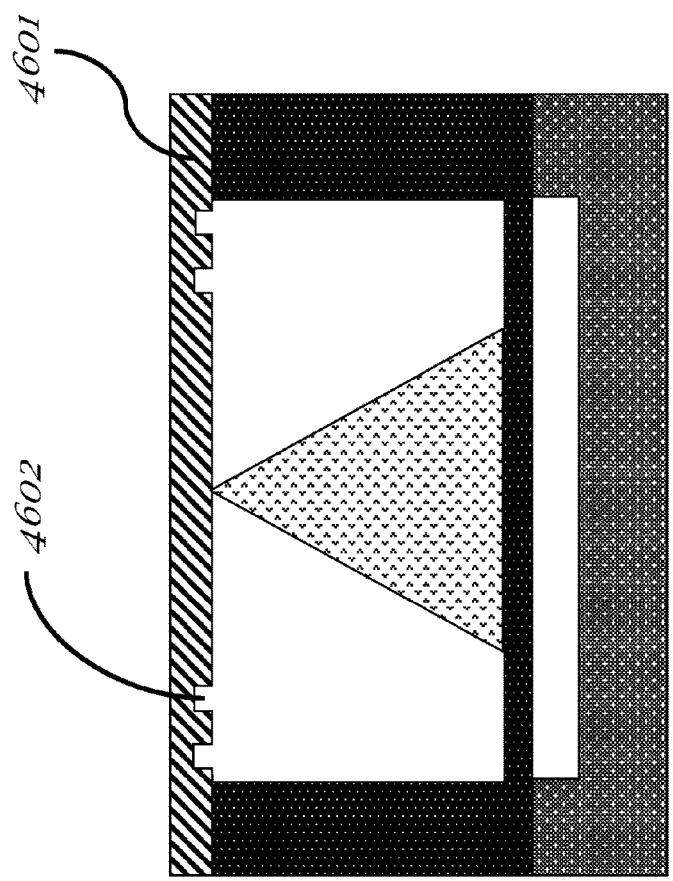
FIG. 46 shows a device where the mechanical structure further includes an etched geometry on the bottom surface, near the outer edge, in accordance with an embodiment of the invention.

FIG. 46 shows a device where the mechanical structure 4601 further includes an etched geometry 4602 on the bottom surface, near the outer edge, in accordance with an embodiment of the invention. Ideally such etched geometry should be placed in regions of the mechanical structure that are normally under compressive stress, but that develop tensile stress under the action of the piercing structure. In the case of geometry etched on the bottom surface of the mechanical structure, this may correspond to its outer edge. Regions other than the outer edge of the bottom surface of the mechanical structure 4501 may also be etched.

FIG. 47A shows typical elastic deflection of a circular clamped membrane under hydrostatic pressure applied to the top side, in accordance with an embodiment of the invention. The deflection and radius are normalized on the graph. The region of compressive stress at the top membrane surface is contained within the inflection radius (which corresponds to a circular region of diameter $D/\sqrt{3}$, D being the membrane outer diameter).

FIG. 47-B shows a cross-section through a circular mechanical structure 4702, and one possible positioning of the top-side etched geometry 4703, contained between the inflection radius of the circular structure 4702, in accordance with an embodiment of the invention.

FIGS. 47C, 47D, 47E shows top views of possible top-side etched geometries: radial etch configuration (FIG. 47C), concentric circles etch configuration (FIG. 47E) and combined radial and concentric circles configuration (FIG. 47D), in accordance with various embodiments of the invention.

FIG. 48A shows a mechanical structure 4801 geometry which has a membrane-like portion delimited by etching 4802, in accordance with an embodiment of the invention. The membrane-like portion of the mechanical structure may have further geometries 4803 etched into it, on either side, as shown in FIGS. 48B and 48C.

It is understood that partial etched geometries of the mechanical structure, or of other device parts, could be incorporated in all the designs presented, and will not be systematically described.

FIG. 49 show different ways to manufacture the passive timing mechanism of the device, in accordance with various embodiments of the invention. More particularly, FIG. 49A shows the passive timing mechanism 4901 as a porous structure allowing slow seepage of fluid from the external environment into the timing cavity. The timing cavity 4902 may be integrated to the passive timing mechanism, as shown in FIG. 49B, or may not be integrated, as shown in FIG. 49A. FIGS. 49C and 49D show the passive timing mechanism as a fluidic circuit 4903 integrating a fluidic conduit 4904 that limits the rate at which the timing cavity fills with fluid. The timing cavity 4905 may or may not be integrated to the passive timing mechanism.

FIG. 50 shows the device of FIG. 35, but where the timing diaphragm is replaced by a piston structure 5001, which uses a moving seal 5002 to allow movement without allowing fluid to flow past. It is implied that the configurations described above using a timing diaphragm can be adapted to using a piston in a straight-forward manner.

In summary, the above-described devices enable a variety of functionalities. These functionalities include, without limitation, the following:

1. mechanical protection and hermetic transport of the device within the external environment (by pumping or injection), or deployment within various measurement tools;
2. sample acquisition, material release and/or chemical reaction in-situ at pre-defined times, using passive microfluidic timing mechanisms that may include, without limitation, a diaphragm or a piston;
3. sample isolation from external medium prior to and after acquisition (cross-contamination control);
4. integrated redundancy mechanisms to assure correct device operation even in cases of failure of one of the sample mechanisms;
5. monolythic integration with standard sensor technologies;
6. three-dimensional positioning using coded and/or uncoded acoustic signal emission;
7. external sensor interrogation capability after retrieval at the surface;
8. filtering
9. measuring viscosity of an external fluid;
10. maintaining a sample at high pressure after sample acquisition, to ensure sample integrity and single-phase character;
11. complex sample manipulations, filter backflushing, and transfer between vials;
12. use of a manifold in sampling system
13. chemical/biochemical/microbiological sample measurement(s);
14. integration of optical elements within or around the sample chamber
15. daisy chain configuration of multiple sampling systems;
16. external control of sampling time/triggered sampling implementation;
17. modifying sampling timing using different passive timing durations (for example, by changing the timing cavity volume);
18. pollution monitoring system/deployment
19. monitoring functionality (for example, time stamping and/or sample acquisition monitoring)

The above-described devices provide robust, highly miniaturized smart passive sample chambers/vessels that can be integrated with several sensor technologies to perform critical in-situ measurements for, without limitation, the oilfield, the ocean, or a living body, or to provide information about the positioning of devices during fluid injection or fracturing operations. One of the main features of the device is its capability to provide a robust timing mechanism to perform, for example, measurements or material release on a pre-defined (or post-inferred) schedule, and/or to emit acoustic signal sequences, which will allow triangulation of the vessel position, thus indicating fluid movement and fracture propagation, within a hydrocarbon reservoir, or other pressurized formation or system. From fracture propagation modeling relative to induced pressures, formation mechanical properties and stress analysis can be performed in-situ. The device may be integrated with standard sensing technologies, allowing a specific measurement or set of measurements to be performed on an isolated fluid sample. The device may also be utilized as part of a proppant formulation during hydraulic fracturing jobs, whereas the passive devices are mixed with slurries and sand grains and are injected alongside into a formation. The device may be used to as a vehicle for time-release of particles, chemical products, or pharmaceutical products. The device may be used in autonomous devices, for example, on robots such as marine remotely-operated underwater vehicles, autonomous underwater vehicles, airborne or ground drones and vehicles, and other types of robotic equipment. The device may be used to monitor flow of external fluids/gases/pollution/contamination in and around, without limitation, cities, chemical plants, nuclear sites, remote regions without power, offshore platforms and other oilfield structures, military missions and battlegrounds.

These combined capabilities result, without limitation, in a very versatile device capable of being implemented within a tool or injected or otherwise deployed in a formation, or living body, or other body of fluid, to provide measurements on samples acquired and/or to release particles, at different locations in, without limitation, an oil reservoir, living body, or other body of fluid, and at multiple times, and to communicate its position via, for example, acoustic emission.

The embodiments of the invention described above are intended to be merely exemplary; numerous variations and modifications will be apparent to those skilled in the art. All such variations and modifications are intended to be within the scope of the present invention. These and other obvious modifications are intended to be covered by the claims that follow.

What is claimed is:

1. A device comprising:
    an isolated cavity that is initially inaccessible to the external fluid;
    a device body including one or more structural elements supporting a mechanical structure, the mechanical structure separating the isolated cavity from the external fluid;
    a piercing structure for piercing the mechanical structure;
    an electrically passive timing mechanism including a fluidic timing cavity, wherein at the end of a timing interval fluid within the timing cavity causes a piercing structure to pierce the mechanical structure, causing the mechanical structure to collapse, rupture and/or fracture,
    wherein an acoustic signal is emitted when the mechanical structure is pierced.

2. The device according to claim 1, wherein the structural elements are made of a material that is different from the mechanical structure.

3. The device according to claim 2, wherein the structural elements include a material selected from the group consisting of a ceramic, metal, a plastic and a resin, and combinations thereof, and wherein the mechanical structure includes a material selected from the group consisting of silicon, ceramic, sapphire and glass, and combinations thereof.

4. The device according to claim 1, wherein the structural elements, the mechanical structure, the timing mechanism and/or the piercing structure are manufactured using additive manufacturing technologies selected from the group consisting of stereolithography, polyjet, inkjet printing, plastic laser sintering, direct metal laser sintering, fused deposition modeling, 3D printing in ceramic technology, and combinations thereof.

5. The device according to claim 1, wherein at least one of the structural elements, mechanical structure, timing mechanism, and/or piercing structure are manufactured using MEMS etching techniques selected from the group consisting of deep reactive ion etching, inductively coupled plasma reactive ion etching, isotropic wet etching, anisotropic wet etching and combinations thereof.

6. The device according to claim 1, wherein the mechanical structure is more brittle than the structural elements.

7. The device according to claim 1, wherein the piercing structure is made from a material that is different from the mechanical structure.

8. The device according to claim 1, wherein the piercing structure is made from the same material as the structural elements.

9. The device according to claim 1, wherein the piercing structure and the structural elements are coupled via linkages that permit movement of the piercing structure.

10. The device according to claim 9, wherein the piercing structure, the structural elements and the linkages are manufactured monolithically.

11. The device according to claim 1, wherein the mechanical structure and the structural elements are manufactured monolithically.

12. The device according to claim 1, wherein the mechanical structure has a top and bottom surface, the top surface for facing the external fluid and the bottom surface for facing the piercing structure, wherein the mechanical structure includes partially etched geometry on the top surface and/or the bottom surface.

13. The device according to claim 1, wherein the external fluid entering the fluidic timing cavity applies pressure to a timing diaphragm and/or piston so as to drive the piercing structure into the mechanical structure, causing the mechanical structure to collapse.

14. The device according to claim 13, wherein the timing diaphragm includes a material selected from the group consisting of a metal and a polymer, and combinations thereof.

15. The device according to claim 13, wherein the electrically passive timing mechanism includes a porous structure and/or material that allows the external fluid to seep into the fluidic timing cavity.

16. The device according to claim 13, wherein the electrically passive timing mechanism includes a fluidic circuit that allows the external fluid to enter the fluidic timing cavity.

17. A method of making the device of claim 1, the method comprising:
    using MEMS etching techniques selected from the group consisting of deep reactive ion etching, inductively coupled plasma reactive ion etching, isotropic wet etching, and anisotropic wet etching, or combinations thereof, to make the structural elements, the piercing structure, the passive timing mechanism and/or the mechanical structure.

18. A method of making the device of claim 1, the method comprising:
    using an additive manufacturing technology selected from the group consisting of stereolithography, polyjet, inkjet printing, laser sintering, fused deposition modeling, and 3D printing, and combinations thereof, to make the structural elements, the piercing structure, the passive timing mechanism, and/or the mechanical structure.

19. The method according to claim 18, wherein the structural elements include materials selected from the group of a metal, a ceramic, a plastic and a resin, and combinations thereof.

20. The method according to claim 19, wherein the mechanical structure includes materials selected from the group consisting of silicon, ceramic, sapphire, and combinations thereof.

21. The method according to claim 20, wherein the method further includes using MEMS technology to make the mechanical structure.

22. A method of making the device of claim 1, wherein the mechanical structure has a top and bottom surface, the top surface for facing the external fluid and the bottom surface for facing the piercing structure, wherein the method comprises partially etching the top surface and/or the bottom surface.

23. The method of making the device of claim 1, comprising coupling the piercing structure and the structural elements via linkages so as to permit movement of the piercing structure.

24. A method of making the device of claim 23, the method further comprising monolithically manufacturing the piercing structure and the structural elements.

25. A method of making the device of claim 1, the method further comprising monolithically manufacturing the mechanical structure and the structural elements.

* * * * *